US006107050A

United States Patent [19]
Alkon et al.

[11] Patent Number: 6,107,050
[45] Date of Patent: Aug. 22, 2000

[54] DIAGNOSTIC TEST FOR ALZHEIMERS DISEASE

[75] Inventors: Daniel L. Alkon; Antonelle R. Favit; Maurizio Grimaldi, all of Bethesda, Md.

[73] Assignee: The United States of America as represented by the Department of Health and Human Services, Washington, D.C.

[21] Appl. No.: 09/075,725

[22] Filed: May 11, 1998

Related U.S. Application Data

[63] Continuation-in-part of application No. 08/809,646, Jul. 18, 1997, which is a continuation-in-part of application No. 08/312,202, Sep. 26, 1994, Pat. No. 5,976,816, which is a continuation-in-part of application No. 08/056,456, May 3, 1993, Pat. No. 5,580,748.

[51] Int. Cl.$^7$ .................................................. G01N 33/573
[52] U.S. Cl. ...................... 435/7.4; 435/7.21; 435/7.92; 436/63; 436/518; 436/524; 436/528; 436/811
[58] Field of Search .................................... 435/7.1, 7.21, 435/7.4, 7.92, 7.93, 7.95; 436/518, 501, 524, 528, 63, 811

[56] References Cited

U.S. PATENT DOCUMENTS 4,925,664  5/1990  Jackson et al. .
5,580,748  12/1996  Alkon et al. .

OTHER PUBLICATIONS

Zohar et al., (1998) *Biophys. J.*, 74:82–89, Thermal Imaging Of Receptor–Activated Heat Production In Single Cells.

Favit et al., (1998) *Proc. Natl Ac. Sciences*, 95(10):5562–7, Alzheimer's–Specific Effects Of Soluble B–Amyloid On Protein Kinase C–Alpha And –Gamma Degradation In Human Fibroblasts.

Favit et al., (1997) Society for Neuroscience, 27$^{th}$ Annual Meeting, New Orleans, Oct. 25–30, 1997, Abstract 118.2, PKC Isoenzymes Are Differentially Affected By Low Concentrations Of Soluble B–Amyloid Protien In Alzheimer's Disease.

R. Etcheberrigaray et al., *Soc. Neurosci Abstract*, vol. 18, Oct. 25–30, 1992 "Distinguishing Features of Potassium Channels in Fibroblasts From Alzheimer Aged and Young Donors".

D. Dewar et al., *Neurobiol. Aging.* vol. 13 (Suppl. 1), Jul. 12–17, 1992 "Multiple Ion Channel Binding Sites are Differentially Altered in Alzheimer's Disease Cortex".

M. Ikeda et al. *Brian Res.* vol. 567, pp. 51–56 (1991) "Selective Reduction of Iodine–125 Apamin Binding Sites in Alzheimer's Hippocampus: A Quantitative Autoradiographic Study".

B. Sakmann and E. Neker, *Ann Rev. Physiol.* vol. 46, pp. 455–72 (1984) "Patch Clamp Techniques For Studying Ionic Channels in Excitable Membranes".

E. Ito et al., *Neuroscience Research*, vol. 18: Abstract 615 (1993) "A Laboratory Diagonsis Of Alzheimer's Disease With Patch–Clamp and Ca2+–imaging techniques".

R. Etcheberrigaray et al., *Proceedings Of The National Academy Of Sciences* (USA) vol. 90, No. 17. 8209–8213 (1993) "Potassium channel dysfunction in fibroblasts identifies patients with Alzheimer disease."

E. Ito et al., *Proceedings Of The National Academy Of Sciences* (USA) vol. 91, No. 2, pp. 534–538 (1994) "Internal Ca2+ mobilization is altered in fibroblasts from patients with Alzheimer disease".

H.M. Huang et al., *Neurobiology Of Aging*, vol. 12: pp. 469–473 (1994) "Inositol Phosphates and Intracellular Calcium After Bradykinin Stimulation in Fibroblasts From Young, Normal Aged and Alzheimer Donors".

A. Grossmann et al., *Neurobiology of Aging*, vol. 14, No. 2: 177–185 (1993) "Intracellular Calcium Response Is Reduced in CD4+ Lymphocytes in Alzheimer's Disease and in Older Persons with Down's Snydrome".

C. Paterson et al., *Neurobiology Of Aging*, vol. 9, No. 3:261–266 (1988) "Altered response of Fibroblasts From Aged and Alzheimer Donors to Drugs That Elevate Cytosolic Free Calcium".

Database WPI—Derwent Publications Led. London GB, AN 94–146876 JPA 06,009693 (Elken Kagakukk), Jan. 18, 1994.

A.F. Ghuysen–Itard et al., *Gerontology*, vol. 39:163–169 (1993) "Loss of Calcium—Homeostatic Mechanisms in Polymorphouclear Leukocytes of Demented and Nondemented Elderly Subjects".

A. Adunsky et al., *Journal of Neuroimmunology*, vol. 33:167–172 (1991) "Increased Cytosolic Free Calcium In Lymphocytes of Alzheimer Patients".

M. Ideda et al., *Brian Research*, vol. 567 51–56 (1991) "Selective Reduction of [$^{125}$I]apamin binding sites in Alzeimer Hippocampus: A Quanitive Autoradiographic Study".

D. Crespo et al., *Mechanisms of Aging and Development*, vol. 62:223–229 (1992) "The Influence of Age On Supraoptic Nucleus Neurons Of The Rat: Morphometric And Morphologic Changes".

(List continued on next page.)

*Primary Examiner*—Patricia A. Duffy
*Attorney, Agent, or Firm*—Morgan & Finnegan

[57] ABSTRACT

The present invention provides methods for the diagnosis of Alzheimer's disease using human cells. Specifically, one method detects differences between potassium channels in cells from Alzheimer's patient and normal donors, and differences in intracellular calcium concentrations between Alzheimer's and normal cells in response to chemicals known to increase intracellular calcium levels. Other methods detect differences between the memory associated GTP binding Cp20 protein levels between Alzheimer's and normal cells. Another method utilizes the differential effects of β-amyloid protein on levels of the protein kinase C isoenzymes PKCα and PKCγ in Alzheimer's and normal cells. Yet another method detects Eu-TTA fluorescence differences between Alzheimer's and normal cells treated with an activator of a receptor-mediated metabolic pathway. In addition a diagnostic index for improved assessment between Alzheimer's and non Alzheimer's cells is provided.

11 Claims, 42 Drawing Sheets

OTHER PUBLICATIONS

Alkon et al., *J. Neurochem*, vol. 51:903 (1988), "Regulation of Hermissenda K+ channels by Cytoplasmic and Membrane–Associated C–Kinase".

J.T. Nearly et al., *Nature*, vol. 293:658 (1981), "Change In A Specific Phosphoprotein band Following Associative Learning In Hermissenda".

T.J. Nelson et al., *J. Neurochem*, vol. 57:2065 (1991), "Classical Conditioning–Induced Changes in Low–Molecular–Weight GTP–Binding Proteins in Rabbit Hippocampus".

Alkon et al., *PNAS* (USA) vol. 87:1611 (1990), "Contraction of Neuronal Branching Volume: An Anatomic Correlate of Pavlovian Conditioning".

S. Moshiach et al., *Brian Research*, vol. 605:298 (1993), "G–Protein Effects On Retrograde Axonal Transport".

T.J. Nelson et al., *Science*, vol. 247:1479 (1990), "Isolation of G Protein That is Modified by Learning and Reduces Potassium Counts in Hermissenda".

R. Etcheberrigaray et al., *Science*, vol. 264:276 (1994), "Soluble β–Amyloid Induction of Alzheimer's Phenotype for Human Fibroblast K+ Channels".

Lederhendler, I. Izja, et al. (1990) "Outgrowths From Hermissenda Photoreceptor Somata Are Associated With Activation Of Protein Kinase C" *Brian Research* 534:195–200.

Lederhendler, I. Izja, et al. (1991) "Outgrowths From Hermissenda Photoreceptor Somata Are Associated With Activation Of Protein Kinase C" *Nonmammalian Biochem* 114;451, #Abstract 39648Q.

Etcheberrigaray, et al. (1993) "New Implications Of Memory Mechanism For Alzheimer's Disease" *Neuroscience Research Communications* vol. 13:S7–S10.

Peterson et al. (1986) "Cytosolie Free Calcium and Cell Spreading Decrease in Fibroblasts from Aged and Alzheimer Donors" *Proc. Natl. Acad. Sci.* vol. 83:7999–8001.

Gunnerson et al. (1991) "Preliminary Characterization of a Novel Alzheimer Disease Associated Protein" vol. 17:1–2 (#275.5).

Vesting, BBA, 1453(3):341–350, 1999 Abstract.

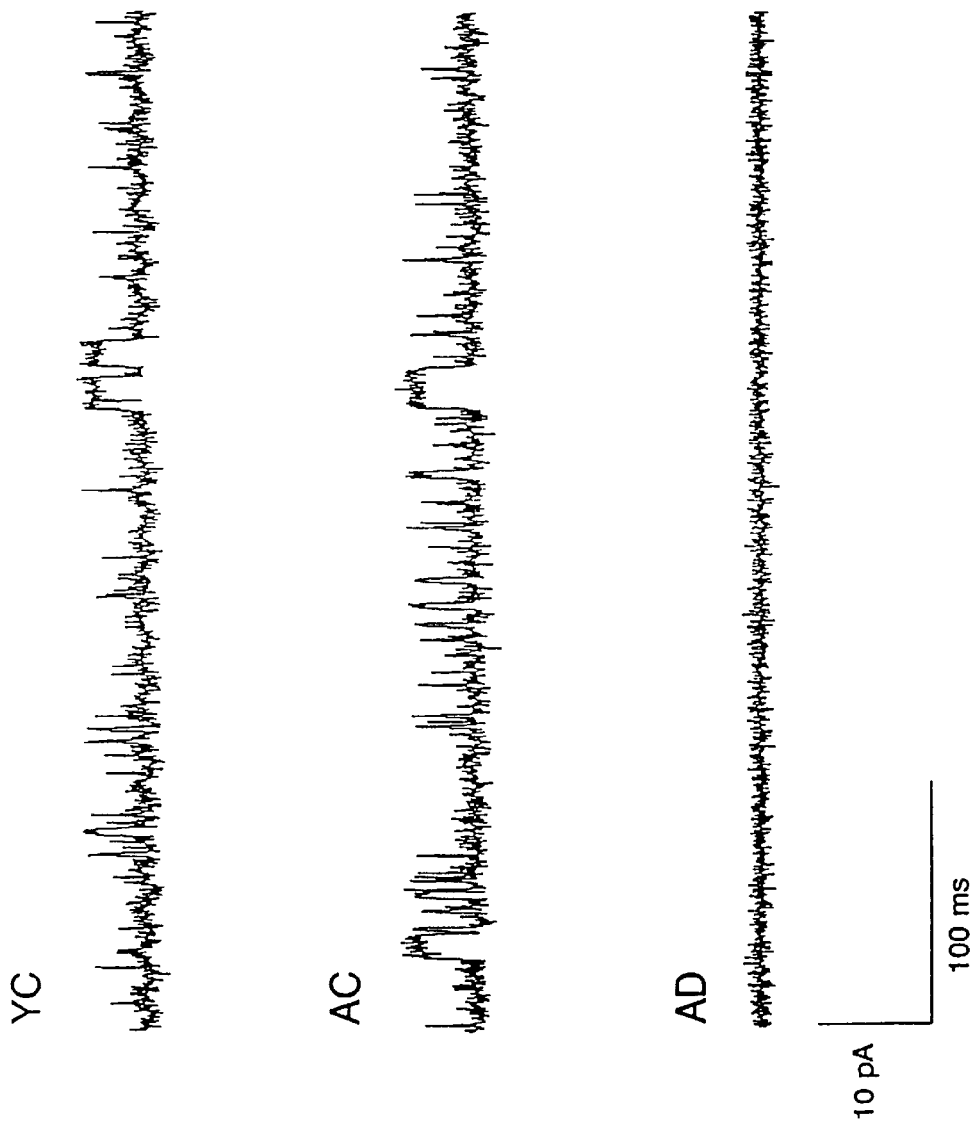

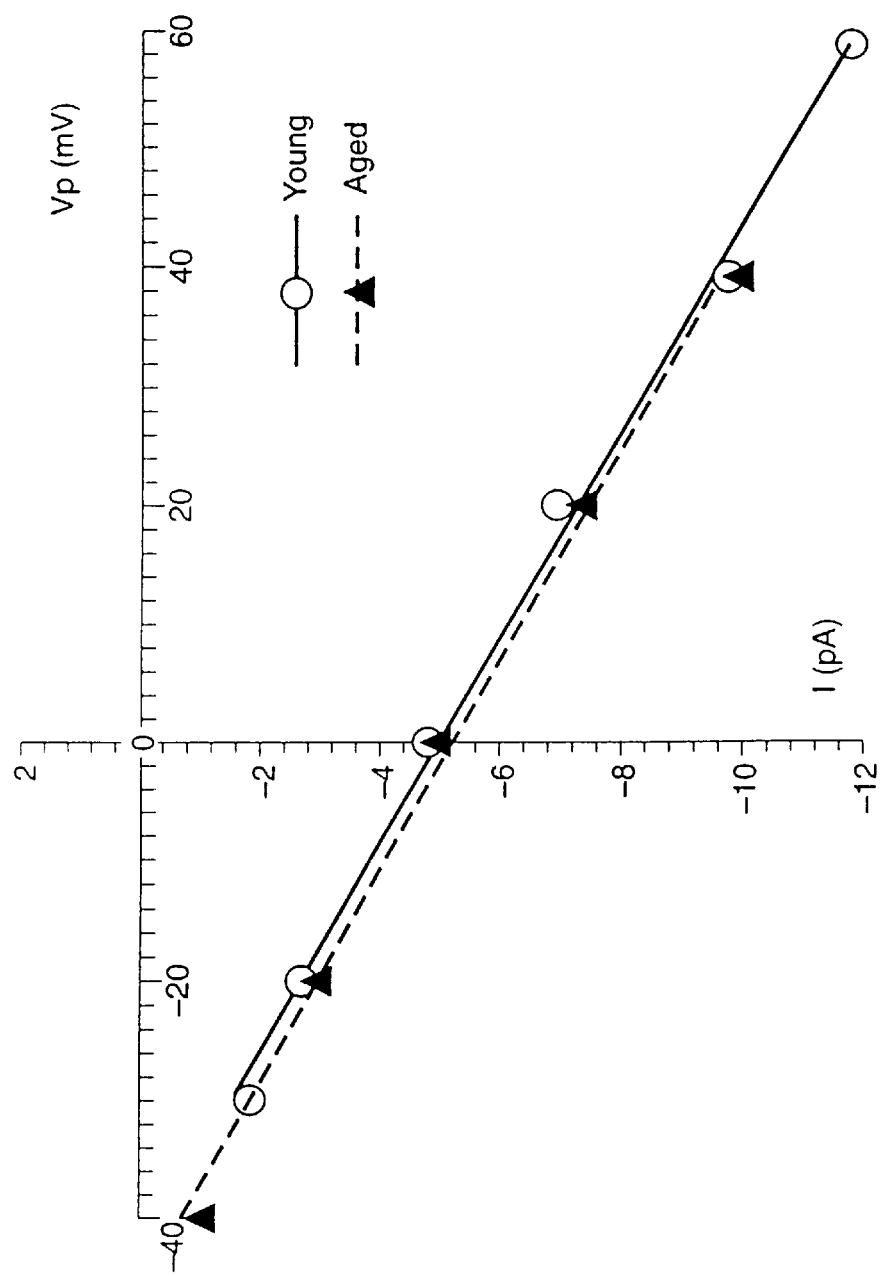

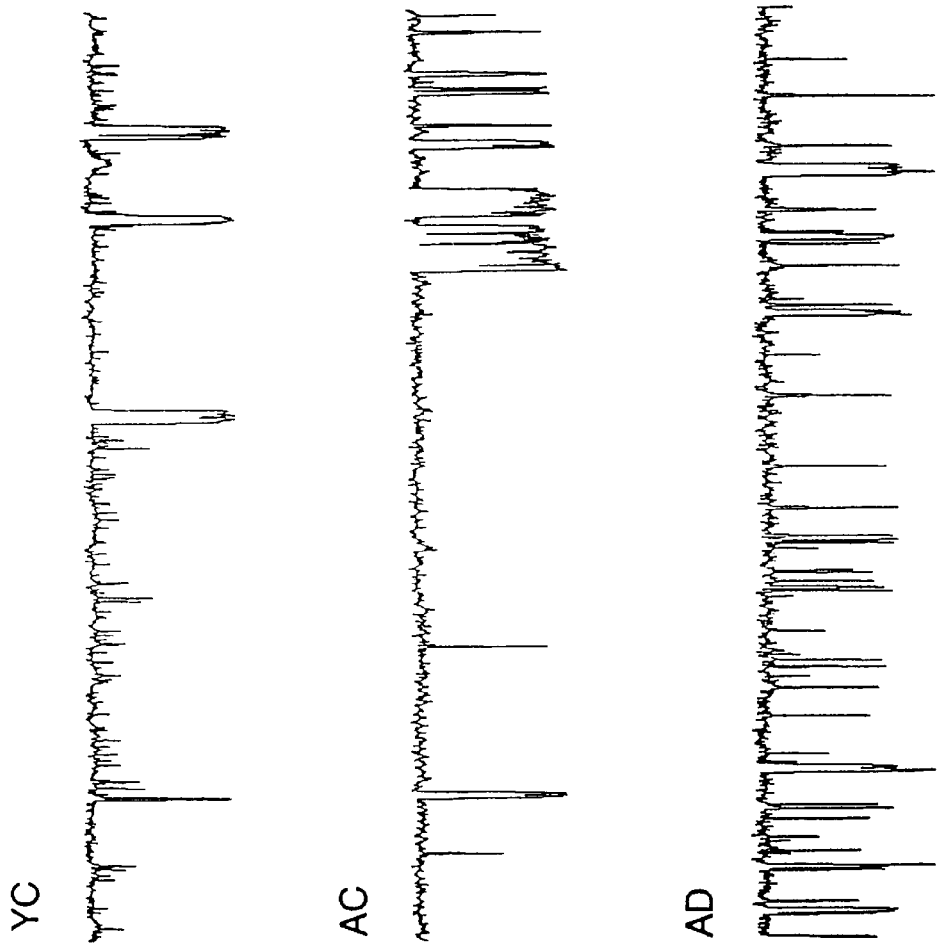

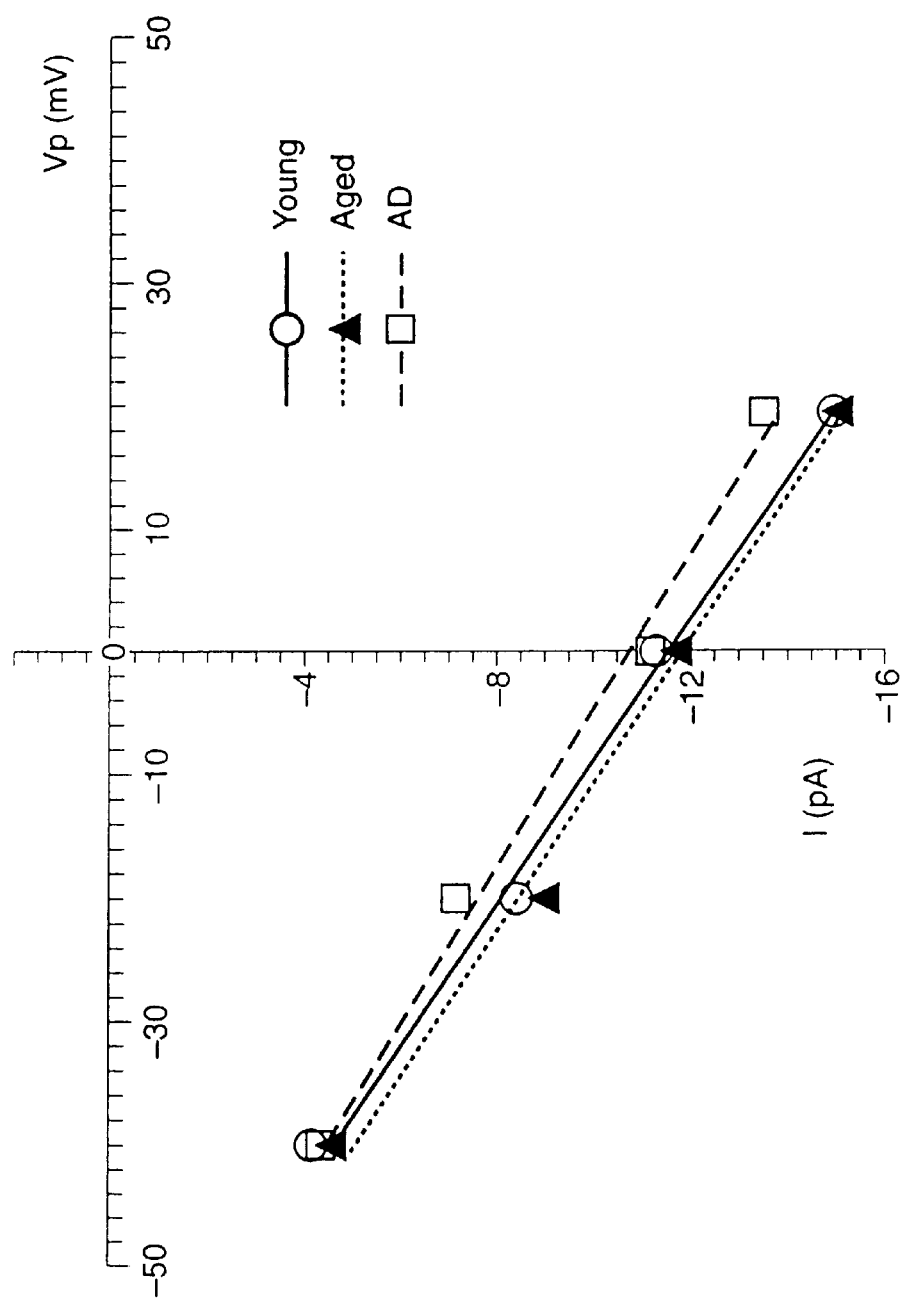

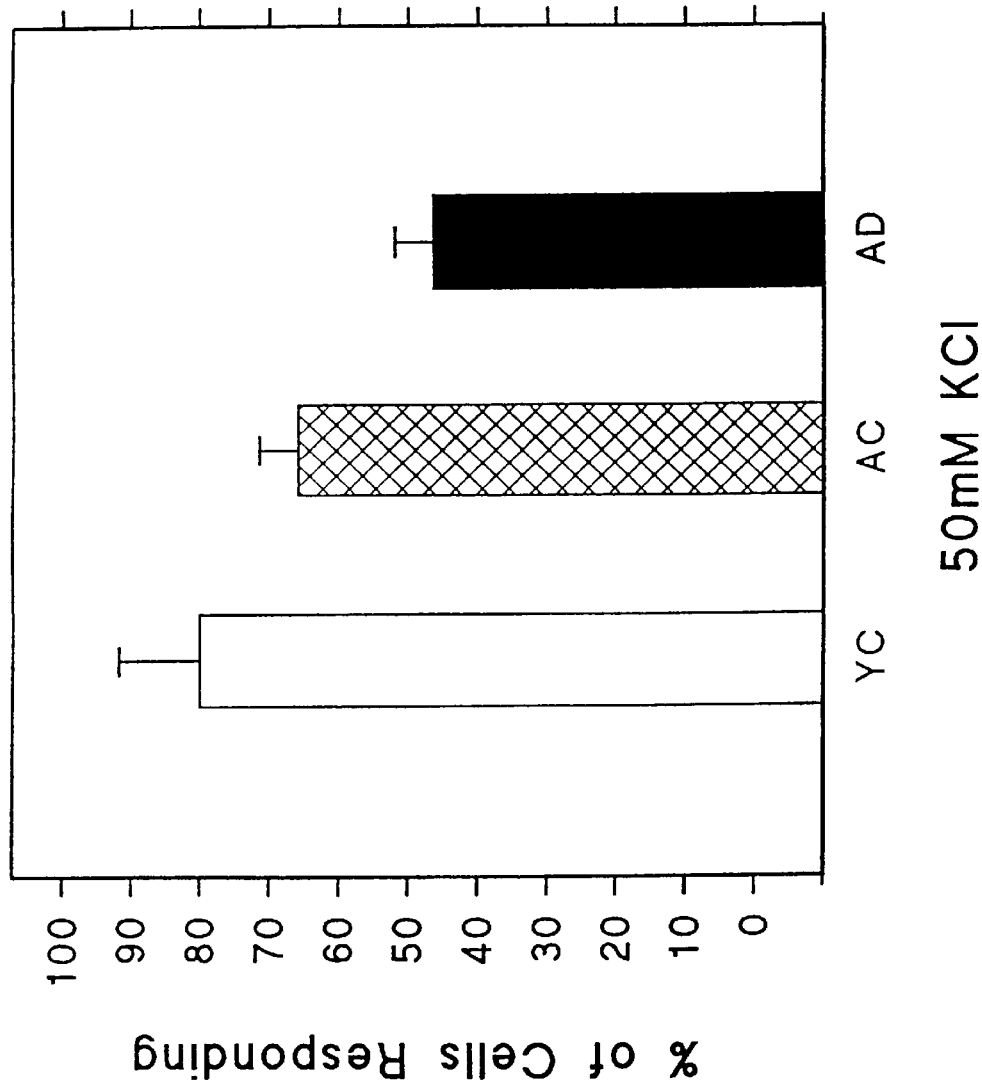

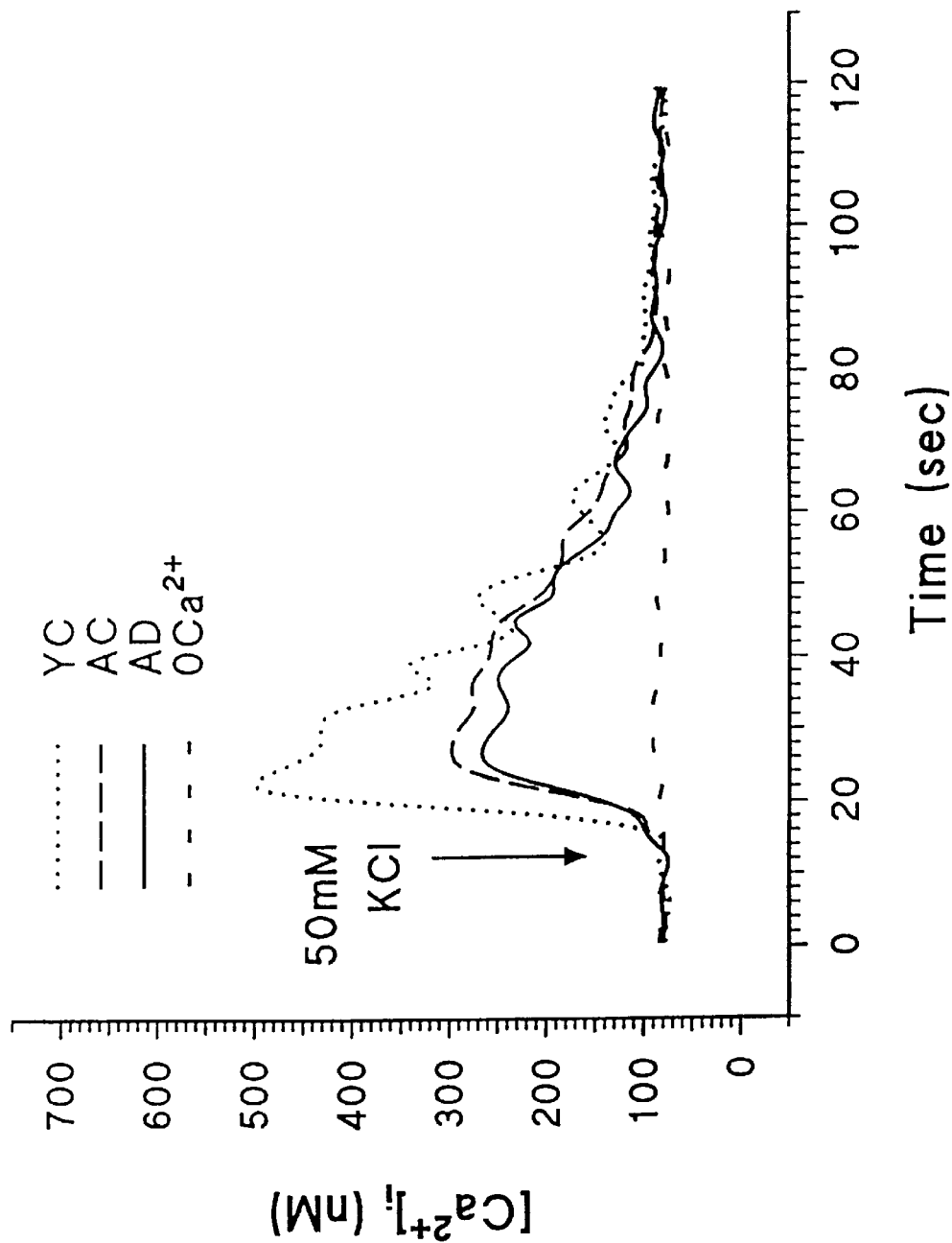

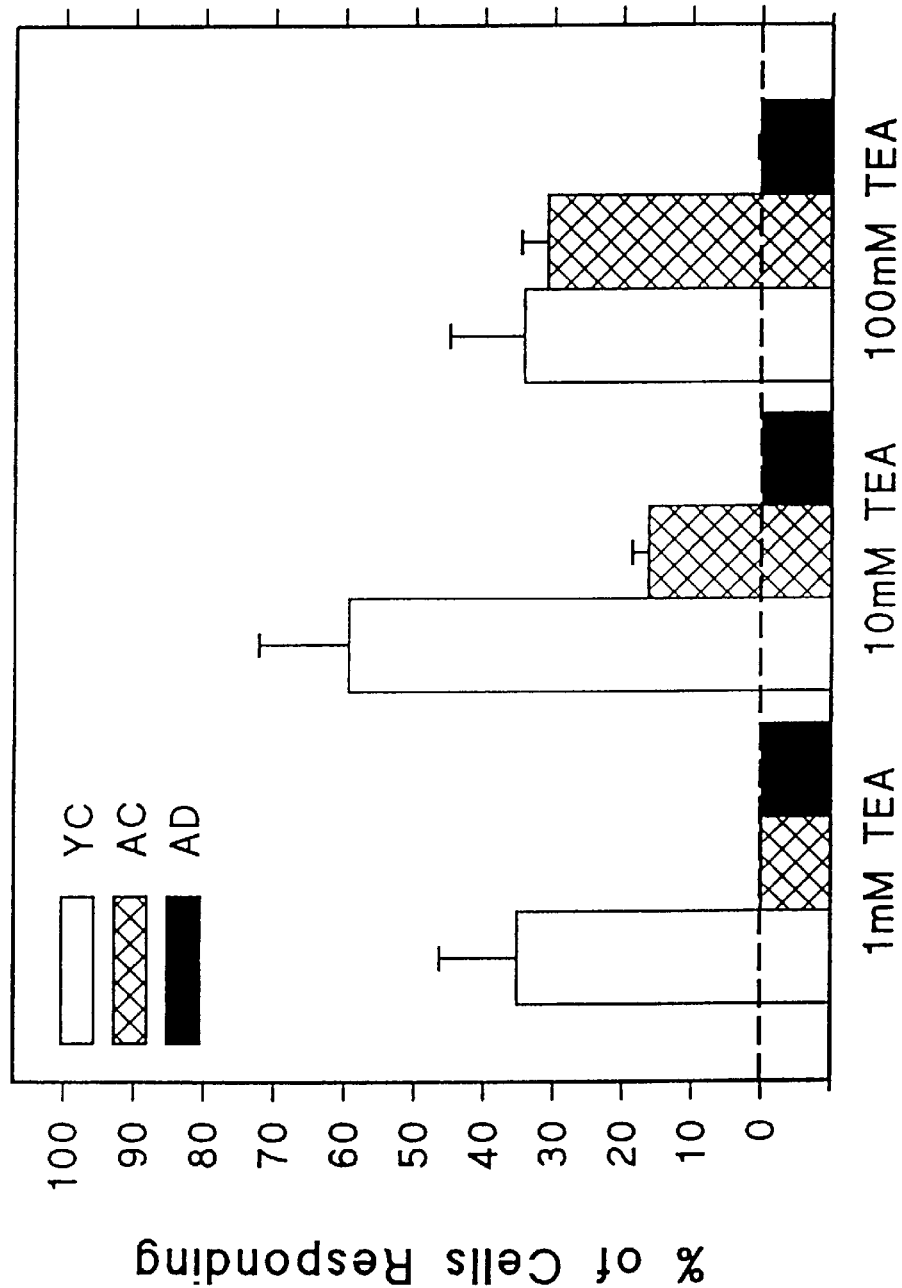

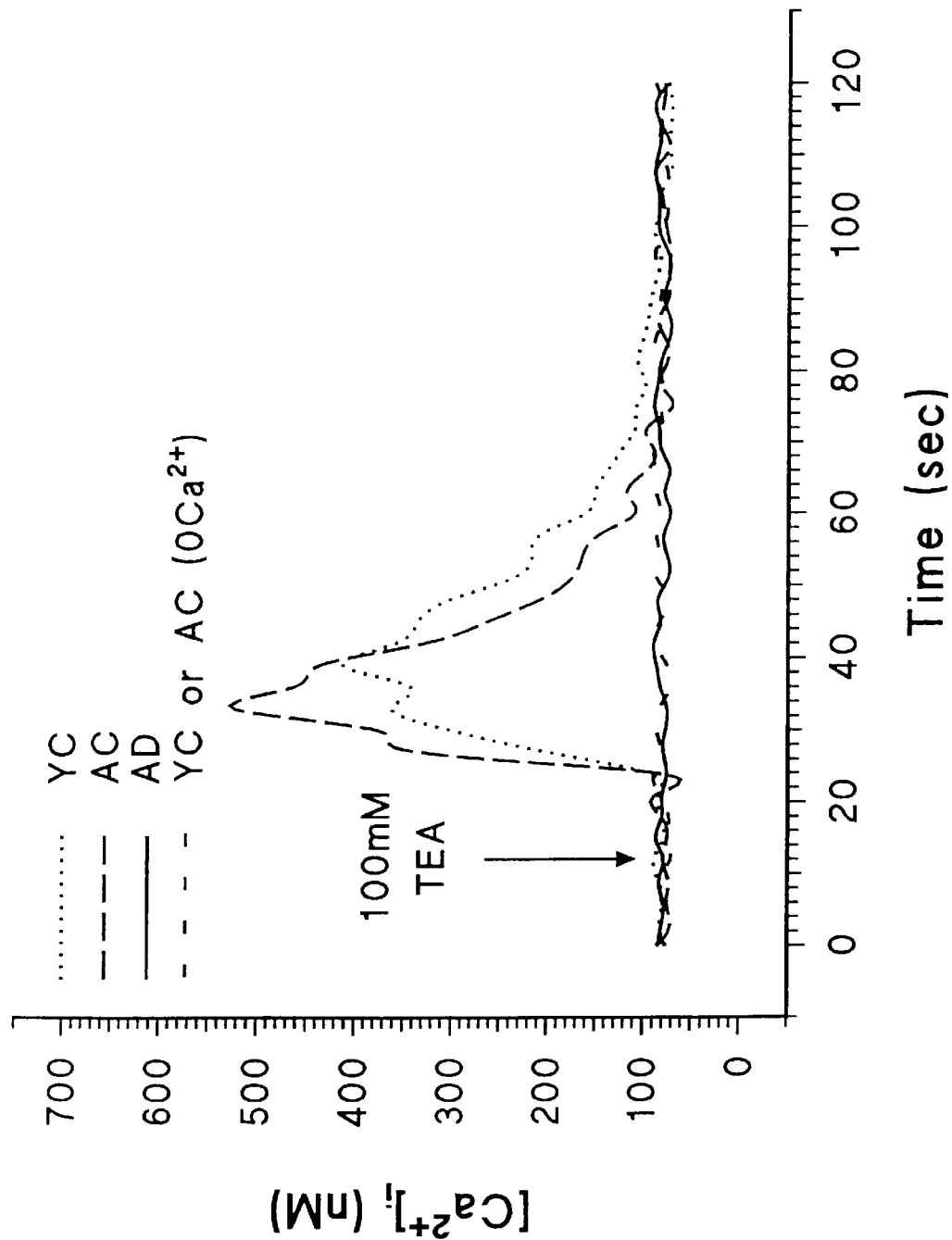

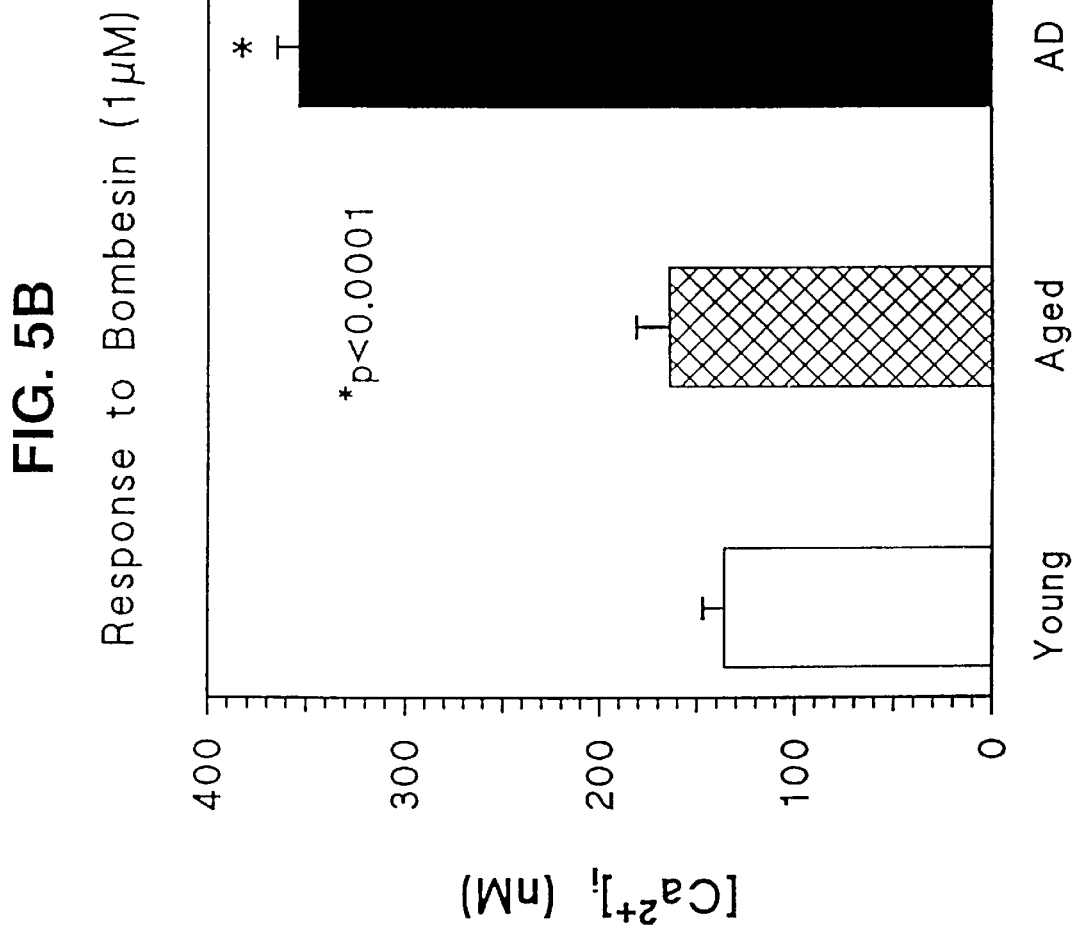

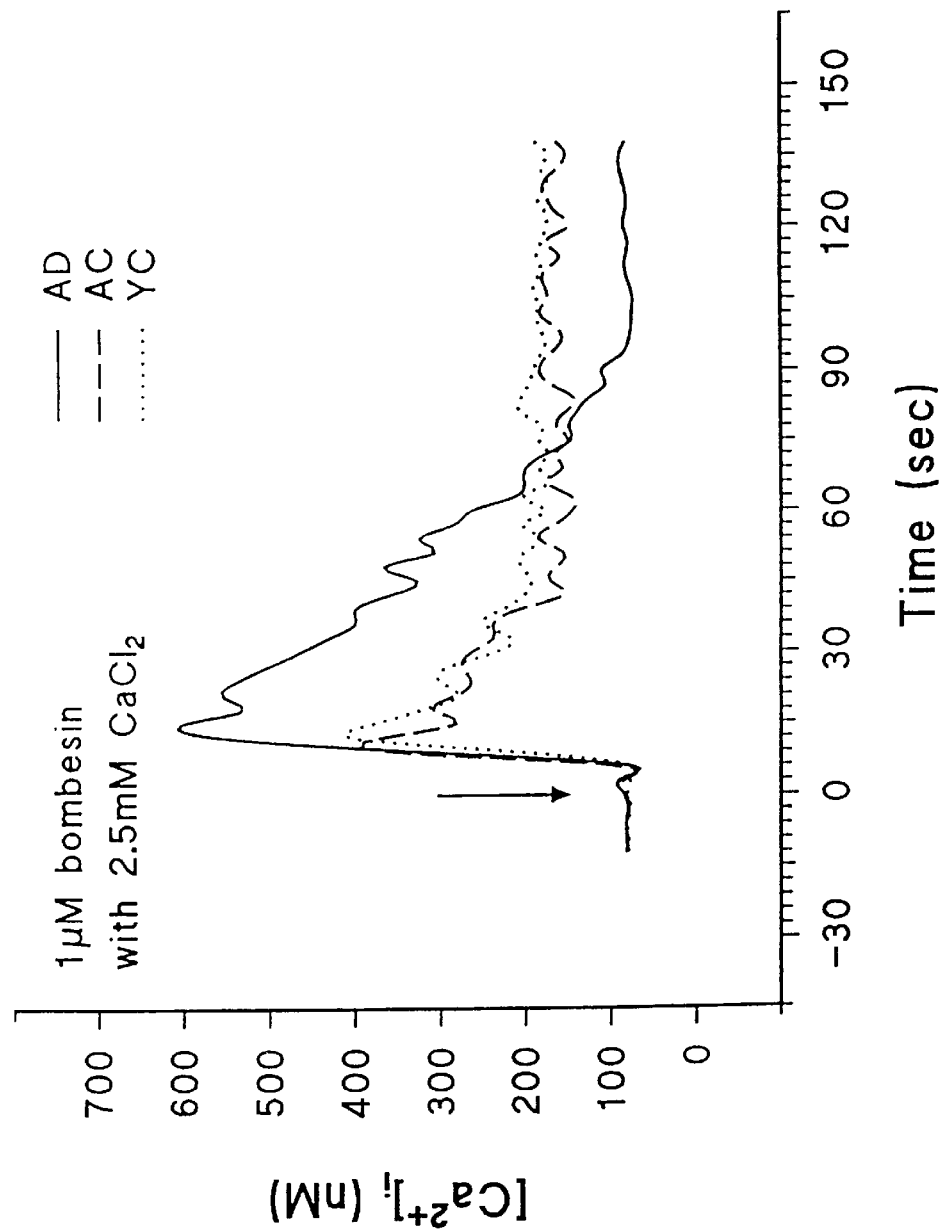

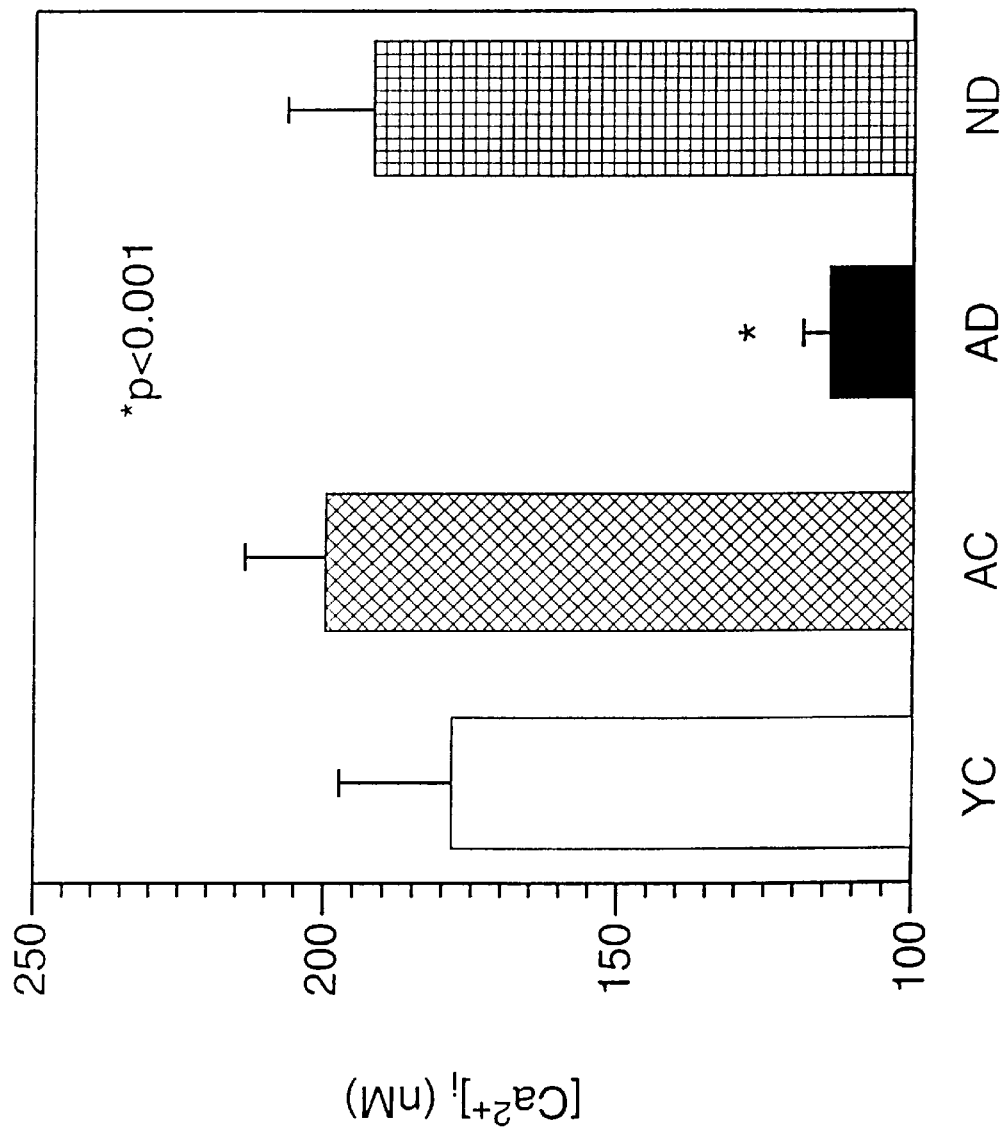

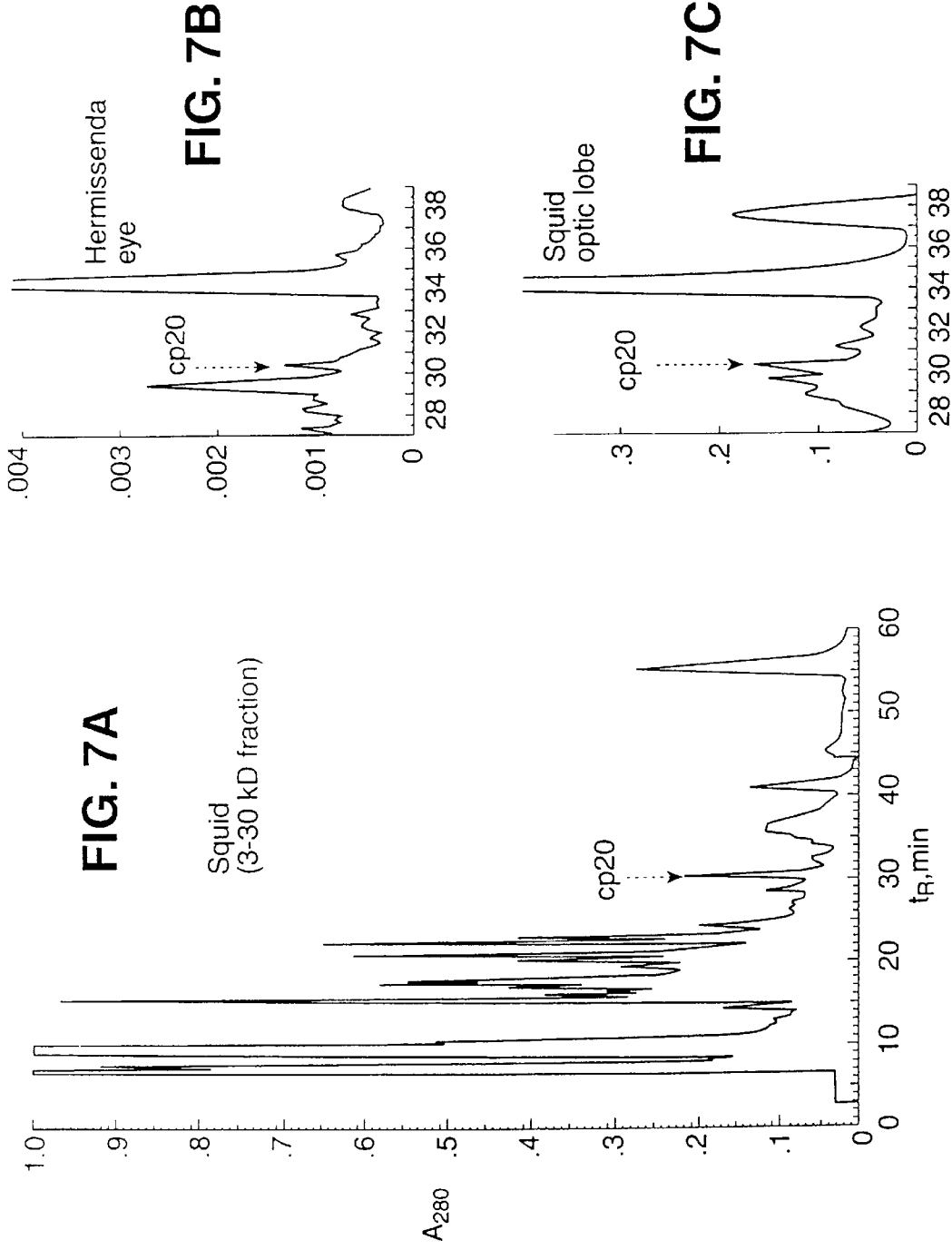

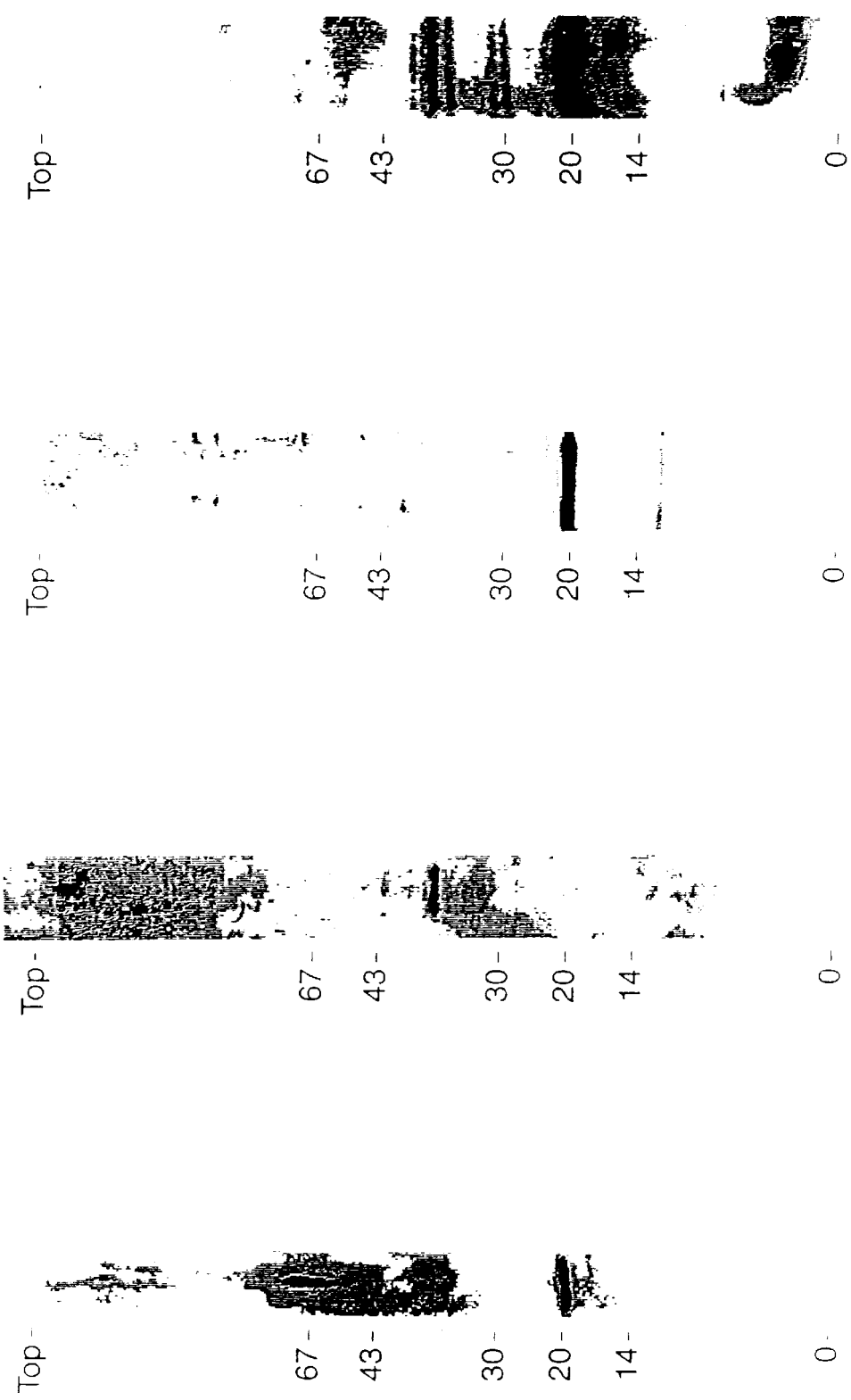

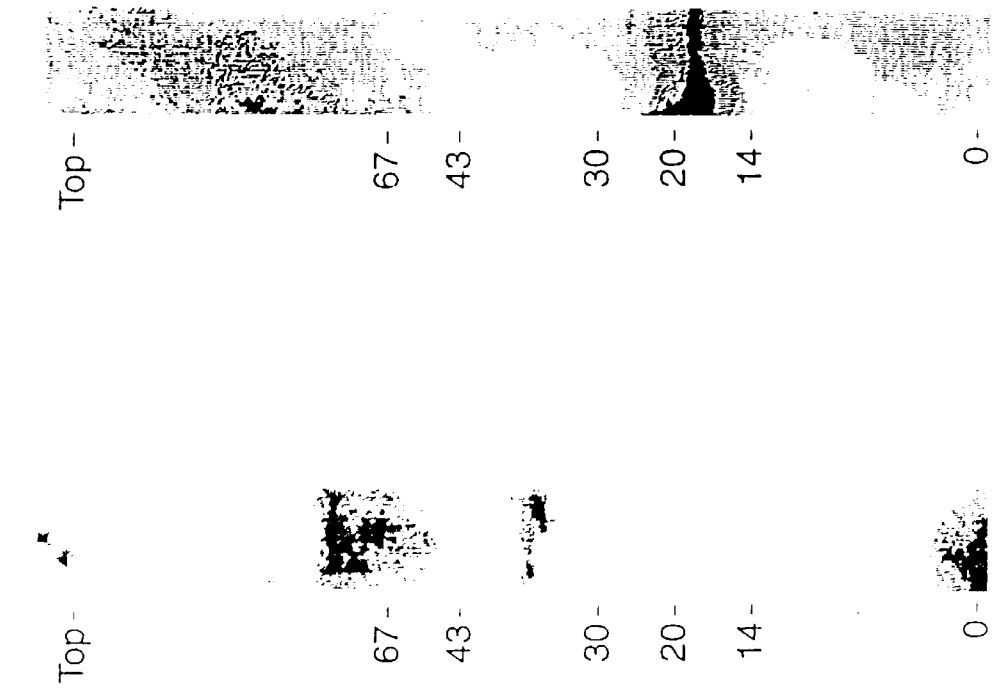
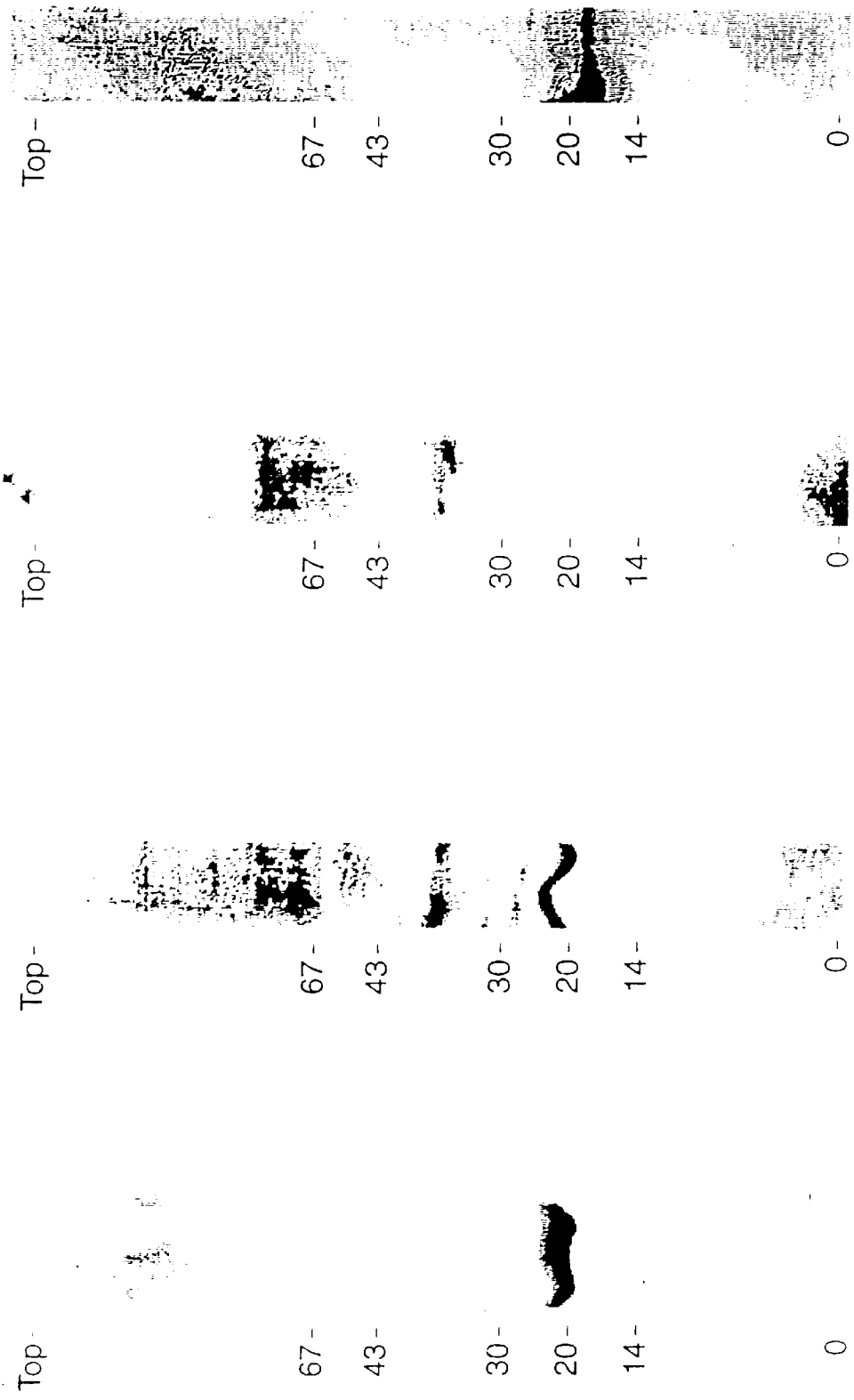

FIG. 10I
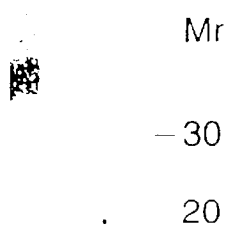
ARF
FIG. 10J
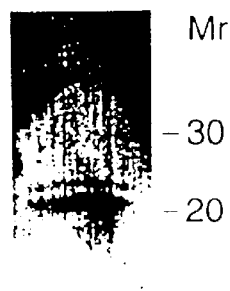
ARF
(contrasted-
enhanced)
FIG. 10K
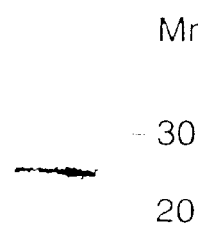
Sar1p
FIG. 10L
Mr
— 30
— 20
cp20
FIG. 14A
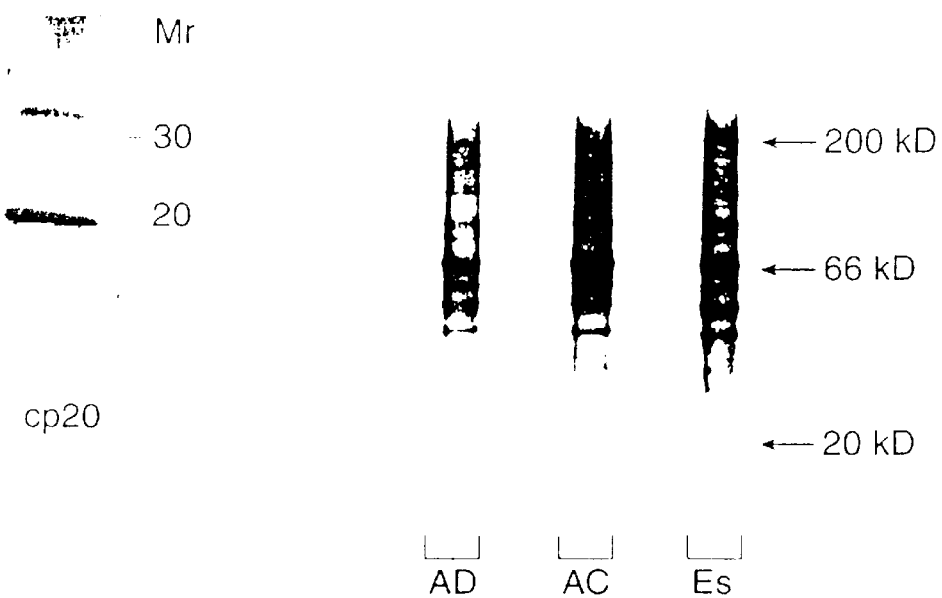
AD  AC  Es Squid cp20

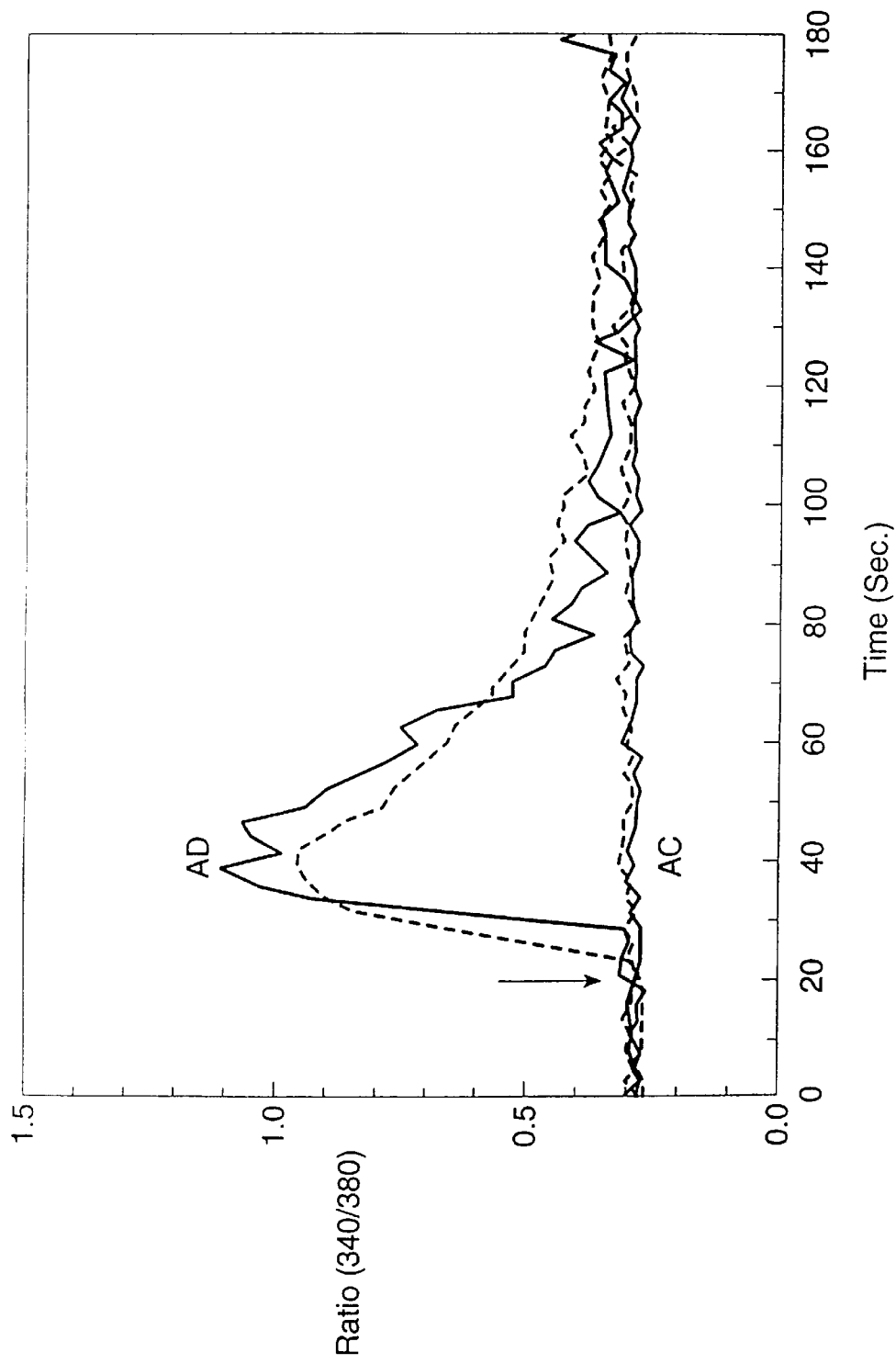

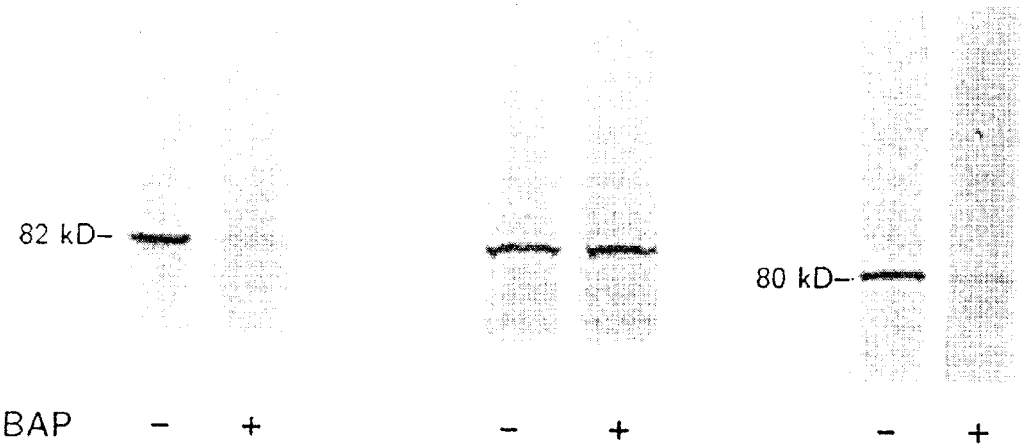

FIG. 23A
Cerebellar
2 DIV 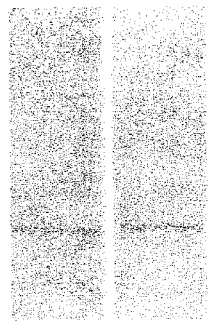 8 DIV 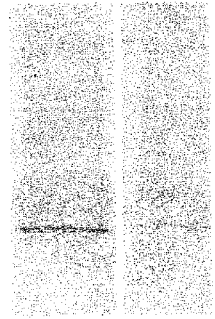
BAP  −  +      −  +
FIG. 23B
Cortical
8 DIV 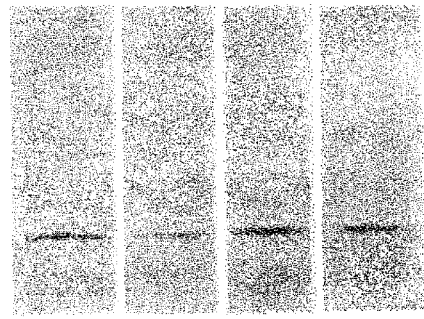
BAP  −  +  −  +
PMA  −  −  +  +

FIG. 24A

PKC α (AC)  PKC α (AD)

82 kD -

| BAP | - | + | + | - | + | + | - | + | + |
| CHX | - | - | + | - | - | + | - | - | - |
| PMA | - | - | - | + | + | + | - | - | + |

FIG. 24B

PKC γ (AD)

80 kD -

| BAP | - | + | + | + | + |
| CHX | - | - | + | - | + |
| PMA | - | - | - | + | + |

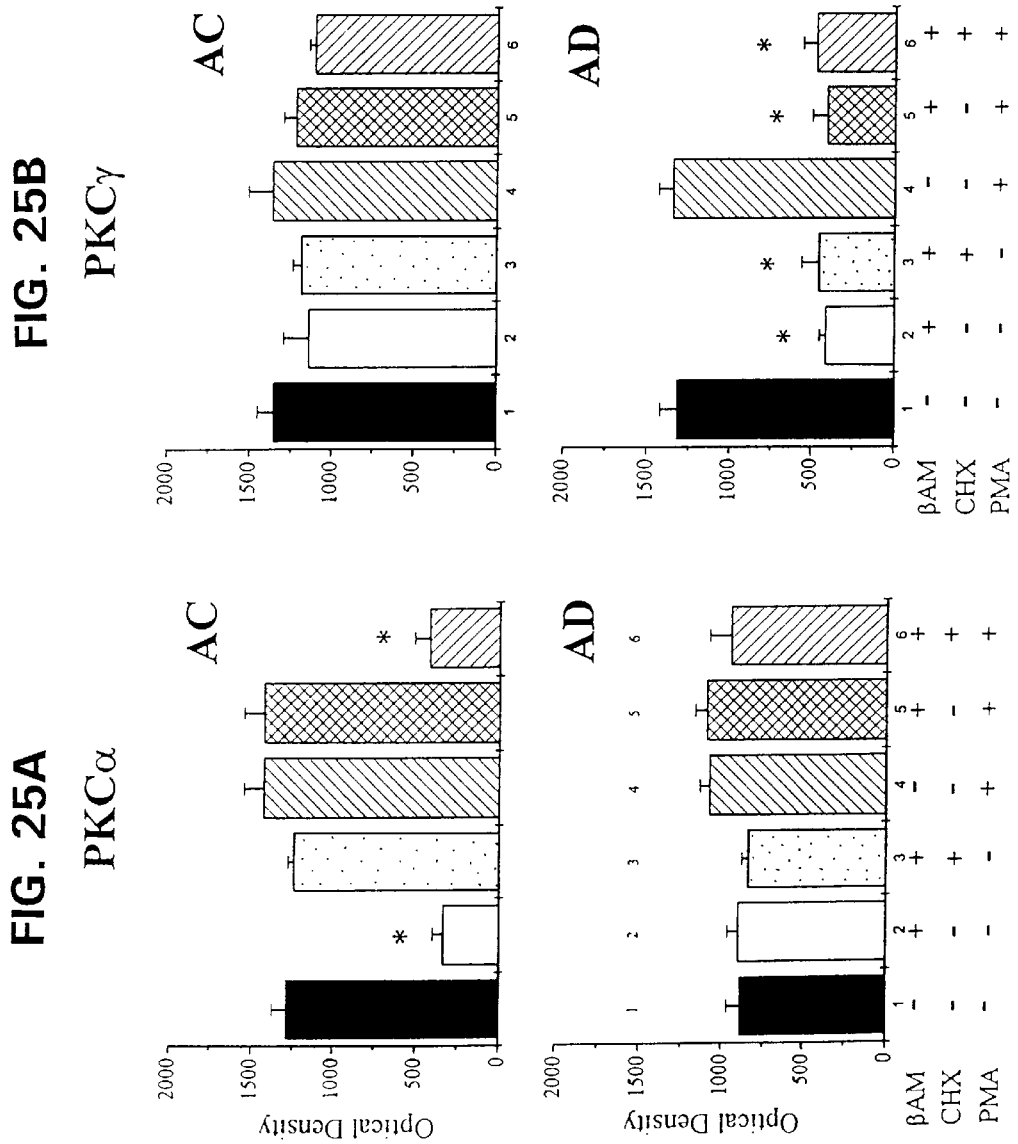

PKC $\alpha$

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 46
      (B) TYPE: AMINO ACID
      (C) STRANDEDNESS: UNKNOWN
      (D) TOPOLOGY: UNKNOWN (xi) SEQUENCE DESCRIPTION: SEQ ID NO:1:

```
Ala Arg Leu Trp Thr Glu Tyr Phe Val Ile Ile Asp Ile
 1               5                  10

Val Asn Leu Gly Tyr Asp Leu Asn Glu Thr Leu Ile Asn
        15                  20                  25

Asp Leu Leu Leu Glu Asp Ile Lys Glu Ala Leu Leu Val
                30                  35

Asp Val Asp Phe Val Asn Gln
40                  45
```

(2) INFORMATION FOR SEQ ID NO:2:

(i) SEQUENCE CHARACTERISTICS:
      (A) LENGTH: 46
      (B) TYPE: AMINO ACID
      (C) STRANDEDNESS: UNKNOWN
      (D) TOPOLOGY: UNKNOWN (xi) SEQUENCE DESCRIPTION: SEQ ID NO:2:

Arg Arg Leu Trp Lys Asp Tyr Phe Pro Glu Val Asn Gly
 1               5                  10

Ile Val Ala Leu Gly Leu Leu Asn Thr Thr Leu Lys Asn
     15                  20                  25

Asp Arg Leu Ala Lys His Gly Lys Leu Leu Phe Leu Lys
         30                  35

Asp Val Pro Phe Val Ile Leu
 40                  45

(2) INFORMATION FOR SEQ ID NO:3:

(i) SEQUENCE CHARACTERISTICS:
        (A) LENGTH:  16
        (B) TYPE:  AMINO ACID
        (C) STRANDEDNESS:  UNKNOWN
        (D) TOPOLOGY:  UNKNOWN (xi) SEQUENCE DESCRIPTION: SEQ ID NO:3:

Arg Pro Leu Trp Arg His Tyr Phe Gln Asn Thr Gln Gly
 1               5                  10

Leu Ile Phe
     15

(2) INFORMATION FOR SEQ ID NO:4:

(i) SEQUENCE CHARACTERISTICS:
        (A) LENGTH:  16
        (B) TYPE:  AMINO ACID
        (C) STRANDEDNESS:  UNKNOWN
        (D) TOPOLOGY:  UNKNOWN (xi) SEQUENCE DESCRIPTION: SEQ ID NO:4:

Lys Arg Leu Trp Lys Asp Ser Gly Val Gln Ala Cys Phe
 1               5                  10

Asn Arg Ser
     15

(2) INFORMATION FOR SEQ ID NO:5:

(i) SEQUENCE CHARACTERISTICS:
        (A) LENGTH:  16
        (B) TYPE:  AMINO ACID
        (C) STRANDEDNESS:  UNKNOWN
        (D) TOPOLOGY:  UNKNOWN (xi) SEQUENCE DESCRIPTION: SEQ ID NO:5:

Ser Ala Met Arg Asp Gln Tyr Met Arg Thr Gly Glu Gly
 1               5                  10

Phe Leu Cys
     15

(2) INFORMATION FOR SEQ ID NO:6:

(i) SEQUENCE CHARACTERISTICS:
        (A) LENGTH:  16
        (B) TYPE:  AMINO ACID
        (C) STRANDEDNESS:  UNKNOWN
        (D) TOPOLOGY:  UNKNOWN (xi) SEQUENCE DESCRIPTION: SEQ ID NO:6:

Arg Thr Ile Thr Ser Ser Tyr Tyr Arg Gly Ala His Gly
 1               5                  10

```
Ile Ile Val
    15

(2) INFORMATION FOR SEQ ID NO:7:

(i) SEQUENCE CHARACTERISTICS:
        (A) LENGTH:  16
        (B) TYPE:    AMINO ACID
        (C) STRANDEDNESS:  UNKNOWN
        (D) TOPOLOGY:  UNKNOWN (xi) SEQUENCE DESCRIPTION: SEQ ID NO:7:

Arg Thr Ile Thr Thr Ala Tyr Tyr Arg Gly Ala Met Gly
 1               5                  10

Ile Ile Leu
    15

(2) INFORMATION FOR SEQ ID NO:8:

(i) SEQUENCE CHARACTERISTICS:
        (A) LENGTH:   8
        (B) TYPE:    AMINO ACID
        (C) STRANDEDNESS:  UNKNOWN
        (D) TOPOLOGY:  UNKNOWN (xi) SEQUENCE DESCRIPTION: SEQ ID NO:8:

Lys Asp Ile Lys Leu Leu Leu Leu
 1               5

(2) INFORMATION FOR SEQ ID NO:9:

(i) SEQUENCE CHARACTERISTICS:
        (A) LENGTH:  15
        (B) TYPE:    AMINO ACID
        (C) STRANDEDNESS:  UNKNOWN
        (D) TOPOLOGY:  UNKNOWN (xi) SEQUENCE DESCRIPTION: SEQ ID NO:9:

Ala Arg Leu Trp Thr Glu Tyr Phe Val Ile Ile Asp Asp
 1               5                  10

Asp Cys
    15
```

DIAGNOSTIC TEST FOR ALZHEIMERS DISEASE

This application is a continuation-in-part of the U.S. patent application Ser. No. 08/809,646 filed Jul. 18, 1997, which is a continuation-in-part of U.S. patent application Ser. No. 08/312,202 filed Sep. 26, 1994, now U.S. Pat. No. 5,976,816 which is a continuation-in-part of U.S. patent application Ser. No. 08/056,456, filed May 3, 1993, now U.S. Pat. No. 5,580,748.

FIELD OF THE INVENTION

The present invention relates to methods for diagnosing Alzheimer's disease. The methods utilize newly discovered differences between cells from healthy donors and those with Alzheimer's disease. In one method, differences in the existence of functional potassium channels are assessed. In another method, differences in intracellular calcium levels in response to depolarization by a potassium channel blocker are assessed. In yet another method, differences in intracellular calcium levels in response to a chemical known to increase intracellular calcium levels by releasing calcium from intracellular stores are assessed. In another method, differences in the levels of a memory associated GTP-binding protein (Cp20) between cells from healthy donors and Alzheimer's patients are assessed. This invention also relates to the amino acid sequence for the Cp20 protein. In yet another method, differential effects of β-amyloid on levels of the protein kinase C isoenzymes PKCα and PKCγ in control and Alzheimer's cells are assessed. The invention further relates to another method in which differences in Europium (III) thenoyltrifluoro-acetate (Eu-TAA) fluorescence of cells from healthy donors and Alzheimer's patients are assessed following treatment of the cells with an activator of a receptor-mediated metabolic pathway. In addition, diagnostic indexes that utilize two or more of the above methods to distinguish Alzheimer's patients' cells from control non-AD cells are also provided.

BACKGROUND OF THE INVENTION

Alzheimer's disease is associated with extensive loss of specific neuronal subpopulations in the brain (Sims, N. R., et al. (1987) *Annals of Neurology* 21:451), with memory loss being the most universal symptom. (Katzman, R. (1986) *New England Journal of Medicine* 314:964). Alzheimer's disease has been linked to a genetic origin. (Schellenberg, G. D., et al. (1992) *Science* 258:668; Li, G., et al. (1991) *Psychiatric Clinics of North America* 14:267; St. George-Hyslop, P. H., et al. (1989) *Neurobiology of Aging* 10:417; St. George-Hyslop, P. H., et al. (1987) *Science* 235:885). Early-onset familial forms of the disease exhibit a genetic defect on chromosome 21. (St. George-Hyslop, P. H., et al. (1987)).

Cellular changes, leading to neuronal loss and the underlying etiology of the disease, remain unknown. Proposed causes include environmental factors, (Perl, D. P. (1985) *Environmental Health Perspective* 63:149; Katzman, R. (1986)), including metal toxicity, (Perl, D. P., et al. (1980) *Science* 208:297), defects in β-amyloid protein metabolism, (Shoji, M., et al. (1992) *Science* 258:126; Joachim, C. L. and Selkoe, D. J. (1992) *Alzheimer Disease Assoc. Disord.* 6:7; Kosik, K. S. (1992) *Science* 256:780; Selkoe, D. J. (1991) *Neuron* 6:487; Hardy, H. and Allsop, D. (1991) *Trends in Pharmacological Science* 12:383), and abnormal calcium homeostasis and/or calcium activated kinases. (Mattson, M. P., et al. (1992) *Journal of Neuroscience* 12:376; Borden, L. A., et al. (1991) *Neurobiology of Aging* 13:33; Peterson, E., et al. (1989) *Annals of New York Academy of Science* 568:262; Peterson, C., et al. (1988) *Neurobiology of Aging* 9:261; Peterson, C., et al. (1986) *Proceedings of the National Academy of Science* 83:7999).

Alzheimer's disease is well characterized with regard to neuropathological changes. However, abnormalities have been reported in peripheral tissue supporting the possibility that Alzheimer's disease is a systemic disorder with pathology of the central nervous system being the most prominent. (Rizopoulos, E., et al. (1989) *Neurobiology of Ag0ing* 10:717; Peterson (1986)).

Potassium channels have been found to change during memory storage. (Etcheberrigaray, R., et al. (1992) *Proceeding of the National Academy of Science* 89:7184; Sánchez-Andrés, J. V. and Alkon, D. L. (1991) *Journal of Neurobiology* 65:796; Collin, C., et al. (1988) *Biophysics Journal* 55:955; Alkon, D. L., et al. (1985) *Behavioral and Neural Biology* 44:278; Alkon, D. L. (1984) *Science* 226:1037). This observation, coupled with the almost universal symptom of memory loss in Alzheimer's patients, led to the investigation of potassium channel function as a possible site of Alzheimer's disease pathology and to the current invention.

The so-called patch clamp technique and improvements thereof, have been developed to study electrical currents in cells. The method is used to study ion transfer through channels. To measure these currents, the membrane of the cell is closely attached to the opening of the patch micropipette so that a very tight seal is achieved. This seal prevents current from leaking outside of the patch micropipette. The resulting high electrical resistance across the seal can be exploited to perform high resolution current measurements and apply voltages across the membrane. Different configurations of the patch clamp technique can be used. (Sakmann, B. and Neker, E. (1984) *Annual Review of Physiology* 46:455).

Currently, there is no laboratory diagnostic test for Alzheimer's disease. Therefore, there is a great need for a method to rapidly and clearly distinguish between Alzheimer's patients, normal aged people, and people suffering from other neurodegeaerative diseases, such as Parkinson's, Huntington's chorea, Wernicke-Korsakoff or schizophrenia. Although some investigators have suggested that calcium imaging measurements in fibroblasts were of potential clinical use in diagnosing Alzheimer's disease (Peterson et al. 1986, 1988, supra), other researchers using similar cell lines and techniques, have shown no difference in calcium levels in Alzheimer's and normal control fibroblasts. (Borden et al. 1991, supra). Thus, the latter work refutes the findings of the former work.

The two proteins most consistently identified in the brains of patients with Alzheimer's disease have been β-amyloid and tau, whose roles in the physiology or pathophysiology of brain cells are not fully understood. However, there has been no diagnostic nor prognostic laboratory tests for Alzheimer's disease involving these or other proteins. Further, few otter proteins have been identified which have physiological implications for Alzheimer's disease.

The methods for diagnosing Alzheimer's disease of the present invention using cells isolated from patients are needed and will greatly improve the now very complicated clinical diagnostic process for Alzheimer's disease. These methods are especially important because they are able to distinguish patients with Alzheimer's disease from patients with other neurodegenerative diseases.

SUMMARY OF THE INVENTION

The invention provides methods for assaying for Alzheimer's disease using cells isolated from patients. In one embodiment of the invention, the presence or absence of a particular potassium channel is measured. In a cell from a healthy control, potassium channels with slope conductances of 113 pS (picosiemens) and 166 pS are present and functional. In Alzheimer's cells, the 113 pS potassium channel is missing or nonfunctional.

In a second embodiment of the present invention, the effect of potassium channel blockers specific for the 113 pS potassium channel on intracellular calcium levels is assessed. In this method, intracellular calcium levels are found to be elevated in response to potassium channel blockers in normal cells, but not in cells from donors with Alzheimer's disease. The preferred potassium channel blocker is tetraethylammonium ("TEA") at a final extracellular concentration of 100 mM. However, other potassium channel blockers which specifically block the 113 pS potassium channel may also be used. Furthermore, when TEA is used, other final concentrations of TEA may be used as long as the level of TEA causes intracellular calcium levels to be elevated in normal cells, but not in cells from donors with Alzheimer's disease.

In a third embodiment of the invention, sample cells from a patient are contacted with an activator of intracellular calcium release, in ar, amount sufficient to release calcium from intracellular storage sites, and the resulting increase in intracellular calcium levels is measured. In this embodiment, both normal cells and cells from Alzheimer's patients exhibit an increase in intracellular calcium; however, the increase in Alzheimer's patients is much greater. When an inositol-1,4,5,-triphosphate ($IP_3$) activator is used to increase intracellular calcium levels, the preferred embodiment utilizes bombesin added to a final extracellular concentration of 1 $\mu$m. However, other final concentrations can be used.

As shown in the examples, the combination of the second and third embodiments of the invention can be used in series to provide a very accurate method of diagnosing AD, with no false positives or false negatives. Furthermore, these methods are able to distinguish patients with Alzheimer's disease from patients with other neurodegenerative diseases. Cells from patients with Parkinson's disease, schizophrenia, Huntington's chorea, and Wernicke-Korsakoff exhibit responses of normal cells when treated with either TEA or bombesin.

In a fourth embodiment of the invention, the level of the memory associated GTP-binding protein (Cp20) in cells from an Alzheimer's disease patient is assessed. In this method, the Cp20 protein levels are found to be significantly reduced in cells from Alzheimer's disease patients relative to cells from healthy controls. Cp20 protein levels are also reduced in the cells of close relatives of the Alzheimer's disease (patients, suggesting a prognostic use for this assay as well.

It is not known at the present time if the defects detected by the methods of this invention appear prior to or concurrently with the clinical onset of Alzheimer's disease. However, if the former is true, it is anticipated that the methods of this invention will have predictive as well as diagnostic utility in the detection of Alzheimer's disease.

The present invention also provides a partial amino acid sequence for the Cp20 protein. Therefore, this invention also extends to products derived using the amino acid sequence and useful for carrying out the Cp20 diagnostic assay, such as nucleic acid probes, or monoclonal or polyclonal antibodies reactive with the Cp20 protein.

This invention also extends to kits comprising products useful for carrying out the Cp20 diagnostic assay such as DNA probes, antibodies, kits and the like.

In another embodiment of the invention, the differential effects of $\beta$-amyloid protein on levels of protein kinase C (PKC) isoenzymes in Alzheimer's cells relative to cells from healthy controls can be used as an diagnostic assay. In this method, treatment with $\beta$-amyloid protein induces a significant decrease in levels of the PKC$\alpha$ isozyme, but not the PKC$\gamma$ isozyme, in cells from a healthy donor, whereas in Alzheimer's cells, a significant reduction in levels of PKC$\gamma$, but not PKC$\alpha$, was observed after $\beta$-amyloid treatment.

In a further embodiment of the invention, differences in the Eu-TAA fluorescence intensity of cells from healthy donors and from Alzheimer's patients are assessed following treatment of the cells with an activator of receptor-mediated metabolic pathways such as bradykinin.

In yet another embodiment of this invention a diagnostic index utilizing two or more of the diagnostic tests described herein is provided that increases the probability of distinguishing AlzheLmer's patient cells from non-AD cells.

BRIEF DESCRIPTION OF THE FIGURES

FIGS. 1A–1B. 113 pS channel. (1A). Cell attached recordings from Alzheimer and control fibroblasts. A potassium channel cf ~4.5 pA unitary current size (0 mV pipette potential), with identical kinetics appeared in age-matched control (AC) and young controls (YC) fibroblasts, but was entirely absent in the recording of AD fibroblasts (1A, bottom) Downward deflections represent the open state. (1B). I/V relationships and slope conductances. I/V relationships and slope conductances (determined by linear regression) were almost identical within the voltage range explored, 113.2±0.9 pS (mean±S.D., n=8) for YC and 112.9±3.2 pS (n=7) for AC fibroblasts.

FIGS. 2A–2B. 166 pS channel. (2A). Cell attached recordings from Alzheimer and control fibroblasts. A second channel (166 pS) was recorded under the same conditions from fibroblasts of all three groups (AD, YC and AC). (2B). I/V relations and slope conductances. I/V relations as well as slope conductances [YC=174±5.7 pS, n=4; AC=169.2±2.8 pS, n=4; AD=157.6±4.7 pS, n=6 (Mean±S.D.)] were approximately the same across groups. Membrane potential was similar in control (−42.6±5.4, Mean±S.D., n=7) and in AD (−45.4±6.9, n=3) fibroblasts.

FIGS. 3A–3C. (3A) and (3B). Percent of cells responding to the addition of 50 mM potassium chloride and average $[Ca^{2+}]_i$ (nM) of responding cells. High potassium-induced depolarization caused $[Ca^{2+}]_i$ elevation (at least 100% increase) in all three groups (AD N=13 cell lines; AC N=10, YC N=6). The proportion of responding cells and the $[Ca^{2+}]_i$ peak values were significantly higher in YC (n=183 cells) fibroblasts ($\chi^2$=14.22, p<0.001), as compared to AC (n=299) and AD (n=268) fibroblasts (3A and 3B). (3C). Sample traces of time courses of the $Ca^{2+}$ response in cells after the addition of 50 mM KCl. The $[Ca^{2+}]_i$ peak occurs 10 to 15 seconds after stimulation, returning to basal levels after 100 seconds. No responses were observed if external $[Ca^{2+}]$ was lowered ["nominally $Ca^{2+}$ free" solution, 5 mM EGTA was added (estimated free $Ca^{2+}$=0.04 $\mu$M)], or $Ca^{2+}$ channel blickers (0.1 mM $LaCl_3$, 10 mM $CoCl_2$, 10 mM $NiCl_2$, 10 mM $CdCl_2$ or 10 pM nifedipine) were added before stimulation ("0 Ca2+").

FIGS. 4A–4C. $[Ca^{2+}]_i$ elevation in response to TEA. (4A) Percentage of cells responding to the addition of TEA and (4B) Average $[Ca^{2+}]_i$ response in the cells after TEA treatment. 1 nM TEA application elevated $[Ca^{2+}]_i$ in YC fibroblasts (n=130 cells) but not in AC (n=184) or AD fibroblasts (n=195). 10 mM TEA elevated $[Ca^{2+}]_i$ in YC (n=176 cells), AC (n=231), but not in AD (n=204) fibroblasts ($\chi$ 134.00, p<0.001). Similarly, 100 mM TEA elevated $[Ca^{2+}]_i$ in YC (n=532 cells), AC (n=417), but not in AD (n=738) fibroblasts, $\chi^2$ 231.44, p<0.001 (also see Table 2). Basal $[Ca^{2+}]_i$ levels were virtually the same (S.E.<2 nM), therefore, standard error bars are not distinguishable from the bar representing the arithmetic mean for those groups. (4C). Time course of $Ca^{2+}$ responses. The $[Ca^{2+}]_i$ peak occurs 20 to 30 seconds after 100 mM TEA addition in YC and AC fibroblasts, returning to basal levels after 100 seconds. Notes that no response meeting criterion (10% of cells in a line with $\geq$100% elevation) was observed in AD cells. Similarly, the response was absent in control cells when external $[Ca^{2+}]$ was lowered.

FIGS. 5A–5B. (5A). $Ca^{2+}$ mobilization induced by 1 μm bombesin in the absence of extracellular calcium. (BB). $Ca^{2+}$ responses at 42 sec after 1 μM bombesin application. The $[Ca^{2+}]_i$ levels in Al) cells are much larger than in AC and YC cells. The numbers of cell lines (N) are 9, 8 and 6 for AD, AC and YC, respectively. The values are means±S.E.M.

FIGS. 6A–6B. (6A). $Ca^{2+}$ responses induced by 1 μm bombesin in the presence of extracellular calcium. 1 μm bombesin elicited a fast peak of $[Ca^{2+}]_i$, followed by a sustained phase for YC and AC cells, but not for AD cells, in the presence of extracellular 2.5 mM $CaCl_2$. The arrow indicates drug application. (6B). Bar graph illustrating differences evident 90 seconds after bombesin application. In the presence of normal extracellular calcium (2.5 mM), a sustained calcium entry follows the initial bombesin response in control cells but is completely absent in AD fibroblasts. The difference evident 90 seconds after bombesin application is shown and has a significance level of p<0.001.

FIGS. 7A–7D. $A_{280}$ HPLC tracings of proteins from Hermissenda eye (7B), squid optic lobe (7C) and squid 3–30 kDa fraction (7A). 36 eyes from Hermissenda trained to associate light rotation, or 1/10 squid optic lobe were analyzed by anion exchange HPLC as described in the text. In unconditioned Hermissenda, the cp20 peak (arrow) is 3–4 times smaller than the cp20 peak from conditioned animals shown here. (7D) Correlation curve of $t_R$'s from HPLC tracing from squid optic lobe proteins vs. $t_R$'s (retention times) from reference chromatogram of proteins from trained Hermissenda eye.

Supernatant from 10 Hermissenda CNEs was applied to an AX-300 column. Each fraction was blotted, reacted with mouse anti-cp20 and developed with AP (alkaline phosphatase)/BCIP (bromo-4 chloro-3-indolyl phosphate).

The blot was scanned, converted to O.D., and integrated by computer. The large peak at 31 min coincided with the cp20 peak in the $A_{280}$ profile.

FIGS. 10A–10L. (10A, 10B) Interconversion of the 20 kDa and 40 kDa forms of cp20 by DTT. Cp20 purified by anion-exchange HPLC in the absence of DTT was fractionated on a non-denaturing gel. The 40 kD region of the gel was eluted, reacted with DTT (10A) or water (10B), and analyzed by SDS-PAGE. (10C) SDS gel of purified squid cp20. (10D–10G) Western blots of squid supernatant (10D), Hermissenda supernatant (10E), and rabbit hippocampus particulate (10F) and supernatant fraction (10G), reacted with anti-cp20 monoclonal AB. (10H) Western blot of is cross-reaction of purified squid cp20 with anti Gin. (Staining: 10A–10C, CG (colloidal gold); 10D–10G, AP/BCIP; 10H–10L, Horseradish peroxilase (HRP)/ diaminobenzidine (DAB). (10I–10L) Western blots of (10I, 10J), ARF (10K) yeast Sarlp, and (10L) squid cp20 reacted with anti-cp20 polyclonal antibody (Staining: HRP/DAB). (10J) has been contrast-enhanced to more clearly show the ARF band in (10I).

Figure 11A:
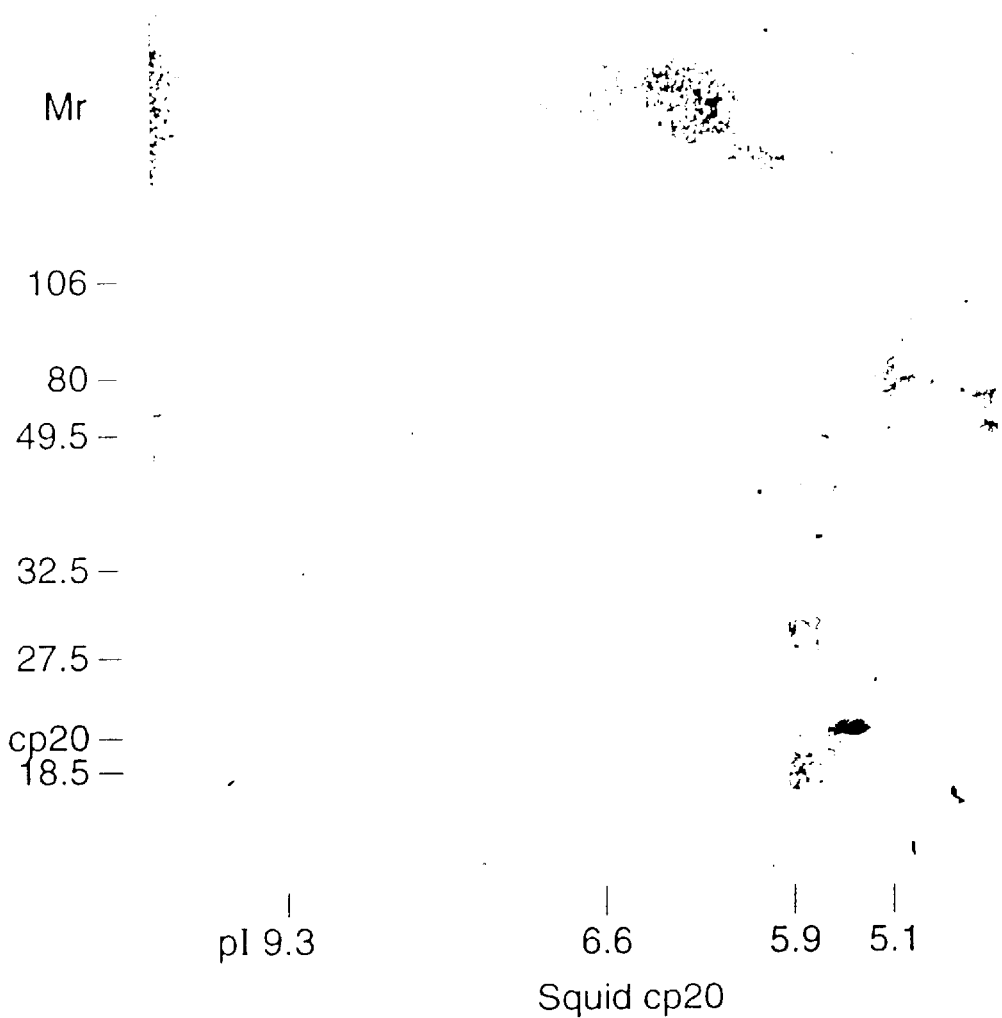
Figure 11B:
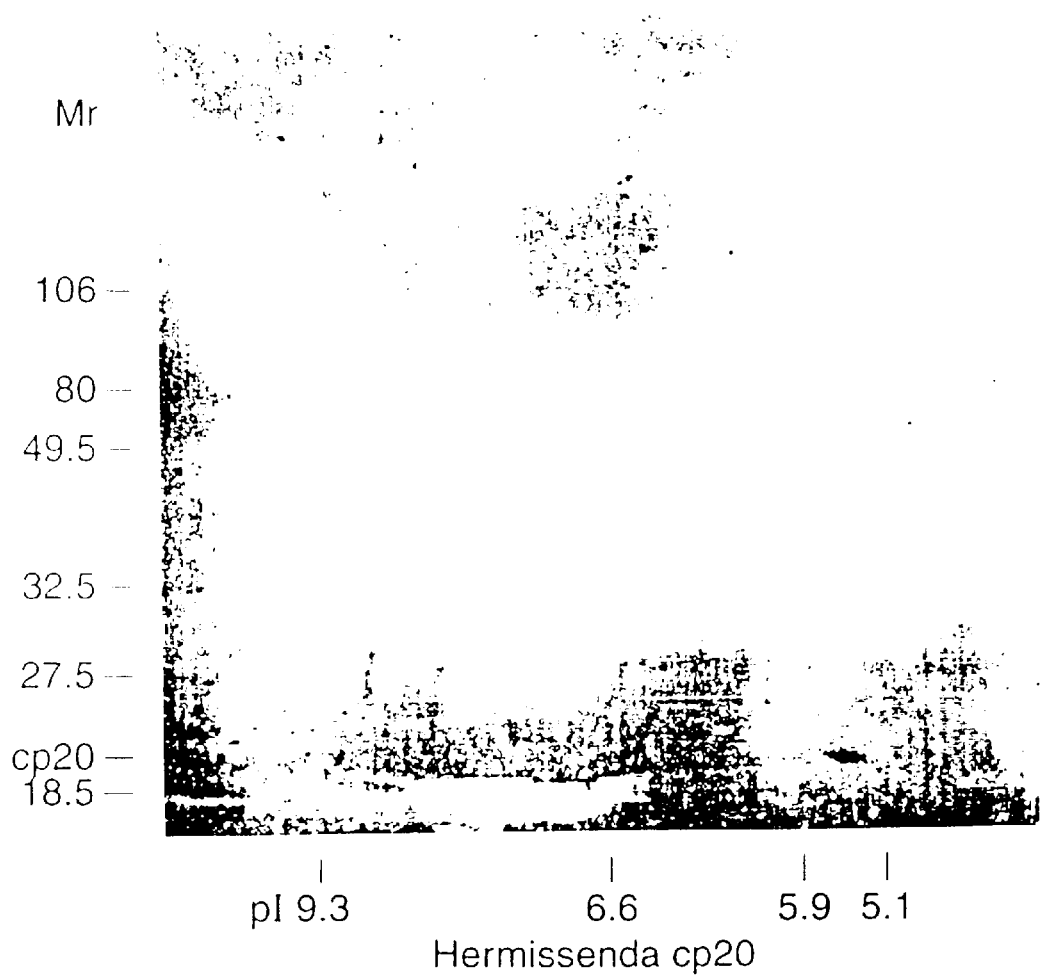

FIGS. 11A–11B. 2D gel of squid cp20 (11A) and Hermissenda cp20 (11B), purified in the presence of DTT (colloidal gold stain).

Figure 12A:
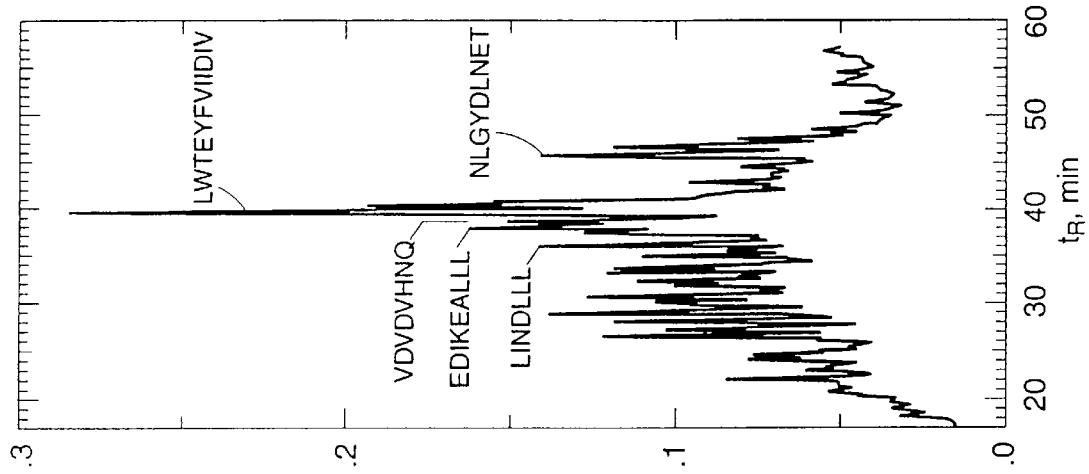
Figure 12B:
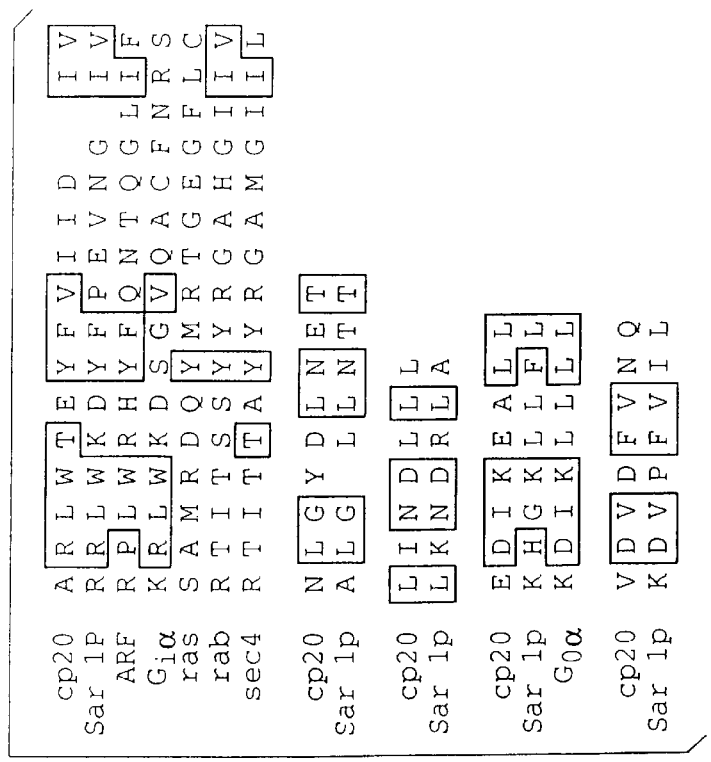

FIGS. 12A–12B. (12A) Sequence of cp20 (SEQ. ID. NO. 1) tryptic peptides and other proteins. The top sequence is a consensus of sequences of the same peptide from three different batches of cp20. The corresponding regions in the Gia (SEQ. ID.NO. 4) (Michel T., et al. (1986) *Proc. Nat. Acad. Sci.* USA 7663–7667.), ras (SEQ. ID. NO. 5) (Santos E., Nebreda A. R. (1989) *FASEB J.* 3, 2151–2163.), rab (SEQ. ID. NO. 6) (Zahraoui A., et al. (1989) *J. Biol. Chem.* 264, 12394–12301.), sec4 (SEQ. ID. NO. 7) (Salminen A., Novick P. J. (1987) *Cell* 49, 527–538.), and Drosophila Goα (SEQ. ID. NO. 8) sequence (Schmidt C. J., et al. (1989) *Cell Regul.* 1, 125–134.) are shown. (12B) RP-HPLC $A_{214}$ profile of a tryptic digest of cp20.

FIGS. 13A–13D. Western blot analyses of Cp20. (13A) Western blot of monoclonal anti-Cp20 reaction with Cp20 purified from squid optic lobe (stain: HRP/ diaminobenzidine). (13B) Representative Western blots showing the stained protein band corresponding to Cp20 (index line). Visual inspection indicates a Cp20 reduction in AD (Alzheimer's disease fibroblast) and Es (Escapees, close relatives of Alzheimer's disease patients without symptoms) relative to fibroblasts from aged matched controls (AC). (13C) Graphic representation of quantitative analysis of each cell line shows clearly significant differences, with no overlap, between controls (Δ) as compared to AD (●) and Es (□), p<0.001 (ANOVA, Bonferroni post test). No significant differences were found between AD and Es fibroblasts. (13D) Bar graph representing the group data, further illustrating the significant Cp20 differences between control fibroblasts as compared to AD and Es cell lines.

Figure 14B:
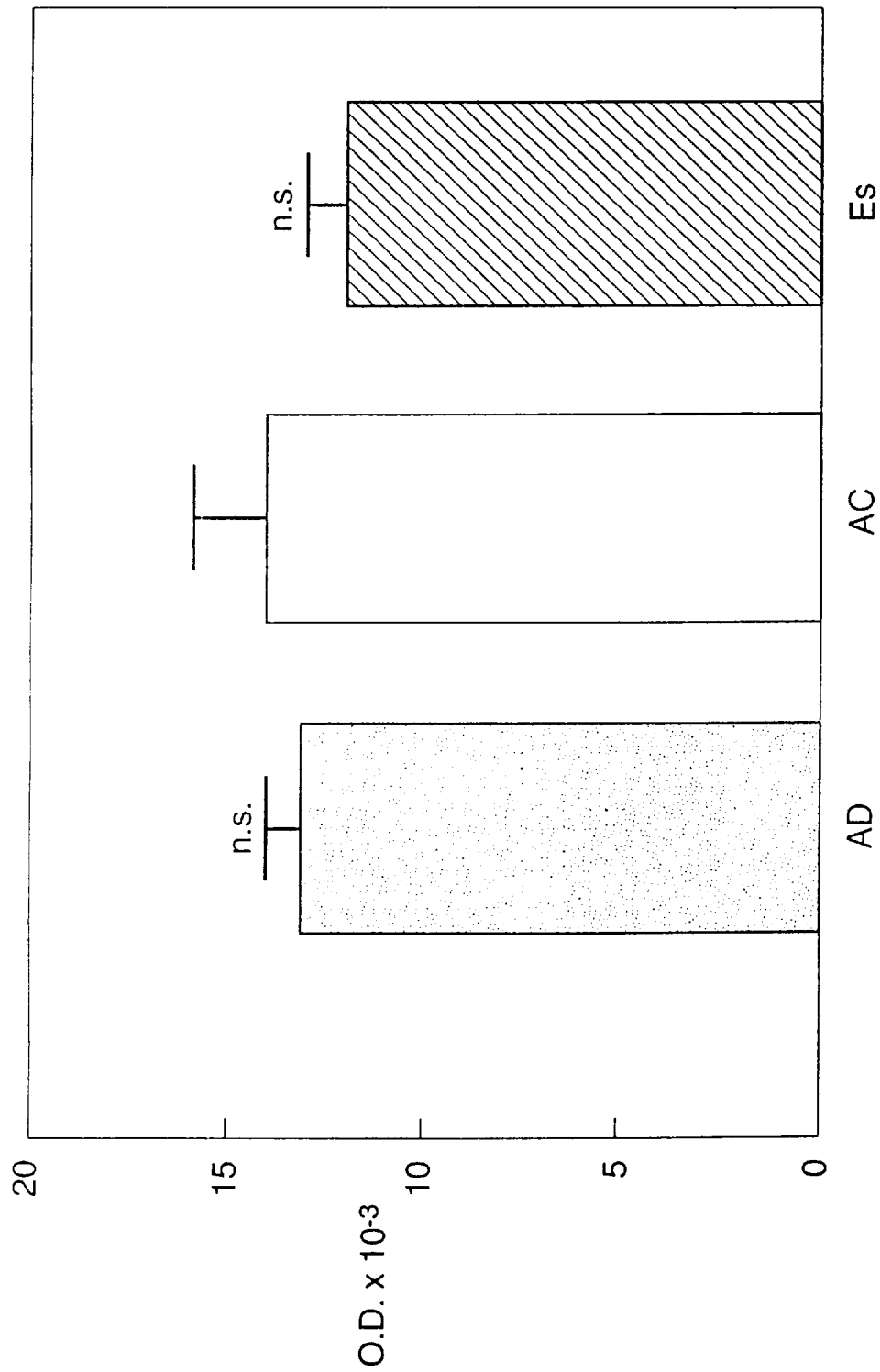

FIGS. 14A–14B. Coomassie stained protein gels of AD, Es, and AC fibroblasts. (14A) SDS-Page gels showing the protein profiles in all three groups studied.

Three regions were analyzed in detail in order to detect generalized protein changes in AD and Es fibroblasts, with particular attention to the protein bands with molecular weights similar to Cp20 ($\approx$20 kD). (14B) Quantitative analysis (graph) of the Cp20 region confirmed visual impressions that there are no between group differences around the 20 kD region. Similar analysis also showed no between-group differences of proteins with MW of 66 to 36 kD and in the 200 kD molecular weight region (see Example 6).

FIGS. 15A–15D. β-amyloid induces a reduction of Cp20 in control fibroblasts. (15A) Western blots of AC fibroblasts treated with β-amyloid for 48 h (right) and the same untreated cell lines (left). A reduction of Cp20 (index line) can be clearly observed in the β-amyloid treated cells as compared to the untreated counterparts. (15B) Bar graphs represent the quantitative analysis showing significant differences ($p<0.003$, Wilcoxon) between β-amyloid-treated and non-treated cells. (15C) Total protein profiles (Coomassie blue) revealed no differences between treated and non-treated cell lines. (15D) Quantitative analysis of protein bands around 20 kD (Cp20 M.W.) confirmed that β-amyloid did not cause general decrease of 20 kD MW region proteins (bar graph). Analysis of other bands (see Example 6) also showed no β-amyloid effects.

Figure 16A:
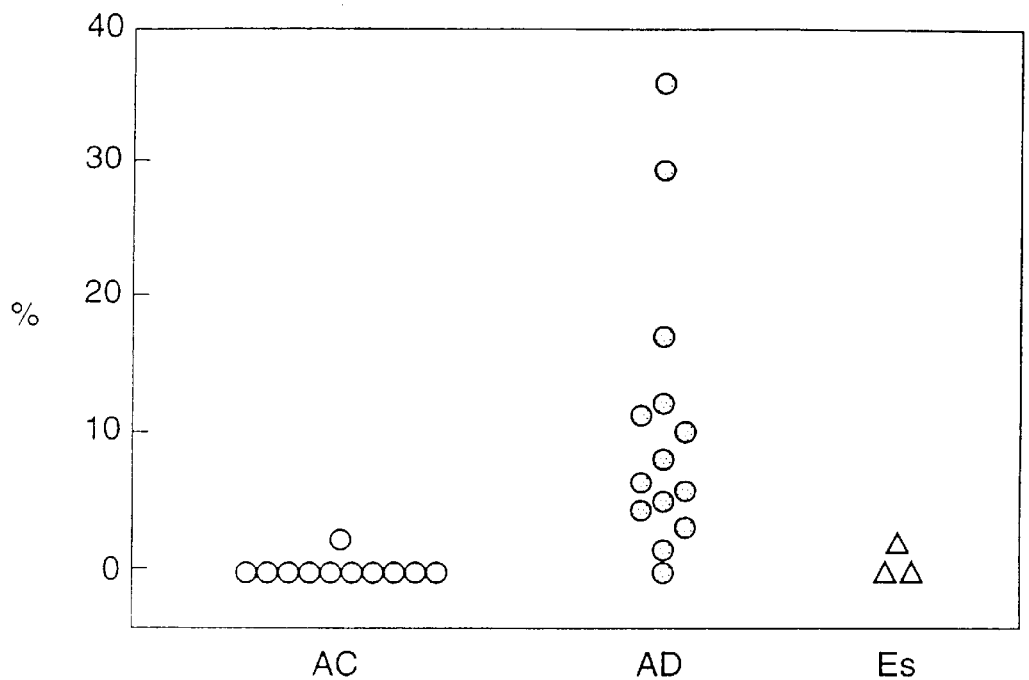
Figure 16B:
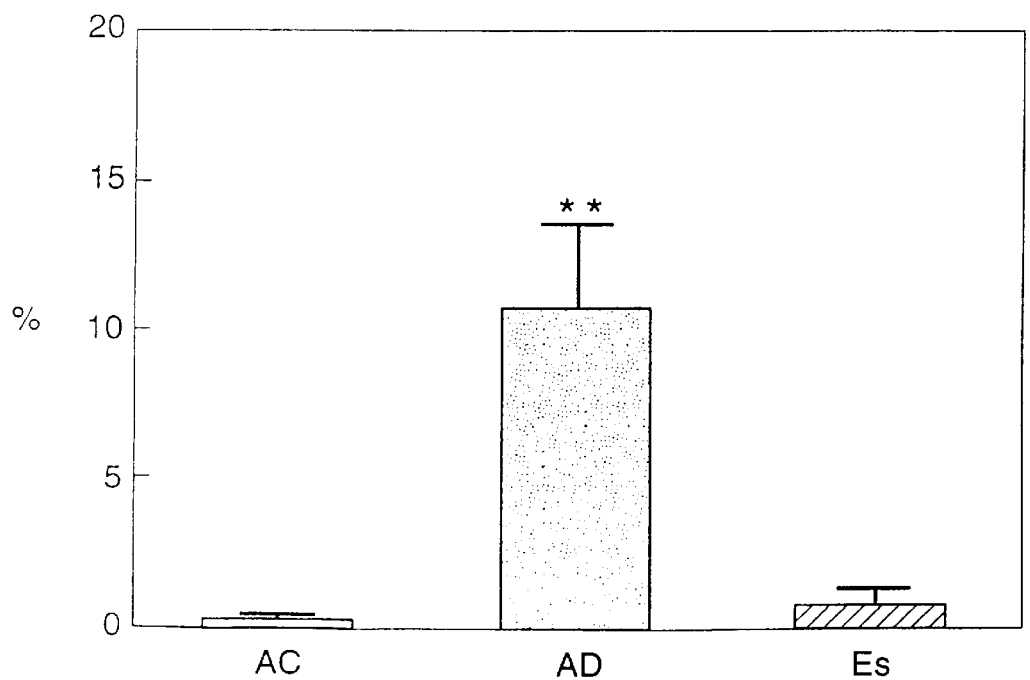

FIG. 16A–16C. Bradykinin-induced responses. Calcium elevations in response to 100 pM bradykinin were almost exclusively observed in AD cell lines. The graph represents each cell line tested (16A). The degree of responsiveness is expressed as % of cells responding to the challenge (no differences in the peak or integrated area were observed among responding cells). All but one (I4) AD cell lines responded, and the vast majority had higher % of responding cells than the one control (AG07141) that exhibited a response. Cell lines from Es have responses comparable to the control group. The highly significant group differences are shown in the bar graph (16B). A representative trace of the response is depicted in 16C. Solid lines are cell from the Coriell Cell Repositories. Broken lines are cell of Italian origin. The arrow indicates drug application.

Figure 17A:
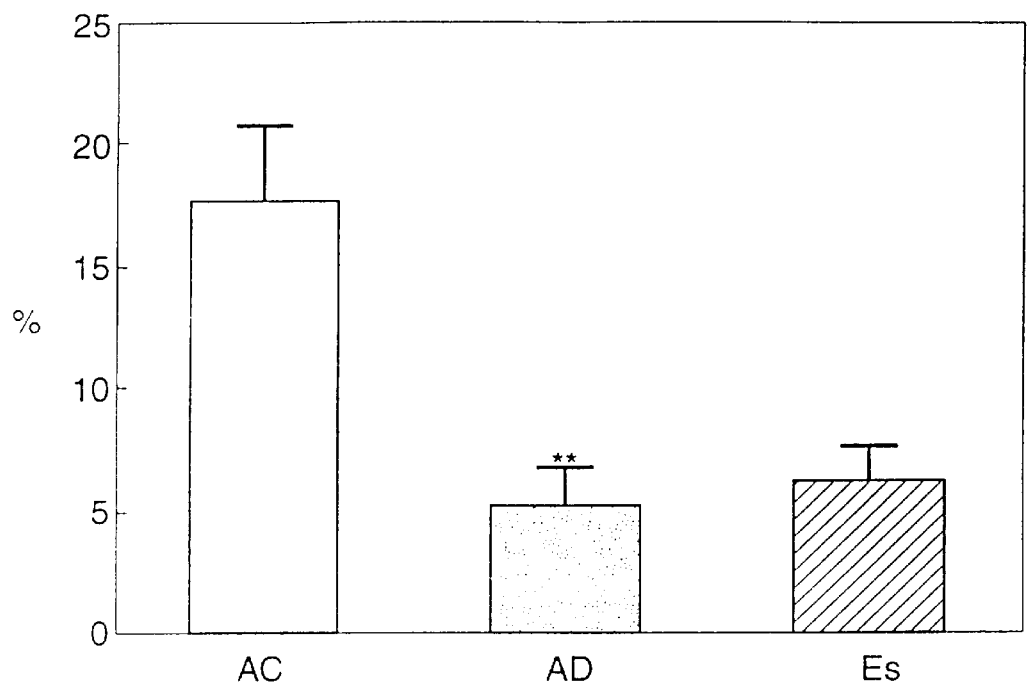
Figure 17B:
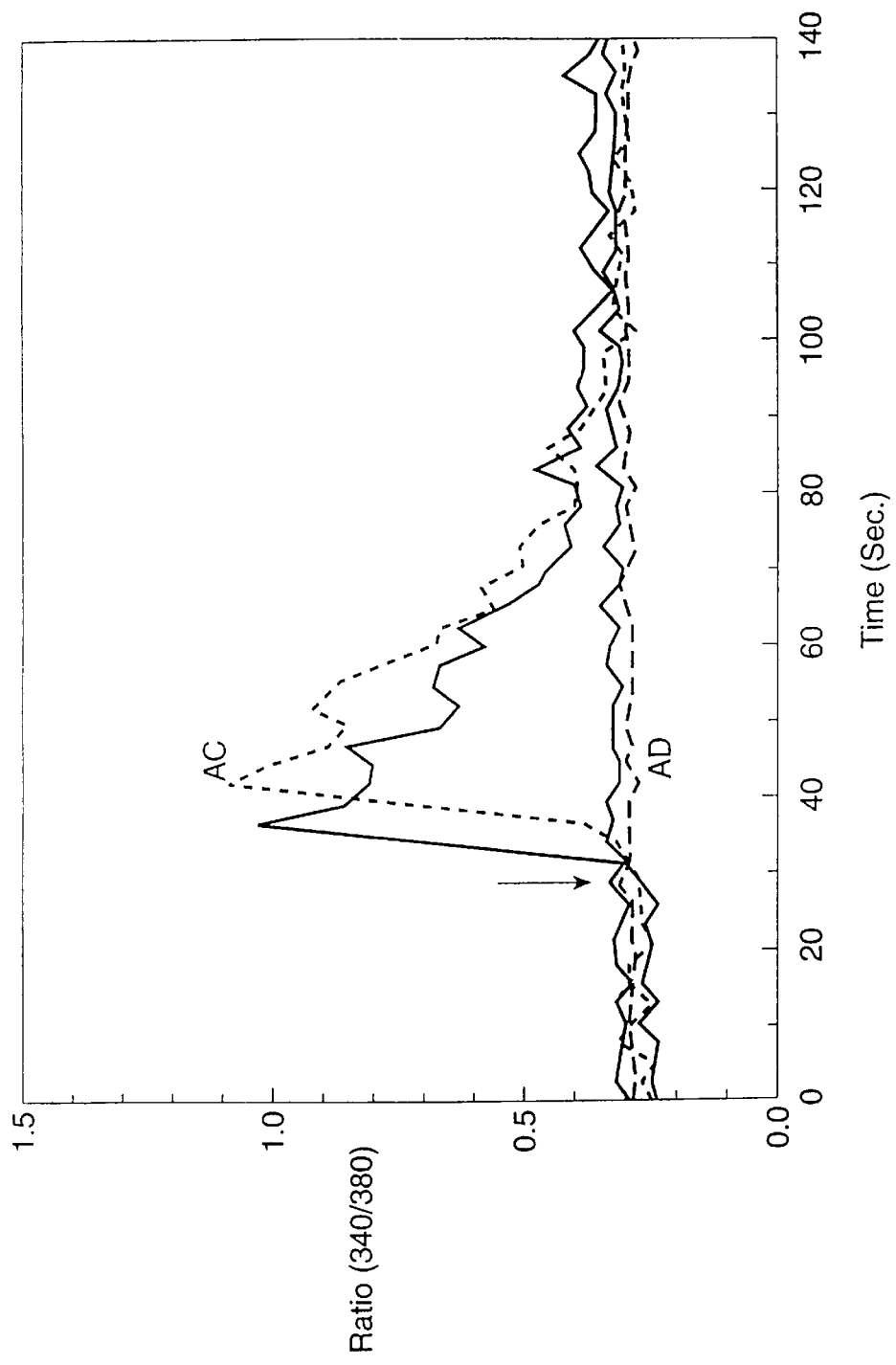

FIGS. 17A–17B. TEA-induced responses. Bars represent the average % of responding cells in each group. The % of responding cells in AD cell lines was significantly reduced as compared to controls, $p<0.001$. Es from the canadian AD family showed, on average, a % of responding cells similar to AD cell lines, and significantly lower than controls (17A). A typical TEA-induced response is illustrated in (17B). Dotted and solid lines represent cells' origin as in FIGS. 16A–16C.

Figure 18:
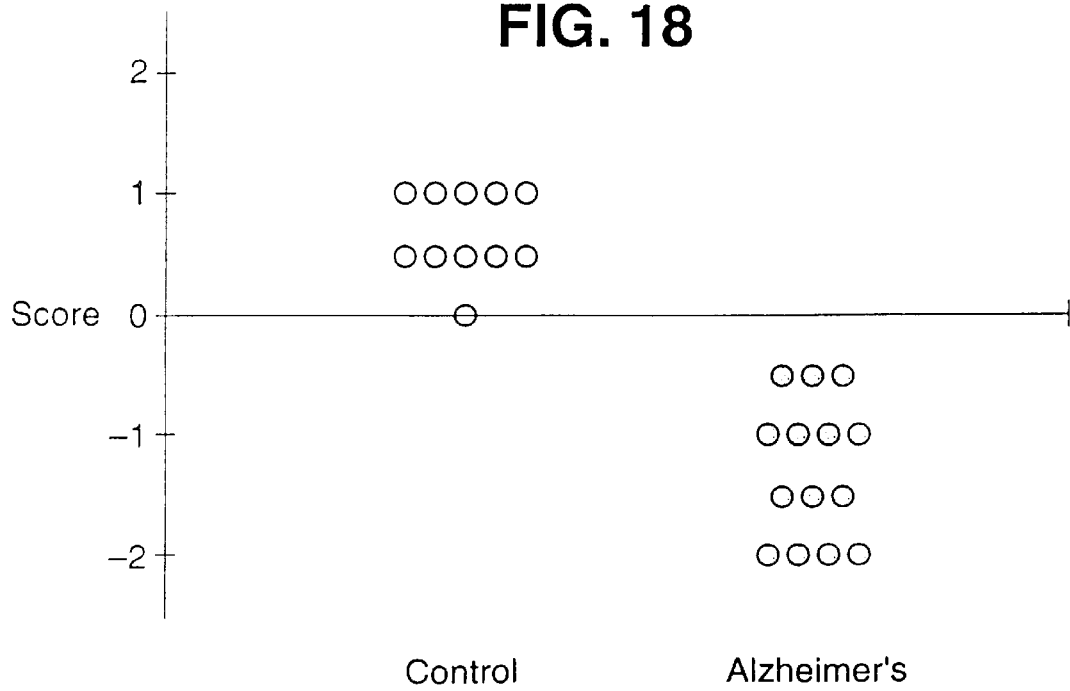

FIG. 18. Index for AD. Dots represent the combined score value for each particular cell line. As can be clearly observed from the figure, controls (open symbols) have significantly higher values than AD cell lines (solid symbols), $p<0.001$. The two groups also segregate without overlap.

FIGS. 19A–C. Western blot analyses of monoclonal anti-PKCα or PKCγ immunoreactivity in AC or AD fibroblasts before and after exposures to 10 mM β-amyloid (1–40) for 48 hours. (19A) Visual inspection reveals decreased PKCα immunoreactivity in AC fibroblasts after β-amyloid treatment. (19B) No modifications of PKCα immunoreactivity are visible in AD fibroblasts after treatment with β-amyloid protein. (19C) PKCγ immunoreactivity was decreased in AD cells after treatment with β-amyloid protein.

Figure 20A:
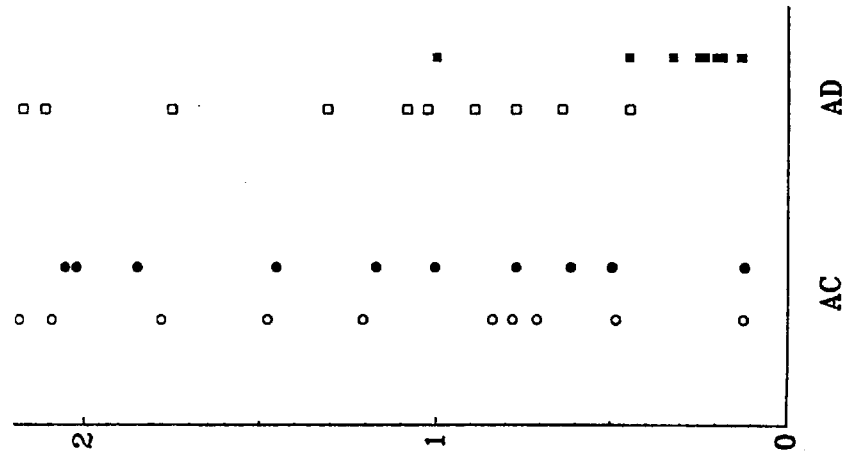
Figure 20B:
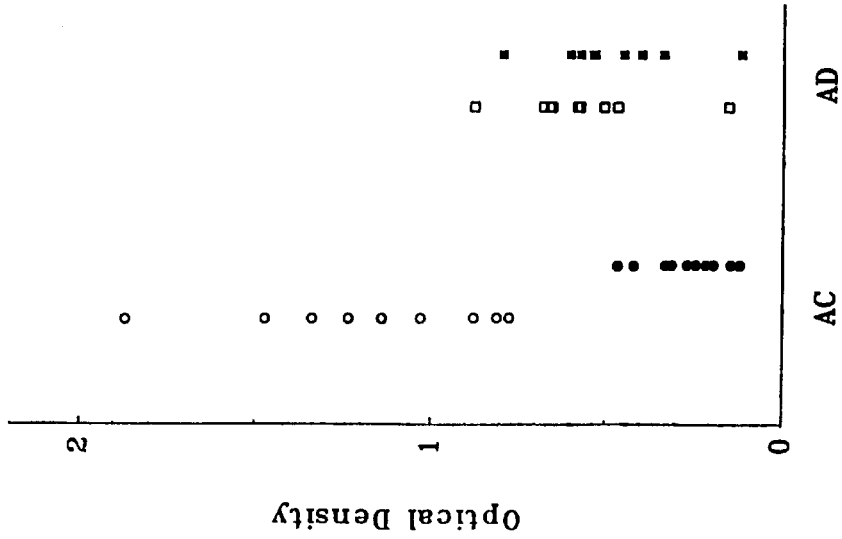

FIGS. 20A–B. Scatter plots of optical values of immunoreactive PKCα (20A) and PKCγ (20B) isozymes in Western blots of cell lines (10 aged-matched controls (AC), 4 non-familial AD, and 6 familial AD) which were untreated or treated with 10 nM β-amyloid (1–40) for 48 hours. The graph clearly illustrates the significant differences, with no overlap, between the untreated (○) and treated (●) control AC cells and the untreated (□) and treated (■) AD cells.

Figures 21A, 21B:
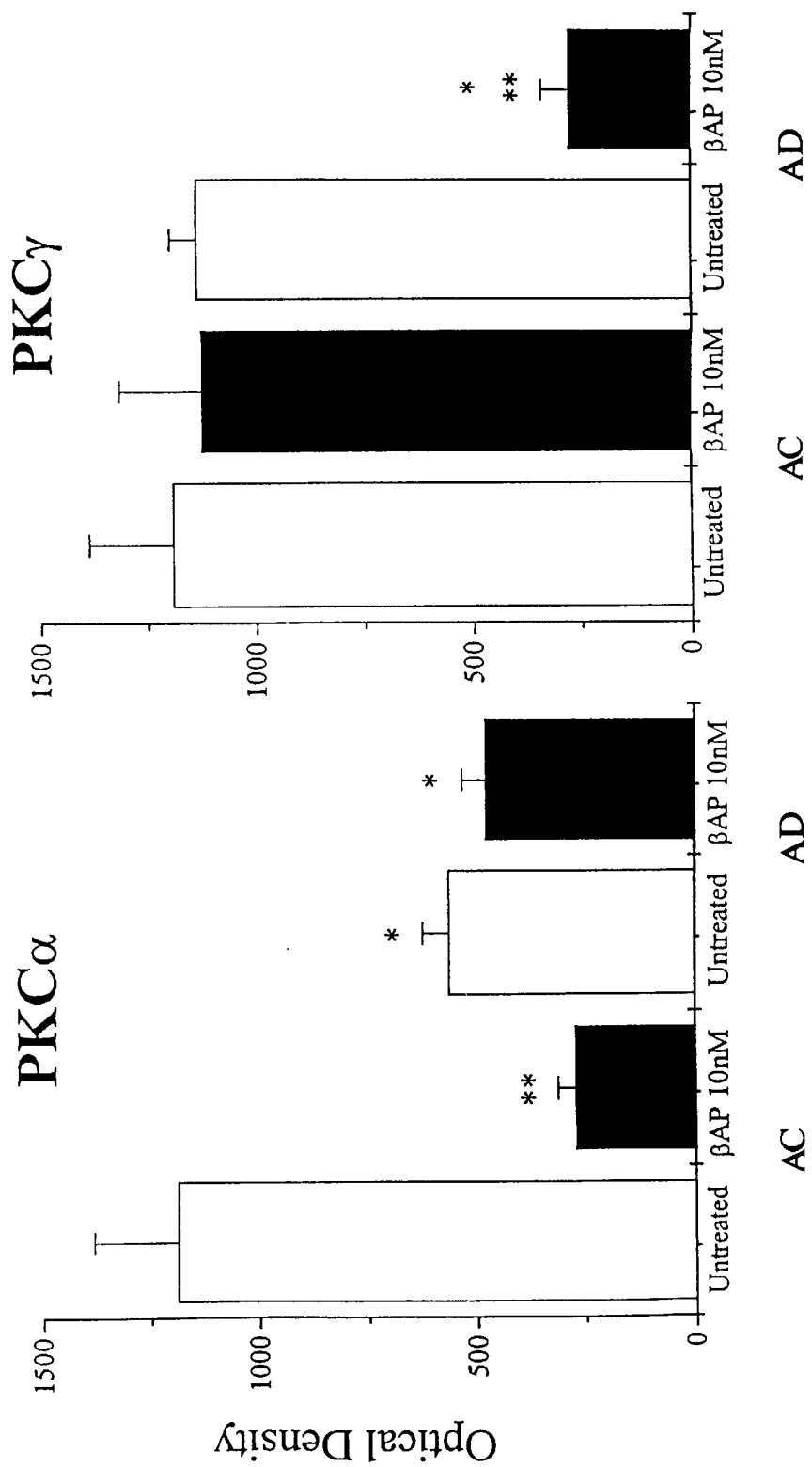

FIGS. 21A–B. Bar graphs of densitometric analyses of Western blots of monoclonal anti-PKCα or anti-PKCγ immunoreactivity in AC and AD fibroblasts before and after exposure to 10 nM β-amyloid for 48 h. The graphs show that PKCα (21A) and PKCγ (21B) are decreased in AC and AD fibroblasts respectively after β-amyloid treatment. Optical density as shown on the Y axis of FIGS. 21A and 21B is an arbitrary unit derived from densitometric analyses of the immunoreactive bands; values are the mean±SEM of 10 or more experiments per group; **, $P<0.001$, significance versus the untreated group; *, $P<0.001$, significance versus the AC group.

Figure 22A:
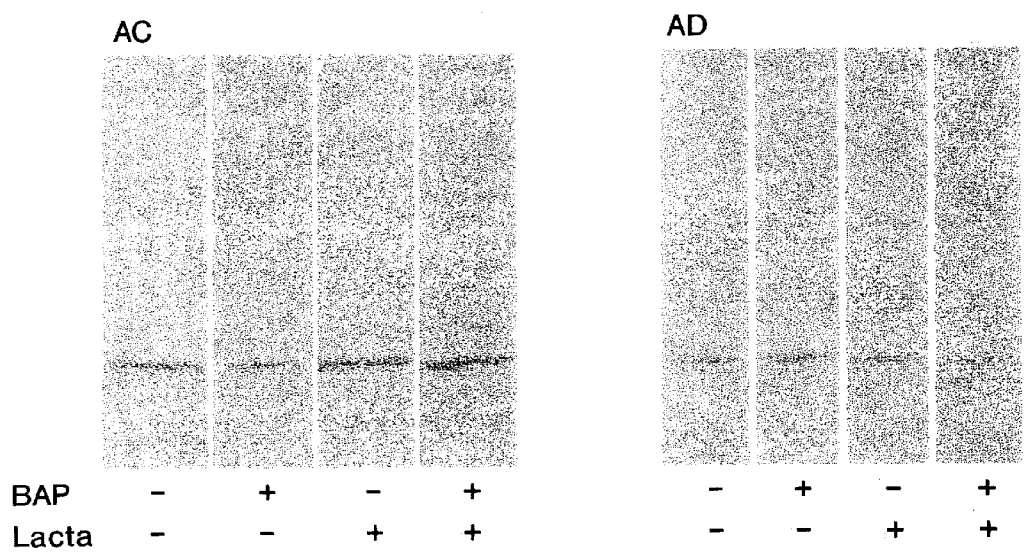
Figure 22B:
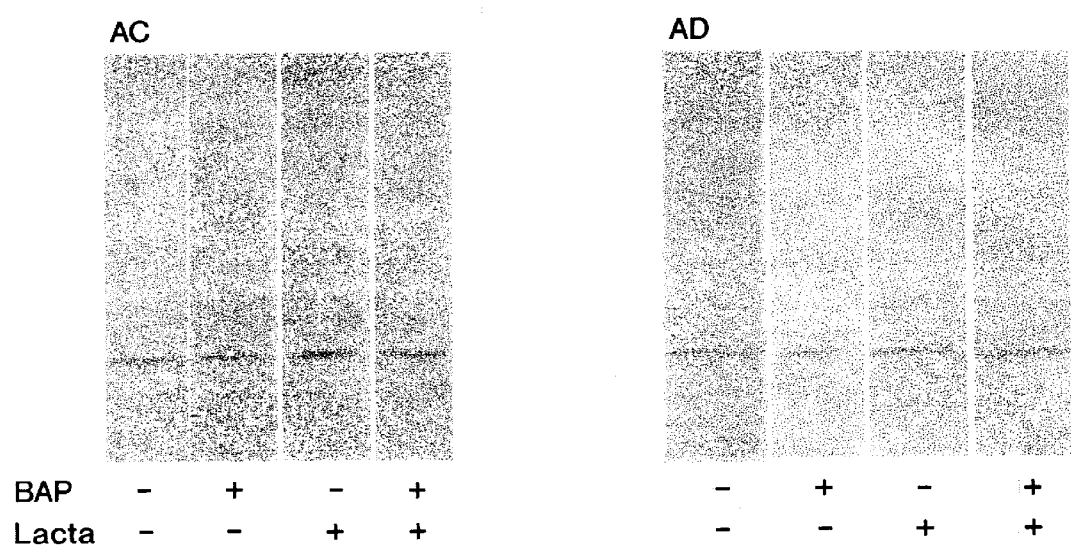

FIGS. 22A–B. Western blot analyses of monoclonal (22A) anti-PKCα and (22B) anti-PKCγ immunoreactivity in AC and AD fibroblasts after 1 hour preincubation with 50 FM of lactacystine (Lacta) followed by treatment with 10 nM β-amyloid (1–40) for 48 hours. β-amyloid-mediated decrease of PKCα immunoreactivity (22A) in AC fibroblasts and PKCγ immunoreactivity (22B) in AD fibroblasts is blocked by treatment with lactacystine.

FIGS. 23A–B. Western blot analyses of monoclonal anti-PKCα immunoreactivity in (23A) untreated and treated (10 nM β-amyloid for 48 hours) rat cerebellar granule cells at different days of maturation in vitro (DIV) and in (23B) rat cortical neurons either untreated or treated with 10 nM β-amyloid for 48 hours followed by 3 hour treatment with 100 nM phorbol 12-myristate 13-acetate (PMA). Visual inspection reveals no modifications in PKCα immunoreactivity in rat cerebellar granule cells at 2 days of maturation in vitro (23A left panel) whereas decrease in PKCα immunoreactivity is observed after neuronal differentiation at 8 days of maturation in vitro (23A right panel). For cortical neuron, a decrease of PKCα immunoreactivity is observed at 8 days of maturation in vitro after β-amyloid treatment and treatment of β-amyloid protein-treated cortical neurons with PMA restores the PKCα signal (23B).

FIGS. 24A–B. Western blot analyses of monoclonal anti-PKCα (24A) and anti-PKCγ (24B) immunoreactivity after preincubation with cycloheximide (CHX) followed by β-amyloid treatment: or treatment with β-amyloid followed by phorbol ester (PMA) treatment. Visual inspection reveals that (24A) the decrease of PKCα immunoreactivity after exposure to 10 nM β-amyloid protein for 48 h was blocked by 30 min preincubation with 100 AM CHX. PKC activation with 100 nM PMA for 3 hours restored the PKCα immunoreactive signal in β-amyloid-treated AC. PMA effect was blocked by preincubation with CHX. No modifications of PKCα immunoreactivity are visible in the AD group. (24B) β-amyloid-mediated decrease of PKCγ immunoreactivity in AD cells is not affected by the preincubation with CHX or by the PMA treatment.

FIGS. 25A–B. Bar graphs of densitometric analyses of Western blots of monoclonal anti-PKCα and PKCγ immunoreactivity in AC and AD fibroblasts after treatment with (25A) cycloheximide (CHX) or (25B) phorbol ester (PMA). Optical density as shown on the Y axes of FIGS. 25A and 25B is an arbitrary unit from densitometric analyses of the immunoreactive bands; values are the mean±SEM of 3 experiments per group. *, $P<0.001$, t-test, two tail.

Figure 26A:
Figure 26B:
Figure 26C:

FIGS. 26A–C. Confocal microscopy imaging of PKCα immunofluorescence in (26A) untreated AC fibroblasts, in (26B) AC fibroblasts after treatment with 10 nM β-amyloid protein (1–40) for 48 hours, and in (26C) AC cells after treatment with 10 nM β-amyloid protein (1–40) for 48 hours followed by phorbol ester (PMA).

Figure 27:
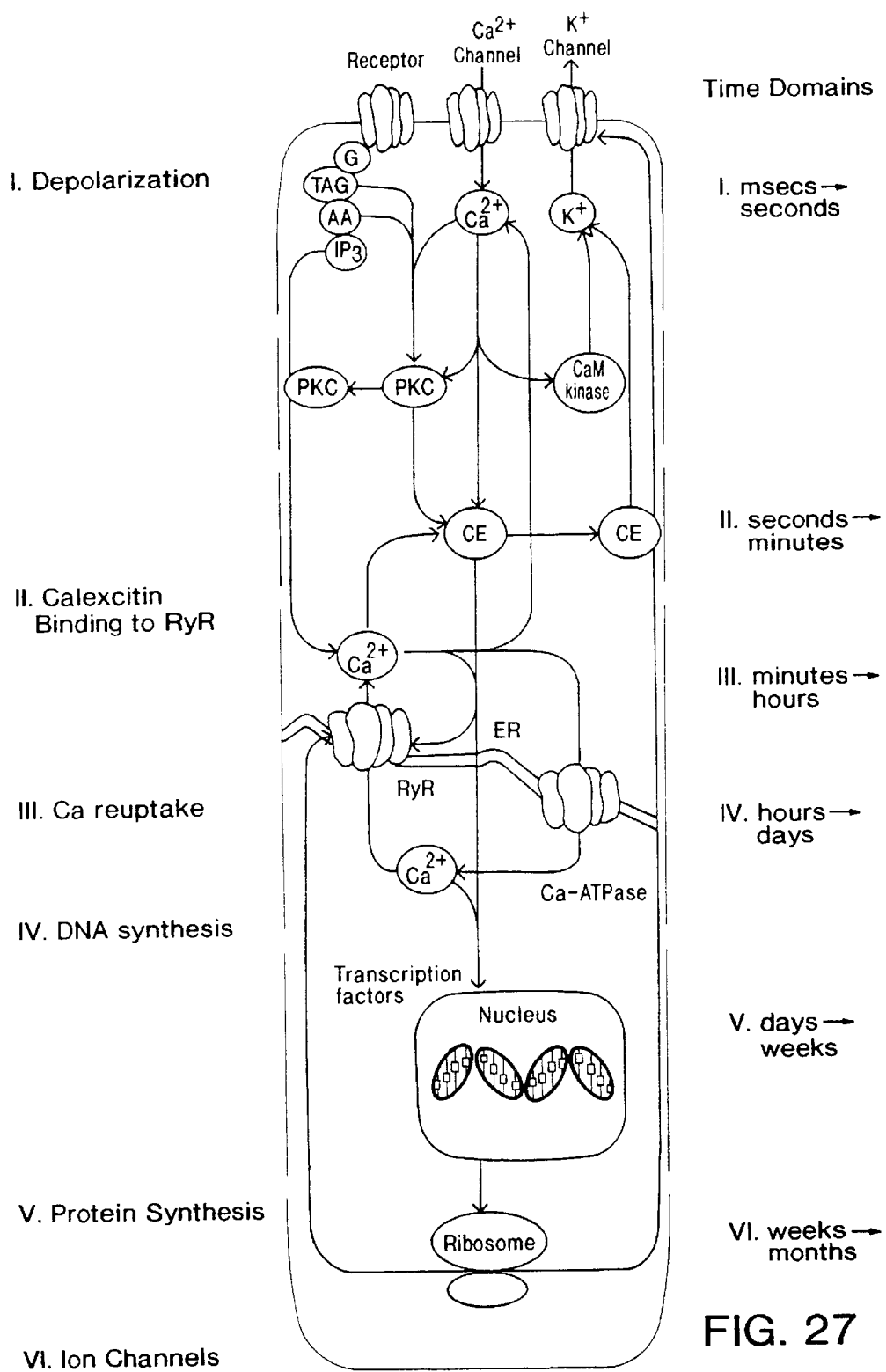

FIG. 27 is a schematic diagram illustrating six time domains of calcium signaling represented as Stages I–VI. Stage I: The neuron depolarizes as a result of a convergence of synaptic input, which activates G-protein coupled receptors (e.g. for acetylcholine, GABA, glutamate). Membrane depolarization also opens $Ca^{2+}$ channels, causing an influx of $Ca^{2+}$. Diacylglycerol (DAG), arachidonic acid (AA), and inositol triphosphate ($IP_3$) are released by phospholipases, and, along with $Ca^{2+}$, activate protein kinase C (PKC), which is thereby translocated to the plasma membrane. $Ca^{2+}$ also activates calmodulin (CaM) kinase. The kinases undergo autophosphorylation which renders their activity independent of $Ca^{2+}$. PKC and CaM kinase may also inhibit $K^+$ and other channels by direct phosphorylation.

Stage II: Elevated $Ca^{2+}$ activates the $Ca^{2+}$-binding protein Cp20, also called calexcitin (CE). Phosphorylation of CE by PKC promotes its translocation to membrane compartments, where it inhibits $K^+$ channels, making the membrane more excitable to further depolarizing stimuli. CE also elicits $Ca^{2+}$ release from ryanodine receptors (RyR) on the membrane of the endoplasmic reticulum (ER) and possibly synaptic membranes, resulting in amplification of $Ca^{2+}$ signals.

Stage III: CE, after phosphorylation by PKC, no longer activates the RyR, but activates $Ca^{2+}$-ATPase at the ER membrane, facilitating the removal of excess $Ca^{2+}$.

Stage IV: CE and/or $Ca^{2+}$, probably acting indirectly through transcriptional activators, induce new RNA transcription. CE also increases mRNA turnover.

Stage V: Late genes are transcribed, resulting in increased synthesis of at least 21 different proteins, including RyR. At this stage, retrograde axonal transport is also inhibited by CE; it is believed that this inhibitor may underlie the structural changes in dendritic morphology that are observed after associative learning.

Stage VI: New RyR receptors and ion channels are synthesized and transported to their respective membranes.

DETAILED DESCRIPTION OF THE INVENTION

The invention concerns methods of diagnosing Alzheimer's disease (AD). These methods are based upon detecting the absence of a particular potassium ion channel in the cells of an AD patient; upon differences in intracellular calcium ion concentration in AD and non-AD cells in response to potassium channel blockers specific for the potassium ion channel that is absent in the cells of an AD patient; and differences between AD and non-AD cells in response to activators of intracellular calcium release such as activators of inositol-1,4,5-triphosphate ($IP_3$). This invention also provides additional methods of diagnosing AD based upon detecting a significant reduction in the levels of a memory associated GTP-binding protein+(Cp20) in the cells of an AD patient. This invention also provides methods of diagnosing AD based upon differential effects of β-amyloid or levels of the protein kinase C isoenzymes PKCα and PKCγ in AD and non-AD cells. In addition, this invention provides methods of diagnosing AD based on detecting Eu-TTA florescence differences between AD and non-AD cells following treatment with an activator of a receptor-mediated metabolic pathway.

The first embodiment of the invention is based upon the discovery by the inventors that cells from people not suffering from AD have (at least-) two types of functional potassium channels, with conductances of 113 pS (picosiemens) and 166 pS, as measured by the patch clamp technique (see Example 1). The 113 pS channel is either missing or not functioning in people with AD. The first embodiment of the invention involves diagnosing AD by determining whether cells of the patient have a functioning 113 pS potassium channel. The presence of a functioning 113 pS potassium channel indicates that the patient does not have AD. However, the absence of a functioning 113 pS potassium channel indicates that the patient does have AD.

In this embodiment of the invention, a suitable method of recording electrical conductances in the cells must be used to detect functional potassium channels in cells. Any technique which can measure electrical conductances in a cell can be used. Examples include intracellular microelectrode recording (indirect measurement), two microelectrode voltage clamp, and single microelectrode voltage clamp. The patch clamp technique, as described herein, is a preferred method for measuring electrical conductance in small structures. In an embodiment of the invention, the cell attached mode of the patch clamp technique is used to record the existence of potassium channels and the inside-out and outside-out patch configurations are used to record the sensitivity of potassium channels to various chemicals.

The second embodiment of the invention concerns another method for diagnosing AD. En this second embodiment, the cells are contacted with a potassium channel blocker that blocks the 113 pS channel but not the 166 pS channel. This blocker may substantially block the 113 pS channel but not substantially block the 166 pS channel. An example of such a blocker is TEA, or tetraethylammonium. The blocker has the effect in non-AD cells of transiently increasing intracellular $Ca^{2+}$ concentrations. In AD cells, the blocker has substantially no effect, allowing for variation within observational or technical error. In contrast, the intracellular calcium ion concentration increases several fold in non-AD cells after being e-posed to 100 mM TEA (see FIG. 4B). The intracellular $Ca^{2+}$ concentration can be measured in various ways, such as by adding fluorescent indicators or absorbance indicators or by using a $Ca^{2+}$ electrode. Preferably, because of ease of operation, fluorescent indicators are used.

In this embodiment of the invention, the cells are first cultured with a $Ca^{2+}$ indicator, such as quin or fura-2, that fluoresces with an intensity proportional to the calcium concentration. The cells are then contacted with a select potassium channel blocker that has the ability to block the 113 pS channel but not the 166 pS channel. The fluorescence intensity of the cells before and after the addition of the potassium channel blocker is measured. In cells from people not suffering from AD the fluorescence intensity increases rapidly, peaks and then drops back down (FIG. 4C). This shows that the blocker has the effect of increasing, transiently, the calcium ion concentration. In cells from AD patients, the fluorescence intensity is substantially the same before and after the blocker is added. This is a reflection of the fact that the 113 pS channel is missing or non-functional in AD patients and thus potassium ion channel blockers that block the 113 pS channel, but not the 166 pS channel, do not have any effect on BAD cells.

As mentioned above, the select potassium channel blocker used in this second embodiment of the invention is one that has the ability to block the 113 pS potassium channel but that has little or no effect on the 166 potassium channel. One example of such a blocker is TEA, with any biologically compatible co-anter anion. Preferably, the counterion is chloride. Other suitable potassium channel blockers can be easily found using the following method. Using the patch clamp technique described in Example 1, the 113 pS and 166 pS channels are detected in a viable human cell. The candidate potassium channel blocker is added to the culture containing the cells, and the patch clamp technique is used again. If the 166 pS channel is still functional, but the 113 pS channel is not, then the candidate blocker is suitable for use in this invention. Candidate potassium channel blockers include the known potassium channel blockers charybdotoxin, apamin, dendrotoxin, kalidotoxin, MCD-peptide, scyllatoxin, barium, cesium, leiurotoxin I and noxiustoxin. As shown in Example 2, TEA concentrations between 10 mM and 100 mM worked well. It is easy to extend this range of workable concentrations by using AD and non-AD control cells.

Example 2 exemplifies the second embodiment of the invention for diagnosing AD using a select potassium channel blocker, TEA, and measuring the effect on intracellular calcium ion. This method is so simple, with a yes or no answer, that the exemplified sophisticated apparatus is not required to make the diagnosis. Any method which will tell one if the intracellular calcium ion concentrations has increased or not as a result of contact with the select potassium ion channel blocker will suffice to give a diagnosis. In the preferred method, fluorescent calcium ion indicators are used. In this case, any method which will tell one if the fluorescence of the indicator has increased or not as a result of contact of the cells with the select potassium channel blockers will suffice. Any method used must be able to make the measurements in the short time available. The calcium ion influx peaks a short time after contact with the blocker, and then decreases to the baseline value. In Example 2, the time it takes to peak is less than one minute.

A simpler method for detecting a fluorescent calcium ion indicator would involve using a fluorimeter, a device with a light source for exciting the calcium ion indicator and a light meter for measuring the intensity of a the fluorescence. Fluorimeters are well known and commercially available. At the simplest level, the calcium ion indicator is added to the cells taken from the patient (either fresh or expanded in culture). After an hour or so of being in contact with the indicator (at about 2 micromolar concentration) the cells in suspension are placed in the fluorimeter and the fluorescence intensity from the indicator is measured. Then the select potassium channel blocker is added; if TEA is used, it is added to a concentration of about 100 mM. The fluorescence is measured again. If the intensity, within a time period between 20 seconds and 40 seconds, is substantially the same as before the TEA was added (taking account of changes in volume due to the addition of the TEA), then a positive diagnosis of PD is made. If the intensity increases within 30 seconds and subsides after another 30 seconds, then the patient does not have AD.

It is within the skill of the art to improve the simple scheme outlined above. For Example, one could use a fluorimeter with dual sample holders, in which the difference in fluorescence from two samples is measured. Starting with identical samples of patient's cells (after incubation with the indicator) in each sample holder, the select potassium channel blocker is added to only one of the samples. If there is no change in the difference signal (that is, it remains as essentially zero), a diagnosis of AD is made. If the difference signal changes significantly, then the patient does not have AD. The advantage of the differences method is that it has a built in control which increases the accuracy of the measurement. It is still within the skill of the art to add the select potassium channel blocker automatically and to make more than one measurement at a time; i.e., to automate the method for a commercial medical laboratory. Before making any diagnoses using the methods taught here, the methods should be optimized for the particular apparatus and conditions in the laboratory by using non-AD and AD control cells, which are commercially available.

The third embodiment of them invention is yet another method of diagnosing AD. This method concerns the effect of agents that activate inositol-1,4,5,-triphosphate ($IP_3$) or otherwise induce the release of calcium from intracellular storage sites. Such storage sites include the endoplasmic reticulum and other organelles that have receptors for $IP_3$. The preferred $IP_3$ activator is bombesin. Other agents that activate the release of calcium from intracellular stores which are useful in the invention include thrombin, bradykinin, prostaglandin $F_{2a}$ and vasopressin. See, e.g., Berridge, M. J. and Irvine, R. F. (1984) *Nature* 312:135).

It has been discovered that cells from people not suffering from AD and cells from people suffering from AD both transiently release calcium ion in response to bombesin, but the resulting intracellular calcium concentration is much larger in AD (cells than in non-AD cells. The determination is easily made using any method of measuring intracellular calcium ion concentration, as discussed above with respect to the second embodiment of the invention. Again, the use of fluorescent calcium indicators is the preferred method. The same experimental setup as described above for measuring fluorescence intensity can be used, i.e., a fluorimeter. In this method, it is also possible to standardize the fluorescence apparatus using non-AD and AD cells as controls. In this way, later measurements of just the patient's cells can provide a diagnosis. Alternatively, the patient's cells can be compared with non-AD cells as a control.

Figure 5A:
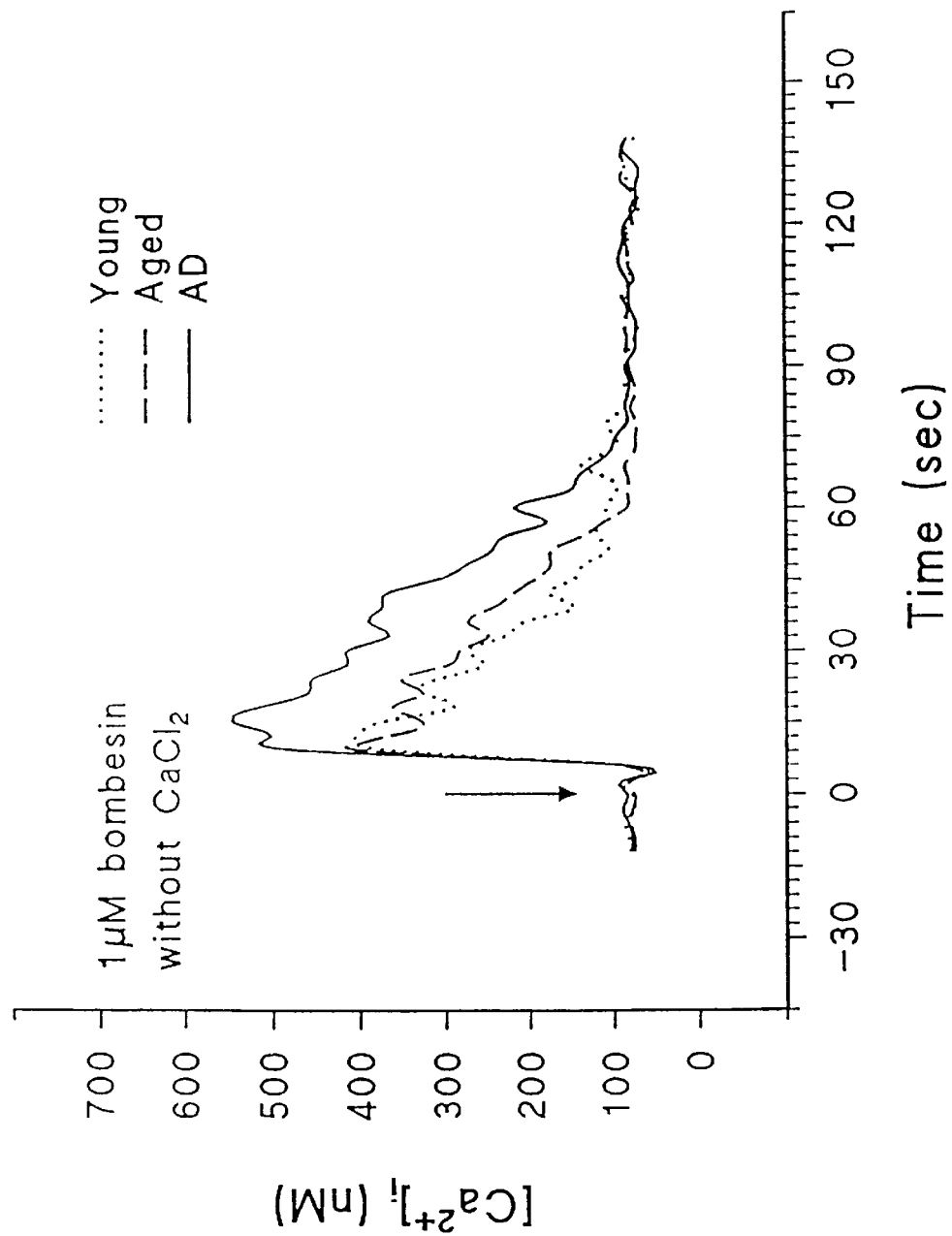

Example 3 exemplifies the third embodiment of the invention concerning the diagnosis of AD using activators of $IP_3$ and measuring their effect on calcium ion release into the cytosol from intracellular storage sites after contact with said activators. The amount of released calcium is larger in AD cells compared to non-AD cells. The increase in intracellular calcium concentration is transient: the concentration peaks soon after contact with the activator and is back to baseline value with 90 seconds. This effect is enhanced when the extracellular calcium ion concentration is zero or near zero (which is generally accomplished by washing the cells with BSS nominally free of calcium, however, other methods of tying up or negating the effect of the extracellular calcium ions can be used, such as adding EGTA, or adding a calcium channel blocker such as nifedipine, respectively). After contact with an $IP_3$ activator, such as bombesin, the intracellular calcium ion concentration in AD cells reaches a higher peak value and takers longer to return to the baseline value than either young or aged control cells (FIG. 5A). In the experimental setup described in Example 3, it was found that 42 seconds after the bombesin was added to the cells that the difference between the intracellular calcium ion concentrations in AD cells and in control cells was at a maximum, and that at that time period, i.e., at 42 seconds after bombesin was applied, the concentration of calcium ions was always greater than 300 nM in AD cells and was always less than 300 nM in control non-AD cells (FIG. 5B). Basal levels of both AD and non-AD fibroblasts were at 80 nM±0.5 nM. However, it should be noted that control values might differ from 80 nM, necessitating a criterion level of calcium signal greater or less than 300 nM. Furthermore, differences in measuring conditions might require a time longer or briefer than 42 seconds to show maximal differences between the calcium signals of AD a-nd non-AD fibroblasts.

Again, it is not necessary to use the sophisticated methods and apparatus exemplified herein. This method of diagnosing AD can be performed more simply. One need not measure the absolute concentration of intracellular calcium; a measurement of its relative value will also work. In Example 3, the basal level of intracellular calcium ion concentrations in resting (i.e., nonactivated) cells was the same for both AD and control non-AD cells, 80 nM±0.5 nM. Thus, at the time where the concentration differences between AD and non-AD cells was maximum (i.e., at 42 seconds using bombesin and the inventors' apparatus, but the time would need to be worked out empirically for different activators and different setups) the intracellular calcium concentration in non-AD cells would be less than (300/80=) 3.75 times the basal level whereas the intracellular calcium concentration in AD cells would be greater than (300/80=) 3.75 times the basal level. Using commercially available AD and non-AD cells, one can easily determine the time at which the calcium concentrations are maximally different between AD and non-AD cells. This involves measuring relative intracellular calcium concentrations for resting cells, adding bombesin or another $IP_3$ activator, following the relative calcium ion concentrations for a minute or so, and finding the time (after the activator is added) at which the difference in relative calcium ion concentrations is at its maximum. Then, for any real sample from a patient, one simply needs to measure the relative basal intracellular calcium concentration by any means known in the art, add the activator to its prescribed concentration (about 1 micromolar for bombesin), wait the predetermined time and again measure the relative intracellular calcium concentration. If the ratio of the intracellular calcium concentration "after" the addition of the activator to the intracellular calcium concentration "before" the addition of the activator is greater than 3.75, the patient has AD; if it is less than 3.75, the patient does not have AD. It is not necessary to determine the time of maximal difference in calcium concentrations—any time where there is a reproducible difference between these ratios can be used. It is only necessary to work out the particular ratios for the time chosen from known AD and non-AD control cells.

The calcium ion indicators used in the second and third embodiments include any compounds which can enter the cell, are biocompatible, and which can bind to calcium ions to produce a species whose concentration is easily measured using any physico-chemical means and is proportional to the calcium ion concentration. Preferably the means is fluorescence or absorbance. Preferable fluorescent indicators are the commercially available indicators fura-2 AM, fura-2 pentapotassium salt, quin-2, and indo-1 from Molecular Probes (Eigene, Oreg.). The Chemical Abstracts name for fura-2, AM is 5-oxazolecarboxylic acid, 2-(6-(bis(2-((acetyloxy)methoxy)-2-oxoethyl)amino)-5-(2-(2-(bis(2-((acetyloxy)methoxy)-2-oxoethyl)amino)-5-methylphenoxy)ethoxy)-2-benzofuranyl)-, (acetyloxyl) methyl ester. The Chemical Abstracts name for fura-2, pentapotassium salt is 5-oxazolecarboxylic acid, 2-(6-(bis (carboxymethyl)amino)-5-(2-(2-(bis(carboxymethyl) amino)-5-methylphenoxy)ethoxy)-2-benzofuranyl)-. Other fluorescent calcium indicators include Fluo-3, Rhod-2, Calcium Green™, Calcium Orange™, Calcium Crimson™ Fura Red™ and Calcium Green Dextran™ (Molecular Probes (Eugene, Oreg.)). Generally, the cells are incubated with the indicators at a concentration of about 2 micromolar for about 60 minutes. An absorbance indicator which may be used is arsenazo. Finally, calcium levels could also be measured for this invention with calcium electrodes inserted into the cells.

In the exemplified embodiment of the invention, fluorescence was measured using an imaging system under the control of a personal computer. For excitation, 340 nm and 380 nm band pass path filters with a neutral-density filter were used. Images of fluorescence were obtained using a dichroic mirror, barrier filter and objective lens. The whole image can be recorded or portions thereof. A Hamamatsu Photonics Argus 50 Calcium Imaging system imaging 60 cells in a microscopic field at 10× magnification was used. Fluorescence from the cells was quantified in ¼ of the field at 10× magnification. Such an imaging system (and other similar currently available systems) with its microscope could be custom designed for everyday clinical laboratory analysis of cells' calcium signals. Other instrumentation and/or measurements would have to be adapted for the use of other calcium indicators.

In the methods of the invention, the cells that are taken from the patient can be any viable cells. Preferably they are fibroblasts; buccal mucosal cells; blood cells such as erythrocytes, lymphocytes, and lymphoblastoid cells; or nerve cells such as olfactory neurons. The cells may be fresh or may be cultured (as described in the examples). The fibroblast potassium channel dysfunction and resulting absence of TEA-induced calcium signals described herein suggest that AD, which primarily affects brain cells, is likely to alter potassium channel function in many Different types of cells in the body. Similarly, AD is likely to alter calcium released by bombesin and related agents in many different types of cells in the body. The methods described herein to measure potassium channel function and calcium release, therefore, should be applicable for AD diagnosis using other cell types.

A punch skin biopsy could be used to obtain skin fibroblasts from a patient. These fibroblasts might be analyzed directly with the techniques described herein or be introduced into cell culture conditions. The resulting cultured fibroblasts would then be analyzed as described for the cultured fibroblasts obtained from the Coriell Cell Repositories described below. Other steps would be required to prepare other types of cells which might be used for analysis such as buccal mucosal cells, nerve cells such as olfactory cells, blood cells such as erythrocytes and lymphocytes, etc. for example, blood cells can be easily obtained by drawing blood from peripheral veins. Cells can then be separated by standard procedures (e.g., by using a cell sorter, centrifugation, etc.) and later analyzed in suspension or on a solid support (e.g., in petri dishes).

The fourth embodiment of this invention concerns yet another method for diagnosing Alzheimer's disease. This embodiment is based upon a discovery by the inventors that the memory associated GTP protein Cp20 is significantly reduced in the cells of Alzheimer's disease patients relative to the cells of healthy controls. Cp20, a high-affinity substrate for protein kinase C (PKC) (D. L. Alkon et al., *J. Neurochem.* 51, 903 (1988)), shows specific differences of phosphorylation in neurons of mollusks and mammals that undergo associative learning (J. T. Neary, T. Crow, D. L. Alkon, *Nature* 293, 658 (1981); T. J. Nelson, J. V. Sanchez-Andres; B. G. Schreurs, D. L. Alkon, *J. Neurochem.* 57, 2065 (1991); T. J. Nelson, C. Collin, D. L. Alkon, *Science* 247, 1479 (1990).). This GTP-binding protein, which induces a number of memory-specific neuronal changes [e.g. $K^+$ current reduction, increased synthesis of mRNA, and focusing of synaptic terminal branches—T. J. Nelson, C. Collin, D. L. Alkon, *Science* 247, 1479 (1990); T. J. Nelson and D. L. Alkon, USA 85, 7800 (1988); ibid 87, 269 (1990); D. L. Alkon et al. *Proc. Natl. Acad. Sci.* USA 87, 1611 (1990)1, also regulates retrograde axonal transport (S. Moshiach, et al. *Brain Research* 605, 298 (1993)) and is a member of the adenosine diphosphate ribosylation factor (ARF)-protein family that has been implicated in the trafficking of particles between the Golgi and the endoplasmic reticulum (see Example 5). Here it is demonstrated that Cp20 is consistently and significantly reduced in the fibroblasts of both Alzheimer's patients and non-affected close relatives of Alzheimer's Disease patients, but not in aged-matched controls who are not members of families with hereditary Alzheimer's disease. Incubation of normal fibroblasts with low concentrations of soluble β-amyloid induced the Alzheimer's disease phenotypes for Cp20.

Any immunoassay method which will tell one if the Cp20 protein level has changed will suffice. In this method antibodies that recognize the Cp20 protein are contacted with a protein sample isolated from the cells of patients being diagnosed by this assay. The formation of a complex between the Cp20 protein and antibody is detected and the change in the level of Cp20 protein between the individual being tested relative to one or more control samples is assessed.

The Cp20 diagnostic assay for Alzheimer's disease will greatly improve the complicated clinical procedure used for Alzheimer's disease because of its strong positive correlation with a diagnosis of Alzheimer's Disease. It is preferred that this assay be used in conjunction with clinical diagnosis of Alzheimer's disease or other known methods of diagnosing Alzheimer's disease. By way of example, patients or individuals who may be diagnosed as having Alzheimer's disease by this assay include individuals who have received a clinician's tentative diagnoses of Alzheimer's disease, individuals with few clinical Alzheimer's disease symptoms, individuals who have been diagnosed as having atypical dementias, and in individuals who are members of families with Alzheimer's disease. A statistically significant reduction in the level of Cp20 protein relative to control samples (healthy age-matched individuals with no familial history of Alzheimer's disease) is reasonably predictive that the patient does have Alzheimer's disease. A normal level of Cp20 protein as determined by comparison to control protein samples isolated from age matched healthy individuals with no familial history of Alzheimer's disease, indicates that the patient does not have Alzheimer's disease. One of skill in the art will appreciate that the level of Cp20 protein in the cells of a patient to be diagnosed by this assay is assessed relative to control protein samples. Control protein samples should be isolated from an adequate population sample of healthy age matched controls with no history of Alzheimer's disease in their family. By way of example, a reduction of about 40% to 60% or higher, from the control levels of Cp20, as determined by an adequate control population sample size, is indicative of Alzheimer's disease. One of skill in the art will appreciate that the sample from the patient to be diagnosed is assessed against control protein samples from healthy aged matched controls and that a significant reduction in the Cp20 level in the patient's protein sample is determined based on comparison to the controls used in the given assay.

Immunoassays of the present invention may be radioimmunoassay, Western blot assay, immunofluorescent assay, enzyme immunoassay, immuno-precipitation, chemiluminescent assay, immunohistochemical assay, dot or slot blot assay and the like. (In "Principles and Practice of Immunoassay" (1991) Christopher P. Price and David J. Neoman (eds), Stockton Press, New York, N.Y.; Ausubel et al. (eds) (1987) in "Current Protocols in Molecular Biology" John Wiley and Sons, New York, N.Y.). Detection may be by calorimetric or radioactive methods or any other conventional methods known to one skill in the art. Standard techniques known in the art for ELISA are described in *Methods in Immunodiagnosis,* 2nd Edition, Rose and Bigazzi, eds., John Wiley and Sons, New York 1980 and Campbell et al., *Methods of Immunology*, W. A. Benjamin, Inc., 1964, both of which are incorporated herein by reference. Such assays may be a direct, indirect, competitive, or noncompetitive immunoassay as described in the art (In "Principles and Practice of Immunoassay" (1991) Christopher P. Price and David J. Neoman (eds), Stockton Pres, NY, N.Y.; Oellirich, M. 1984. *J. Clin. Chem. Clin. Biochem.* 22: 895–904 Ausubel, et al. (eds.) 1987 in *Current Protocols in Molecular Biology*, John Wiley and Sons, New York, N.Y.

In this embodiment the cells taken from the patient being diagnosed may be any cell. Examples of cells that may be used include, but are not limited to, fibroblasts, buccal mucosal cells, blood cells, such as erythrocytes, lymphocytes and lymphoblastoid cells, and nerve cells and any other cell expressing the Cp20 protein. Necropsy samples and pathology samples may also be used. Tissues comprising these cells may also be used. The cells may be fresh, cultured or frozen. Protein samples isolated from the cells or tissues may be used immediately in the diagnostic assay or frozen for later use. In a preferred embodiment fibroblast cells are used. Fibroblast may be obtained by a skin punch biopsy as described above.

Proteins may be isolated from the cells by conventional methods known to one of skill in the art. In a preferred method, cells isolated from a patient are washed and pelleted in phosphate buffered saline (PBS). Pellets are then washed with "homogenization buffer" comprising 50 mM NaF, 1 mM EDTA, 1 as EGTA, 20 μg/ml leupeptin, 50 μg/ml pepstatin, 10 mM TRIS-HCl, pH=7.4, (see Example 6) and pelleted by centrifugation. The supernatant is discarded, and "homogenization buffer" is added to the pellet followed by sonication of the pellet. The protein extract may be used fresh or stored at −80° C. for later analysis.

In this method the antibodies used in the immunoassay may be monoclonal or polyclonal in origin. The Cp20 protein or portions thereof used to generate the antibodies may be from natural or recombinant sources or generated by chemical synthesis. Natural Cp20 proteins can be isolated from biological samples by conventional methods. Examples of biological samples that may be used to isolate the Cp20 protein include, but are not limited to, tissues such as squid optic lobe, Hermissenda nervous system, skin cells, such as, fibroblasts, fibroblast cell lines, such as Alzheimer's disease fibroblast cell lines and control fibroblast cell lines which are commercially available through Coriell Cell Repositories, (Camden, N.J.) and listed in the National Institute of Aging 1991 Catalog of Cell Lines, National Institute of General Medical Sciences 1992/1993 Catalog of Cell Lines [(NIH Publication 92–2011 (1992)].

By way of example, the Cp20 may be isolated from squid optic lobe by first homogenizing the tissue using standard methodologies. A preferred homogenization buffer is 10 mM Tris-HCl, pH 7.4, 20 ug/ml leupeptin, 20 ug/ml pepstatin, 50 mM NaF, 1 mM EDTA, 1 mM EGTA, 0.1 mM PMSF (phenylmethylsulfonyl-fluoride) supplemented with 200 mM DTT. (See Example 5). Isolation and purification of the protein from the homogenate can be performed by conventional chromatography techniques such as high performance liquid chromatography (HPLC) (see Example 5). Preferably, both anion and cation exchange HPLC columns are used in the purification. Additional purification steps, such as, size exclusion chromatography, ammonium sulfate precipitation, or dye affinity chromatography or any other conventional methods may also be used. Alternatively, the Cp20 protein may be purified by immunoaffinity chromatography using antibodies which recognize the Cp20 protein. Recombinant Cp20 proteins or peptides may also be used in generating Cp20 antibodies and are produced and purified by conventional methods.

Synthetic Cp20 peptides may be custom ordered or commercially made or synthesized by methods known to one skilled in the art (Merrifield, R. B. (1963) *J. Amer. Soc.* 85:2149) based on the partial amino acid sequence of the Cp20 protein provided herein (see FIG. 12A). Alternatively, the isolated Cp20 protein may be subjected to enzymatic digestion and the resulting peptides used to generate antibodies. By way of example, trypsin may be used to digest the Cp20 protein and generate peptides. One of skill in the art will appreciate that the specific trypsin digestion conditions will be dependent on the quantity of Cp20 present, and the preparation method of the Cp20 (i.e., whether it is bound to nylon membrane, nitrocellulose, or in solution, and if so what other substances are present). One skilled in the art will also know how to perform a tryptic digest of the protein and purify the fragments by HPLC or other means prior to sequence determination. An exemplary tryptic digest fragment for Cp20 is shown in FIG. 12A. If the peptide is too short to be antigenic it may be conjugated to a carrier molecule to enhance the antigenicity of the peptide. Examples of carrier molecules known to workers on the field include, but is not limited to human albumin, bovine albumin and keyhole limpet helmo-cyanin ("Basic and Clinical Immunology" (1991) Stites, D. P. and Terr A. I. (eds) Appleton and Lange, Norwalk Connecticut, San Mateo, Calif.).

Exemplary antibody molecules for use in the methods of the present invention are intact immunoglobulin molecules, substantially intact immunoglobulin molecules or those portions of an immunoglobulin molecules that contain the antigen binding site, including those portions of an immunoglobulin molecules known in the art as F(ab), F(ab'); F(ab)$_2$ and F(v). Polyclonal or monoclonal antibodies may be produced by methods known in the art. (Kohler and Milstein (1975) *Nature* 256, 495–497; Campbell "Monoclonal Antibody Technology, the Production and Characterization of Rodent and Human Hybridomas" in Burdon et al. (eds.) (1985) "Laboratory Techniques in Biochemistry and Molecular Biology," Volume 13, Elsevier Science Publishers, Amsterdam). The antibodies or antigen binding fragments may also be produced by genetic engineering. The technology for expression of both heavy and light chain genes in *E. Coli* is the subject of the PCT patent applications: publication number WO 901443, WO 901443 and WO 9014424 and in Huse et: al. (1989) *Science* 246:1275–1281. Alternatively, the Cp20 protein or peptides or portions thereof may be forwarded to a company for generation of antibodies.

The antibodies of this invention may react with native or denatured Cp20 protein or peptides. The specific immunoassay in which the antibodies are to be used will dictate which antibodies are desirable.

By way of example, the isolated Cp20 or portions thereof may be injected into the spleen cells of mice for generating monoclonal antibodies. The spleens are fused to hybridoma cells, the desired clones selected and the monoclonal antibodies generated and purified by methods known to one skilled in the art. (Ausubel et al. (eds) 1987". Current Protocols in Molecular Biology" John Wiley and Sons, New York, N.Y.).

Polyclonal antibodies may also be generated using the Cp20 protein or portions or peptides thereof by standard methods. By way of example, peptides derived from the Cp20 partial amino acid sequence shown in FIG. 12A (single letter code) may be used. For example, the peptide ARLW-TEYFVIIDDDC (SEQ. ID. NO. 9), derived from the partial amino acid sequence (FIG. 12A) may be synthesized by standard methods. Using conventional methods, rabbits may be immunized with this Cp20 peptide preferably conjugated with hemo-limpet hemocyanin. One skilled in the art will appreciate that if a synthetic peptide is used, a cysteine group is added to the C-terminal to facilitate conjugation. Preferably about 0.2 to 1.0 milligrams (mg) of the peptide-antigen in Freund's complete adjuvant is used for the initial injection. The animal receives similar booster doses in incomplete adjuvant thereafter and antisera titer is assessed by ELISA assay. Satisfactory levels ok antisera are obtained when the antipeptide antibody titer reaches a plateau. This antibody can be used in the diagnostic immunoassay described above. Alternatively, shorter peptide sequences derived from the Cp20 amino acid sequence presented in FIG. 12A, or the entire Cp20 amino acid sequence shown in FIG. 12A, may also be used to immunize animals for the generation of both monoclonal and polyclonal antibodies.

In a preferred embodiment antibodies that recognize the Cp20 protein are used to detect the protein in Western Blot Analysis comparing protein samples isolated from the cells of the patient to be diagnosed by the assay and protein samples from healthy age-matched control individuals with no history of Alzheimer's disease in their family. The levels of Cp20 protein in the patient samples versus the control samples can be assessed visually or by using standard densitometric scanning techniques. Commercially available computer programs are available for densitometric analysis. Control cell lines are also commercially available through Coriell Cell Repositories (Camden, N.J.).

The predicted Cp20 is about a 20 kilodalton protein with structural and biochemical features that identify it as a member of the ARF family of proteins. The Cp20 protein also exists in the form of a dimer of about 40 kD and depending on the conditions used in an assay can appear as a monomer or dimer. A partial amino acid sequence for Cp20 is shown in FIG. 12A. This invention therefore also relates to a Cp20 protein comprising the amino acid sequence shown in FIG. 12A and more specifically relates to the Cp20 peptide sequence shown in FIG. 12A. This invention is also intended to encompass protein or peptides substantially homologous to the Cp20 protein and having substantially the same function as the Cp20 protein of this invention.

This invention also relates to expression vectors for producing recombinant Cp20 protein comprising a nucleic acid sequence for Cp20 an, a vector for expressing all or part of the Cp20 protein. Standard methodology can be used to derive nucleic acid sequences based on the partial amino acid sequence shown in FIG. 12A for incorporation into such expression vectors. One skilled in the art will know how to utilize currently extant cDNA library screening techniques or various techniques involving PCR (polymerase chain reaction) for obtaining the corresponding DNA sequence from the partial amino acid sequence shown in FIG. 12A, and for incorporating the DNA sequence into a suitable expression vector. Further, one of skill in the art will know the correct combination of operational elements to incorporate into such vectors and that such vectors are easily constructed using conventional methods (Ausubel et al. (1987), in "Current Protocols in Molecular Biology" John Wiley and Sons, New York). The Cp20 amino and sequence provided herein can also be used to obtain homologs of Cp20 from other species by methods known to one skilled in the art.

This invention also relates to kits which can be utilized in performing the diagnostic assay. Such a kit would comprise antibodies which recognize the Cp20 protein. Such antibodies may be polyclonal or monoclonal. The kit may also contain instructions relating to the use of these antibodies in diagnostic assays. The kit may also contain other reagents for carrying out the assay such as buffers, secondary antibodies and the like.

The fifth embodiment of this invention is based on the discovery by the inventors that β-amyloid protein, the major constituent of neuritic plaques, differentially alters levels of PKCα and PKCγ in fibroblasts from Alzheimer's patients versus fibroblasts from healthy donors. These differential effects of β-amyloid on levels of PKC isoenzymes in Alzheimer's disease cells and healthy cells therefore represent yet another method for diagnosing Alzheimer's disease.

In this method, the levels of PKCα and PKCγ isozymes in untreated and β-amyloid-treated cells of the individual being tested are assessed with an observed reduction in the level of PKCγ protein and/or an insignificant reduction in the level of PKCα protein in β-amyloid treated cells relative to the non-treated controls being reasonably predicative that the patient has Alzheimer's disease. Conversely, a reduction in the level of PKCα protein, but not PKCγ, in β-amyloid treated cells indicates that the patient does not have Alzheimer's disease.

One of skill in the art will appreciate that by way of example, a reduction of PKCγ of about 45% to about 70%, in β-amyloid treated cells relative to the levels in untreated cells of the same patient:, as determined by an adequate control population sample size, is indicative of Alzheimer's disease. Alternatively, an insignificant change in the level of PKCα in β-amyloid treated cells S relative to untreated cells, is also indicative of Alzheimer's disease.

For practicing this method, any immunoassay method will suffice which will tell one if the level of the relevant PKC isoenzymes has changed in untreated cells relative to cells treated with β-amyloid. For example, suitable immunoassays may be those described above for detecting Cp20 protein.

The antibodies used in the immunoassay may be monoclonal or polyclonal in origin. In one embodiment, the PKCα and PKCγ protein or portions thereof may be used to generate the antibodies and the PKC isozymes or portions thereof may be from natural or recombinant sources or generated by chemical synthesis. Alternatively, antibodies that specifically recognize the PKCα or the PKCγ proteins are commercially available. For a preferred embodiment, the antibodies are monoclonal antibodies.

As used in this method, "β-amyloid protein" refers to the intact protein or peptide fragments thereof. The β-amyloid protein or peptide fragments thereof which are used to treat cells may be generated recombinantly, by chemical synthesis, or may be purified from biological samples by conventional methods. Examples of biological samples that may be used to isolate the β-amyloid protein include, but are not limited to, tissues such as skin fibroblasts, blood cells, olfactory epithelium and brain biopsy. Where the β-amyloid proteins are produced recombinantly or by chemical synthesis, it is preferred that the protein be purified prior Ho use in the above described method. In a preferred embodiment, synthetic β-amyloid peptides are used.

Concentrations of β-amyloid protein to be utilized in the method range from about 1 nM to about 1 FM with a preferred concentration being about 10 nM. Preferably, cells are treated for at least 24 hours, more preferably for at least 48 hours, with a concentration of β-amyloid protein effective to affect a reduction in PKCγ immunoreactivity in AD cells.

In this method, the cells to be analyzed may be any cells taken from the patient being diagnosed. Examples of cells that may be used include, but are not limited to, fibroblasts, buccal mucosal cells, blood cells, such as erythrocytes, lymphocytes and lymphoblastoid cells, such as erythrocytes, lymphocytes and lymphoblastoid cells, and nerve cells and any other cell expressing the PKCα and PKCγ proteins. Necropsy samples and pathology samples may also be used. Tissues comprising these cells may also be used. The cells may be fresh, cultured or frozen. Protein samples isolated from the cells or tissues may be used immediately in the diagnostic assay or frozen for later use. In a preferred embodiment fibroblast cells are used. Fibroblasts may be obtained by a skin punch biopsy as described above.

Protein samples to be analyzed for PKC isozyme expression may be isolated from the cells by conventional methods known to one of skill in the art. The protein sample may be used fresh or stored at $-80°$ C. for later analysis. In a preferred method, the protein sample is isolated from a patient's fibroblast cells as described in Example 8.

It is understood by those of skill in the art that this method may be used in conjunction with clinical diagnosis of Alzheimer's disease or other known methods of diagnosing Alzheimer's disease.

For yet another embodiment of this invention, europium (III) thenoyltrifluoro-acetonate (Eu-TTA) fluorescence imaging, a thermal imaging method that images the metabolic heat signals generated by ligand-receptor interactions in cells, is used to detect differences in intracellular heat production between normal and AD cells following treatment with an activator of a receptor-mediated metabolic pathway.

In this embodiment of the invention, the cells are first stained with from 1 $\mu$M to 100 $\mu$M Eu-TTA, preferably 50 $\mu$M Eu-TTA, for at least 10 to 50 minutes, preferably 30 minutes, and then contacted with an activator of a receptor-mediated metabolic pathway. Normally, no fluorescence is observed in untreated cells. Treatment with an activator of a receptor leads to intracellular heat production which is measured by recording the fluorescence intensity (of activator-treated cells at two different bath perfusion temperatures and calculating the ratio of the two recordings.

By "activator of a receptor-mediated metabolic pathway" is meant any molecule that may interact with a receptor and includes proteins or peptides (naturally occurring or synthesized recombinantly or chemically), inorganic molecules, antibodies and oligonucleotides. Examples of activators that may be used in this method include, but are not limited to, bradykinin, bombesin, and all other agents for which receptors exist on the surface of the cells of choice to be assayed. A preferred activator is bradykinin. Of course, one could readily test for other receptor-mediated metabolic pathways that are altered in Alzheimer's cells by treating cells from a patient with a molecule known to activate that pathway and comparing the intensity of activator-treated patient cells with the staining intensity observed in activator-treated cells from a healthy donor.

Example 9 exemplifies this embodiment of the invention for diagnosing AD by measuring Eu-TTA fluorescence in AD and normal cells ir response to bradykinin, a molecule known to activate receptor-mediated phosphoinositide cascade and induce $IP_3$-mediated calcium release. As shown in Example 9, Eu-TTA fluorescence in response to bradykinin is more intense in Alzheimer's cells than that of the control cells. Alzheimer-specific differences may also be measured within restricted regions or compartments inside the cells of choice such as the endoplasmic reticulum. It is understood that other methods for measuring heat changes generated by ligand-receptor interactions in cells can also be used to distinguish Alzheimer's cells from normal cells.

Of course, one of skill in the art would realize that Eu-TTA fluorescence might also be less intense in activator-treated AD cells relative to activator-treated cells from a healthy donor. For example, one can envision that in the case in which one or more steps of a receptor activated pathway is diminished or absent in AD cells, Eu-TTA fluorescence intensity in response to the activator of that pathway would be decreased in Alzheimer's cells compared to that of normal cells. Therefore, any change in Eu-TTA fluorescence intensity in a patient's cells, either an increase or a decrease, relative to the fluorescence observed in cells from a healthy donor would indicate the presence of Alzheimer's disease. On the other hand, Bu-TTA fluorescence which is of a similar intensity in normal cells and the cells of the patient would indicate the absence of Alzheimer's disease in the patient.

As the Eu-TTA fluorescence diagnostic assay monitors membrane signal transduction abnormalities of Alzheimer's disease cells that may have been manifested through measures of downstream molecular and biophysical events such as $K^+$ channel function and $IP_3$-mediated calcium release, this method may be used in conjunction with other known methods of diagnosing Alzheimer's disease such as those encompassed by the other diagnostic methods of this invention.

In yet another embodiment, this invention is also intended to encompass defects ill any of the steps in the calcium signalling pathway shown in FIG. 27 that may exist in Alzheimer's cells relative to cells from a healthy donor. Indeed, based on the data presented herein demonstrating that a number of the steps of the calcium signaling cascade are defective in Alzheimer's disease cells thereby supporting the notion that calcium homeostasis is involved in the patholphysiology of Alzheimer's disease, it is believed that additional defects in the steps of the calcium signaling pathway illustrated in FIG. 27 are likely to exist in Alzheimer's cells. Thus, since the molecular and biophysical events involved in the cascade illustrated in FIG. 27 include intracellular calcium elevation, $K^+$ channel inactivation, PKC-mediated phosphorylation of Cp20 (also referred to as CE), Cp20-ryanodine receptor-mediated release of calcium, Cp20-mediated enhancement of MRNA turnover, increased expression of type-2 ryanodine receptor, and semi-permanent reduction of dendritic voltage-dependent $K^+$ channels, it is possible to compare the various events involved in the pathway in Alzheimer's and control cells in order to determine whether they are altered in Alzheimer's cells relative to controls.

For example, Cp20 inactivation of $K^+$ channels, an event occurring in time domain 1 of FIG. 27, could be assessed by comparing single-channel current traces of $K^+$ channel activity upon Cp20 stimulation of Alzheimer's disease cells and cells from a healthy donor. Alternatively, Cp20 binding to the ryanodine receptor (Ryr), an event occurring in time domain 2, could be assessed using antibodies to Cp20 and Ryr. In addition, increased Ryr expression, an event occurring in time domain 5, could be assessed by comparing changes in Ryr MRNA level following membrane depolarization in Alzheimer's disease cells relative to control cells.

In yet another embodiment of this invention a diagnostic index for diagnosing Alzheimer's is provided which integrates two or more tests for diagnosing Alzheimer's disease thereby providing a scoring system to be used in distinguishing AD cells from non-AD cells. Examples of the diagnostic tests that may be integrated to generate the diagnostic index include, but are not limited to, the diagnostic methods described herein, including detecting the absence of the 113 ps potassium ion channel in the cells of an Alzheimer disease patient, detecting differences in intracellular calcium Lon concentration in AD and non-AD cells in response to potassium channel blocker specific for the potassium ion channel that is absent in AD cells, differences between AD and non-AD cells in response to activators of intracellular calcium release and reduction in the levels of a memory associated GTP-binding protein (cp20) in the cells of an AD patient. Preferably at least two diagnostic tests are used in generating the index, most preferably three diagnostic tests are used in generating the index. The two or more diagnostic tests used in generating the index can assess the same alteration in AD versus non AD cells or different alterations in AD versus non-AD cells.

By way of example the diagnostic tests used to generate the scoring system for the index may comprise three diagnostic tests: one test may assess the differences in intracellular calcium ion concentration in AD versus non AD cells in response to a potassium ion channel blocker, and two tests may assess the differences in intracellular calcium release in AD versus non AD cells in response to two different activators of intracellular calcium release. By way of example TEA can be the potassium ion channel blocker and the activators of intracellular calcium release may be bombesin or bradykinin.

One of skill in the art recognizes that for an individual test statistical analysis can be performed on a reference or normative population sample of cells to determine confidence levels of having Alzheimer's disease based on the results of that test. Accordingly for each test, a scale can be arbitrarily partitioned into regions having scores such that a correct combination of the scores provides a diagnostic index having a certain degree of confidence. The partioning can be performed by conventional classification methodology including, but not limited to, histogram analysis of thus cells or cell lines used in performing the test, multivariable regression or other typical analysis or classification techniques. For example, one skilled in the art recognizes that multi-variable regression analysis may be performed to generate this partitioning or to analyze empirical/arbitrary partitioning in order to determine whether the composite clinical index has a higher degree of significance than each of the individual indices from respective tests.

It is preferable that each test be performed to maximize the differences between AD versus non-AD cells being assessed. By way of example parameters that can be manipulated to maximize differences between AD versus non-AD cells include, but are not limited to, concentration of the drug or reagent being used in the test, latency of the response, amount of the Cp20 protein or the phosphorylation state of the protein.

By way of example a diagnostic index can be generated by integrating the scored results, values or signals from a test assessing release of intracellular calcium levels in AD versus non AD in response to bradykinin, a test assessing release of intracellular calcium in AD versus non-AD cells in response to bombesin, and a test assessing potassium channel function in AD versus non-AD cells after exposure to TEA (See Examples 2, 3 and 7). By way of example, the partitioning or classification of the response may be based on the percentage of cells responding in the given test and/or the magnitude of the integrated area of the response. By way of example, in a diagnostic test utilizing bombesin, if the time-integrated calcium ($Ca^{2+}$) concentration is <23000 nanomolar (nM)-seconds (sec) then zero is assigned as the score. For each test a reference or normative sample population was evaluated, partioned to maximize confidence levels and scored. A sample clinical index is provided below:

| Treatment | Response | Score |
|---|---|---|
| Bradykinin (0.1 nm) | <1.5% responding cells | 0 (no response) |
| (Latency of the onset ≦ 135 sec) | ≧1.5% responding cells | −0.5 |
| | ≧4.0% responding cells | −1.0 |
| TEA (100 mM) | <5% responding cells | 0 (no response) |
| (Latency of the onset ≦ 60 sec) | ≧5% responding cells | 0.5 |
| | ≧16% responding cells | 1.0 |
| Bombesin* (1 μm) | <50% responding cells or area < 23000 nM-sec | 0 (no response) |
| (Latency of the onset ≦ 40 sec) | ≧50% responding cells and area ≧ 23000 nM-sec | −0.5 |
| | ≧50% responding cells and area ≧ 30000 nM-sec | −1.0 |

*Calcium free media

If the above sample diagnostic index is used, it is preferable that a 0.1 nM concentration of bradykinin be used in the given diagnostic test, and that the response be measured within a period of 135 seconds or less. For TEA it is preferable that a 100 mM concentration be used in a given test and that the response be measured within a period of 60 seconds or less. For bombesin it is preferable that a 1 μM concentration be used in a given test and that the response be measured in a period of 40 seconds or less. For bombesin the integrated area is in units of nanomolar (nM) calcium concentration-seconds (sec.).

A net positive score is indicative of non-AD, whereas a net negative score is indicative of AD. One of skill in the art will appreciate that the scoring numbers may be scaled or biased.

This invention also includes a sample scoring system for Alzheimer's disease and a means for providing a signal corresponding to the first diagnostic test, the second diagnostic test and any additional tests. This invention further provides a means for combining the respective signals into a composite score. These means may be implemented in accordance with known signal or data acquisition apparatus and techniques indicating software operating on a conventional computer.

All books, articles, or patents referenced herein are incorporated by reference. The present invention will now be described by way of examples, which are meant to illustrate, but not limit, the scope of the invention.

EXAMPLE 1

Patch-clamp Diagnostic Test

Cultured skin fibroblasts (described in Table 3) from the Coriell Cell Repositories (Camden, N.J.) were grown under highly standardized conditions. Cristafallo, V. J. and Chapentier, R. J. (1980) *Tissue Culture Methods* 6:117. The following cell lines were used for the experiments: Young Control Fibroblasts ("YC") 3652, 3651, 2987, 4390, 3377, 8399 (21.5±2.8 years, Mean±S.D); Age-matched Control Fibroblasts ("AC") 3524, 6010, 6842, 7603, 9878 (65.2±6.0 years); and Alzheimer's Disease Fibroblasts ("AD") 6848, 7637, 5809, 8170, 6840, 8243, 6263 (60.6±6.8 years). Five AD lines were from familial patients. Some of the lines (2 AC and 4 AD) were from Canadian kindred.

In agreement with the literature, the data indicate the time to phase out does not vary between the AD and control lines (YC and AC). (Cells were seeded (approximately 5 cells per $mm^2$) in 35 mm Nunc petri dishes in Dulbecco's Modified Eagle Medium (DMEM, Gibco), supplemented with 10% fetal calf serum and used when cell density was equivalent for all cell lines, between days 2 and 4 after plating. On average, fibroblasts from AD patients and controls took the same time to reach erosion density (50 cells/$mm^2$).

Patch-clamp experiments were performed at room temperature (21–23° C.), following standard procedures set forth in Sakmann, B. and Neher, E. (1983) *Single Channels Recordings* (Plenum New York) and Kukuljan, M., et al. (1991) *J. Membrane Biol.* 119:187. Before recordings, culture medium was replaced with the following solution: 150 mM NaCl, 5 mM KCl, 2 mM $CaCl_2$, 1 mM $MgCl_2$, 10 mM HEPES (NaCl) pH=7.4. Pipettes were made from Blue Tip capillary tubes (I.D. 1.1–1.2 mm) using a BB-CH Mecanex puller, and then filled with a high potassium solution of 140 mM KCl, 2 mM $CaCl_2$, 1 mM $MgCl_2$, 10 nM HEPES (NaOH), pH=7.4. Pipette resistances were approximately 6 MΩ. Records were obtained using an Axopatch-IC amplifier (dc-10 kHz), stored on tape (Toshiba PCM-video recorder), and later transferred to a personal computer using an Axolab interface. Only recordings lasting for at least 3 minutes were considered for final analysis. The pClamp suite of programs was used for single-channel data acquisition and analysis. Amplifier, interface and software were obtained from Axon Instruments (Foster City, Calif.).

In the cell-attached mode, two types of potassium channels were recorded from human skin fibroblasts. Since pipettes were filled with a high potassium solution, potassium currents were inward as expected, and their reversal potential approximately corresponded to the cell resting potential. A potassium channel (113 pS) of approximately 4.5 pA unitary current size (0 mV pipette potential), with identical kinetics appeared in YC and AC fibroblasts, but was entirely absent in the recording of AD fibroblasts (FIG. 1A). Downward deflections represent the open state. I/V relationships of the same channels in FIG. 1A (FIG. 1B) and slope conductances (determined by linear regression) were almost identical within the voltage range explored, 113.2±0.9 pS (Mean±S.D., n=8)) for YC and 112.9±3.2 pS (n=7) for AC fibroblasts.

A second channel (166 pS) was recorded under the same conditions from fibroblasts of all three groups (FIG. 2A). I/V relations (FIG. 2B) as well as conductance (YC=173.4±5.7 pS, n=4; AC=169.2±2.8 pS, n=4; AD=157.6±4.7 PS, n=6 (Mean±S.D.)) were approximately the same across groups. Membrane potential was similar in control (−42.6±5.4, Mean±S.D., n=7) and in AD (−45.4±6.9, n=3) fibroblasts.

Both channels had linear voltage-current relationships, with slope conductances of 113 pS and 166 pS respectively (FIGS. 1A–B and 2A–2B). At 0 mV pipette potential, the channels could easily be identified by their unitary current size (FIGS. 1A and 2A) and by their percentages of open time, approximately 60% for the 113 PS $K^+$ channel and approximately 10% for the 166 pS $K^+$ channel. For both channels, the percentages of open time showed no significant voltage-dependence (+60 to −40 mV pipette potential). The 113 pS $K^+$ channel was found in 47% of YC cells (n=30) and 94% of the AC cells (n=17), while it was never found in AD fibroblasts (n=24) ($\chi^2$=18.96, p<0.001 (Table 1)). There were no AD cell lines (N=6) that had fibroblasts with an observable 113 pS channel. By contrast, all AC cell lines (N=5) and three of six YC cell lines had fibroblasts with observable 113 pS channels ($\chi^2$=11.93, p<0.005 (Table 2)). The 166 pS channel found was similar frequency in all three groups ($\chi^2$=0.89, N.S. (Tables 1 and 2)).

The 113 pS channel found to be "absent" in the AD fibroblasts, could be present but not functional. Such dysfunction could involve structural changes in the channel and/or alteration in processes involved in channel activity regulation.

Using cell-free patches, following the method described above, it was observed that both channels were sensitive to 50 mM $Ba^{2+}$ (inside-out, n=4 for each channel), but only the 113 pS channel was sensitive (outside-out, n=4 YC, n=3 AC) to the $K^+$ channel blocker tetraethylammonium (TEA). The TEA-blockade of the 113 pS channels (possibly together with other channels) significantly affects membrane potential since control cells (n=4) depolarized 13–20 mV after 100 mM TEA addition.

TABLE 1

Number of Cells

| Condition | Total | 113 pS $K^+$ Channel | 166 pS $K^+$ Channel |
|---|---|---|---|
| Young Controls | 30 | 14 (47%) | 6 (20%) |
| Aged Controls | 17 | 16 (94%) | 6 (35%) |
| Alzheimer Patients | 24 | 0 (0%) | 8 (33%) |

TABLE 2

Number of Cell Lines

| Condition | Total | 113 pS $K^+$ Channel | 166 pS $K^+$ Channel |
|---|---|---|---|
| Young Controls | 6 | 3 | 4 |
| Aged Controls | 5 | 5 | 3 |
| Alzheimer Patients | 7 | 0 | 4 |

When using control cells, it is best to use age-matched control cells.

EXAMPLE 2

TEA-$Ca^{2+}$ Diagnostic Test

Cultured skin fibroblasts (described in Table 3) from the Coriell Cell Repositories (Camden, N.J.) were grown as described in Example 1.

Thirteen AD, ten AC, and six YC were used for the calcium-imaging experiments. Culture medium was replaced and washed three times with basal salt solution ("BSS") consisting of 140 mM NaCl, 5 mM KCl, 2.5 mM $CaCl_2$, 1.5 mM $MgCl_2$, 5 mM glucose, 10 mM HEPES (NaOH), pH 7.4. Nominally $Ca^{2+}$ free BSS was prepared as BSS without adding $CaCl_2$.

Fura-2 (acetyloxymethyl ester) (Fura-2 AM) was purchased from Molecular Probes (Eugene, OR) and stored as a 1 mM solution in dimethylsulfoxide. Fura-2 AM was added to a final concentration of 2 $\mu$M and cells were incubated at room temperature (21°–23° C.) for 60 minutes. After incubation, cells were washed at least three times with BSS at room temperature before $[Ca^{2+}]_i$ determinations. Fluorescence was measured with a Hamamatsu ARGUS 50 imaging system (Hamamatsu Photonics, Japan) under the control of a personal computer (Hamamatsu imaging software package). Excitation at 340 nm and 380 nm was attenuated with neutral density filters. Fluorescent images were obtained with a 400 nm dichroic mirror and a 510 nm long-pass barrier filter. The objective lens was an X10 Nikon UV fluor. Fluorescence was measured within a uniformly illuminated fraction ¼ of the whole image.

The averaged $Ca^{2+}$ responses within 15×15 pixels in cytosolic and in nuclear cellular compartments obtained were quantified with ratios between emitted 510 nm fluorescence activated at 340 nm and fluorescence emitted at 510 nm with activation at 380 nm. These ratios were transformed to absolute values of [Ca2+], after calibration based on the following equation:

$$R \pm R_{max} + (R_{min} - R_{max})/(1 + ([Ca^{2+}]_i/Kd)^b).$$

Here R denotes fluorescence intensity illuminated by 340 nm divided by fluorescence intensity illuminated by 380 nm (F340/F380), and $R_{max}$ and $R_{min}$ are the values of R when the concentration of calcium is at a maximum and a minimum (i.e., the maximum and minimum value measurable by the machine under the measuring conditions), respectively. Kd is a dissociation constant of fura-2 for $Ca^{2+}$ and was determined as 240 nM. The value of b, which determined the degree of asymmetry, was 1.2. TEA application caused a minimum of 100% $[Ca^{+2}]_i$ elevation in at least 18% of cells in every control cell line except one young control. A response of 100% $[Ca^{+2}]_i$ elevation in at least 10% of cells in a line was, therefore, considered to be a conservative criterion for a positive response. Only one AD cell line had cells with any response (100% $[Ca^{+2}]_i$ elevation in 4% of cells), well below the criterion).

Figure 3B:
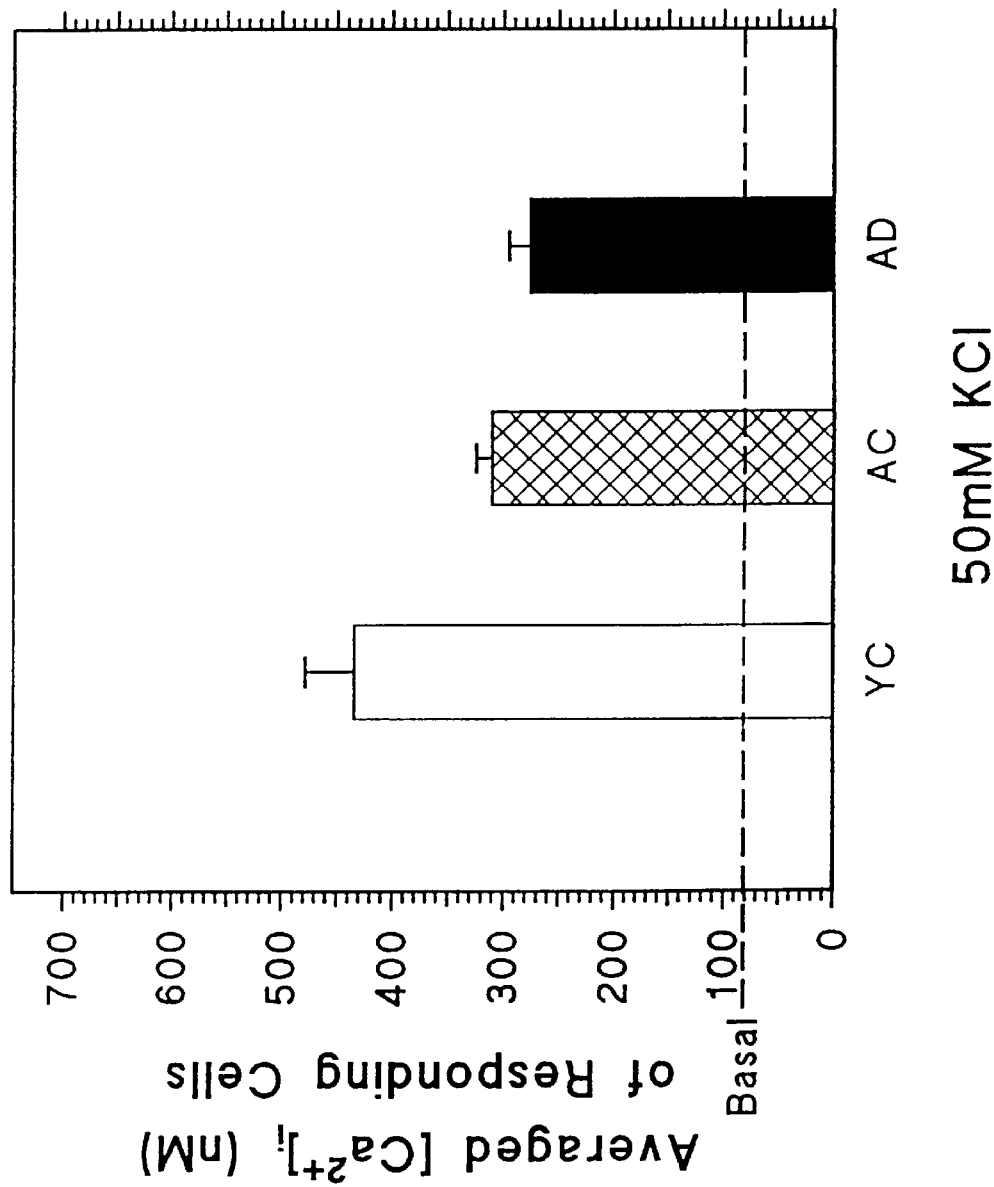

Depolarization of the fibroblasts by perfusion in elevated external potassium caused greater elevation of intracellular $Ca^{2+}$ ($[Ca^{2+}]_i$) in YC as compared to AC and AD cells (FIGS. 3A–3C). This depolarization-induced $[Ca^{2+}]_i$ elevation was eliminated by lowering external calcium or by adding calcium channel blockers (FIG. 3C). High $K^+$-induced depolarization caused a marked $[Ca^{2+}]_i$ elevation (at least 100% increase) in all three groups (AD, n=13 cell lines; AC, n=10; YC, n=6). The proportion of responding cells and the $[Ca^{2+}]_i$ peak values were significantly higher in YC (n=183 cells) fibroblasts ($\chi^2$=14.22, p<0.001), as compared to AC (n=299) and AD (n=268) fibroblasts. The $[Ca^{2+}]_i$ peak occurs 10 to 15 seconds after stimulation, returning to basal levels after 100 seconds. No responses were observed if external calcium was lowered by addition of "riominally $Ca^{2+}$ free" solution or 5 mM EGTA (estimated free $Ca^{2+}$=0.04 $\mu$M) or $Ca^{2+}$ channel blockers (0.1 mM $LaCl_3$, 10 MM $CoCl_2$, 10 mM $NiCl_2$, 10 mM $CdCl_2$ or 10 $\mu$M nifedipine) before stimulation.

Depolarization of control fibroblasts by TEA also caused $[Ca^{2+}]_i$ elevation, that was eliminated by lowering external calcium or by adding calcium channel blockers. AD fibroblasts, however, only showed $[Ca^{2+}]_i$ elevation in elevated external potassium and had no $[Ca^{2+}]_i$ response with addition of even 100 mM TEA. Every AC cell line (N=10) and all but one YC cell line (N=6) had cells responding to TEA, while none of the thirteen AD cell lines examined had cells responding to 100 mM TEA ($\chi^2$=25.66, p<0.001) (Tables 3 and 5)

TABLE 3

Number of Cell Lines

| Condition | Total | Increase in $[Ca^{+2}]_i$ with 100 mM TEA |
|---|---|---|
| Young Controls | 6 | 5 |
| Aged Controls | 10 | 10 |
| Alzheimer's Patients | 13 | 0 |

Figure 4B:
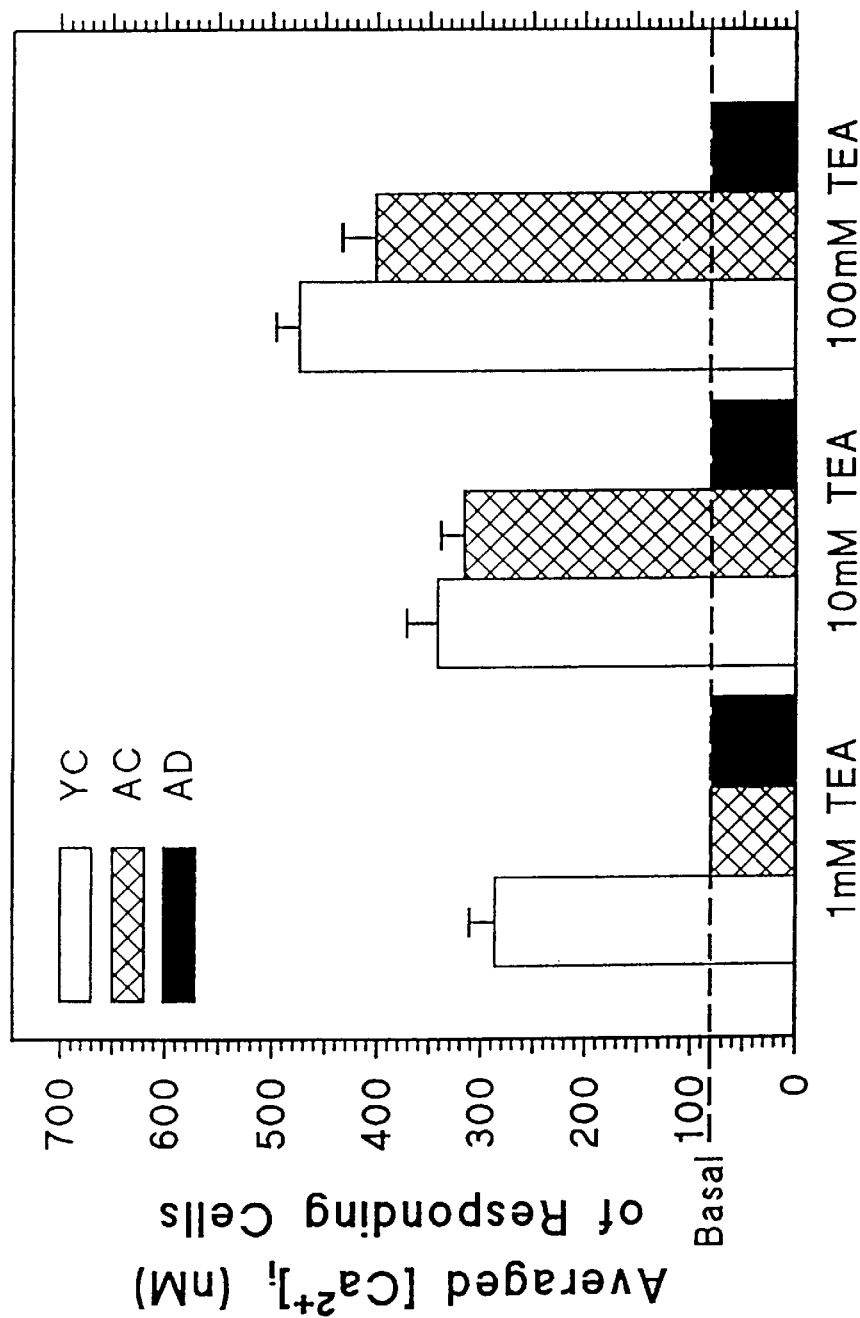

1 mM TEA application elevated $[Ca^{2+}]_i$ in YC fibroblasts (n=130 cells) but not in AC (n=184) or AD (n=195) fibroblasts. 10 mM TEA elevated $[Ca^{2+}]_i$ in YC (n=176) and AC (n=231) but not in AD fibroblasts (n=204). Similarly 100 mM TEA elevated $[Ca^{2+}]_i$ in YC (n=532) and AC (n=417), but not in AD fibroblasts (n=738) ($\chi^2$=231.44, p<0.001). At least 417 cells were explored in each experimental group (Table 4). The $[Ca^{2+}]_i$ values of the responding cell were similar in YC and AC cells after 10 and 100 mM TEA addition. Basal $[Ca^{2+}]_i$ levels were virtually the same (S.E.<0.5 n), therefore standard error bars are not distinguishable from the bar representing the arithmetic mean for those groups (FIG. 4B). Time courses of $Ca^{+2}$ response shows that the $[Ca^{2+}]_i$ peak occurs 20 to 30 seconds, after 100 mM TEA addition in YC and AC fibroblasts, returning to basal levels after 100 seconds. No response was observed in AD cells (10% of cells in a line with $\geq$100% elevation). Similarly, the response was absent in control cells when external $[Ca^{2+}]$ was lowered (FIG. 4C).

TABLE 4

| | Number of Cells | |
|---|---|---|
| Condition | Total | Increase in $[Ca^{+2}]_i$ with 100 mM TEA |
| Young Controls | 532 | 145 (27%) |
| Aged Controls | 417 | 119 (29%) |
| Alzheimer's Patients | 738 | 4 (0.5%) |

TEA-induced $[Ca^{2+}]_i$ elevations were repeated using a coded subsample that included Alzheimer's and control fibroblasts. Experiments and analyses were conducted without the experimenter's knowledge of the cell lines identity. The results were in complete agreement with the non-blind sample. None of the blindly examined AD cell lines (N=11) showed $[Ca^{2+}]_i$ elevation in response to TEA and all but one of the control cell lines (4 AC and 6 YC) had TEA responses ($\chi^2$=17.33, p<0.001 (Table 5)).

Since $[Ca^{2+}]_i$ elevation in response to high potassium was virtually the same for AC and AD cells, the lack of AD cells response to TEA is almost certainly due to dysfunction of $K^+$ channels and not to $Ca^{2+}$ channel dysfunction.

The $[Ca^{2+}]_i$ measurements are in agreement with the patch-clamp measurements insofar as they both indicate potassium channel dysfunction in the AD fibroblasts. See Table 5.

TABLE 5

| | | | | | TEA Response | |
|---|---|---|---|---|---|---|
| Line # | Age | Gender | Race | Diag. Criteria | 113 K+ Channel | Non Blind | Blind |

Alzheimer's Disease Fibroblasts

| Line # | Age | Gender | Race | Diag. Criteria | 113 K+ Channel | Non Blind | Blind |
|---|---|---|---|---|---|---|---|
| AG06840+[1] | 56 | M | W | Clinical - Fam. H. | – | – | – |
| AG06848+[2] | 55 | F | W | Clinical - Fam. H.* | – | – | N.T. |
| AG07637+ | 55 | F | W | Clinical - Fam. H. | – | – | – |
| AG08170+ | 56 | M | W | Clinical - Fam. H. | – | – | – |
| AG06844+ | 59 | M | W | Clinical - Fam. H.* | N.T. | N.T. | – |
| AG04400‡ | 61 | F | W | Clinical - Fam. H. | N.T. | N.T. | – |
| AG04401‡ | 53 | F | W | Clinical - Fam. H.* | N.T. | – | – |
| AG05809 | 63 | F | W | Clinical - Fam. H. | – | – | N.T. |
| AG08243 | 72 | M | W | Clinical - No Fam. H. | – | – | – |
| AG07375 | 71 | M | W | Clinical - No Fam. H. | N.T. | – | – |
| AG07376 | 59 | M | W | Clinical - No Fam. H. | N.T. | – | – |
| AG06263 | 67 | F | W | Clinical - No Fam. H. | – | – | – |
| AG07377 | 59 | M | W | Clinical - No Fam. H. | N.T. | N.T. | – |

Age-Matched Control Fibroblasts

| Line # | Age | Gender | Race | Diag. Criteria | 113 K+ Channel | Non Blind | Blind |
|---|---|---|---|---|---|---|---|
| GM03524 | 67 | F | B | Normal | + | + | N.T. |
| AG06010 | 62 | F | W | Normal | + | + | + |
| AG06842+ | 75 | M | W | Normal - Fam. H. | + | N.T. | N.T. |
| AG07603+ | 61 | F | W | Normal - Fam. H. | + | + | N.T. |
| AG09878 | 61 | F | B | Normal | + | + | + |
| AG08044 | 58 | F | B | Normal | N.T. | + | N.T. |
| AG6241 | 61 | M | W | Normal | N.T. | + | N.T. |
| AG4560 | 59 | M | W | Normal | N.T. | + | N.T. |
| GM04260 | 60 | M | W | Normal | N.T. | + | N.T. |
| AG07141 | 66 | F | W | Normal | N.T. | N.T. | + |
| AG11363 | 74 | F | W | Normal | N.T. | N.T. | + |

Young Control Fibroblasts

| Line # | Age | Gender | Race | Diag. Criteria | 113 K+ Channel | Non Blind | Blind |
|---|---|---|---|---|---|---|---|
| GM03652 | 24 | M | W | Normal | + | + | + |
| GM03651 | 25 | F | W | Normal | + | + | + |
| GM02987 | 19 | M | W | Normal | – | – | – |
| GM04390 | 23 | F | W | Normal | + | + | + |
| GM03377 | 19 | M | W | Normal | – | + | + |
| GM08399 | 19 | F | ? | Normal | – | + | + |

Alzheimer's fibroblasts were from familial (N=8) and non-familial cases (N=5). Five (+) are members of the Canadian family 964, only 1 and 2 are immediate relatives (sibs). "‡" are members (sibs) of family 747. Autopsy confirmed Alzheimer's diseases in three cases (*). Two of the age-matched control (N=11) cell lines are unaffected members of the Canadian family (964). All young control lines (N=6) are from normal and without AD family history individuals. Criterion $[Ca^{2+}]_i$ responses (to 100 mM TEA), indicates as +, werea observed in all AC lines used and in all but one of the YC lines. The presence of the 113 pS $K^+$ channel is indicated by the "+" sign. None of the AD lines exhibited "positive" response. A blind protocol was conducted to measure TEA responses in Alzheimer's (N=11) and control (YC=6, AC=4) fibroblasts. The results exactly reproduced those of the non-blind sample: no AD cells line exhibited TEA responses and 9 out 10 control cells showed TEA responses, $x^2$=17.33, p<0.001. The notation "N.T." indicates cell line/conditions that were not tested.

EXAMPLE 3

Bombesin—$Ca^{2+}$ Diagnostic Test

Human skin fibroblasts listed in Table 3 were used. The average age for the AD cell lines used is 60.5±5.9 years; for the AC cell lines is 62.3±9.6 years; and for the YC cell lines is 21.5±2.2 years. The method of maintenance for the cells was described in Example 1, i.e., maintained 3–5 days at 37° C. in $CO_2$/air (5%/95%) to reach a density of 50 cells/mm² before calcium measurements. The number of culture passages were less than 19.

Bombesin was purchased from Calbiochem (San Diego, Calif.). Bombesin was stored as a 1 mM solution in distilled water. Fura-2 (acetyloxymethyl ester), fura-2 (pentapotassium salt) and omega-condtoxin ($\omega$-CgTX) GVIA were from Molecular Probes (Eugene, Oreg.). Fura-2 AM was stored as a 1 mM solution in dimethylsulfoxide; fura-2 pentapotassium salt was stored as a 6 mM solution in potassium acetate, and $\omega$-CgTX was stored as a 100 $\mu$M solution in distilled water. All of the chemicals except for phenytoin were maintained at $-20°$ C. and protected from light.

The cells were incubated with 2 $\mu$M fura-2 AM in BSS (described in Example 1) at room temperature (21–23° C.) for 60 min. After being washed at least three times with BSS, the cells were used for measurement of $[Ca^{2+}]_i$ at room temperature. Cell fluorescence was measured as described in Example 2. Absolute calcium values were calculated as shown in Example 2.

Bombesin was added to the cells at a final concentration of 1 $\mu$M. Calcium mobilization levels were measured from –30 seconds to 150 seconds after bombesin treatment. (FIG. 5A) The particular experimental set up resulted in a maximum difference in $[Ca^{2+}]_i$ between AD cells and control cells at a time of 42 seconds after bombesin was added.

Forty two (42) seconds after bombesin treatment, in the absence of extracellular $Ca^{2+}$, the $[Ca^{2+}]_i$ levels in Alzheimer's disease cells are much larger (p<0.0001) than in age-matched and young controls. The numbers of cell lines (N) are 10, 8, and 6 for Alzheimer's disease, age-matched and young cells, respectively. The values are means±S.E.M. (FIG. 5B)

Bombesin stimulated IP$_3$-induced $Ca^{2+}$ release from intracellular storage sites in fibroblasts from all groups, but it caused a larger and more prolonged response in AD fibroblasts. This larger and prolonged response in AD cells was independent of extracellular $Ca^{2+}$. On the other hand, the IP$_3$-mediated $Ca^{2+}$ responses in AC and YC cells were followed by $Ca^{2+}$ entry. When this $Ca^{2+}$ entry was diminished by removal of extracellular $Ca^{2+}$, or blocking with inorganic $Ca^{2+}$ blockers, the bombesin-elicited $Ca^{2+}$ responses in control sells were found to return to the basal level faster than in AD cells (FIG. 5A). The results shown in FIG. 5A are for cells washed with BSS nominally free of $Ca^{2+}$.

Since $Ca^{2+}$ influx induced by bombesin was not observed in AD cells, this pathway of $Ca^{2+}$ entry following the decrease of stored calcium seems to be altered. This test independently confirmed the diagnoses made by the previously described test based on potassium channel dysfunction. In particular, the $Ca^{2+}$ responses at 42 sec after 1 $\mu$M bombesin stimulation in AD fibroblasts in the absence of extracellular $Ca^{2+}$ were always higher than 300 nM. In contrast, the $[Ca^{2+}]_i$ in AC and YC were less than 300 nM and 200 nM, respectively (FIG. 5B).

In a variation on the above experiment, $Ca^{2+}$ responses were induced by 1 $\mu$m bombesin in the presence of extracellular calcium. In the presence of 2.5 mM extracellular CaCl$_2$, 1 $\mu$m bombesin elicited a fast peak of $[Ca^{2+}]_i$, followed by a sustained phase for YC and AC cells, but not for AD cells. (FIG. 6A). This difference was evident 90 seconds after bombesin application and with a significance level of p<0.001. FIG. 6B). This difference in response of AD and non-AD cells to bombesin in the presence of extracellular calcium can be used to provide a "yes or no" diagnosis of AD. Detection methods similar to those described above wth respect to the second embodiment of the invention involving the diagnosis of AD by detecting differences between non-AD and AD cells in response to select potassium channel blockers (e.g., TEA) may be used. Furthermore, the combination of this diagnostic test with any one of the above diagnostic tests further increases the confidence level of a correct diagnosis as AD or non-AD.

EXAMPLE 4

Responses In Neuropathological Non-AD Fibroblasts

Using the techniques described in Examples 2 and 3, cells from donors with other diseases were measured for intracellular calcium levels in response to either TEA or bombesin.

Fibroblasts from a Parkinson's disease donor had normal TEA (indicated as +) and bombesin responses ("N"), and did not significantly differ from responses observed in the age-matched control group. Fibroblasts from two schizophrenic patients also had normal TEA and bombesin responses. In addition, normal TEA responses were observed in five out of seven cases of Huntington's disease, and the bombesin response was normal in all Huntington's cases. Furthermore, normal TEA and bombesin responses were observed in four out of four cases of Wernicke-Korsakoff disease (Table 6). These responses are significantly different from those of AD fibroblasts to the level of p<0.0001 (Fisher's exact test). "*" indicates autopsy confirmation.

TABLE 6

| Line # | Age | Gender | Race | Condition | TEA | Bombesin |
|---|---|---|---|---|---|---|
| AG08395 | 85 | F | W | Parkinson's* | + | N |
| GM01835 | 27 | F | W | Schizophrenia | + | N |
| GM02038 | 22 | M | W | Schizophrenia | + | N |
| GM06274 | 56 | F | W | Huntington's | + | N |
| GM02165 | 55 | M | W | Huntington's | + | N |
| GM00305 | 56 | F | W | Huntington's | − | N |
| GM01085 | 44 | M | W | Huntington's | + | N |
| GM01061 | 51 | M | W | Huntington's | + | N |
| GM05030 | 56 | M | W | Huntington's | − | N |
| GM04777 | 53 | M | W | Huntington's | + | N |
| 7504 | 50 | M | W | Wernicke-Kors. | + | N |
| 7505 | 52 | F | W | Wernicke-Kors. | + | N |
| 7507 | 63 | M | W | Wernicke-Kors. | + | N |
| 7508 | 64 | M | W | Wernicke-Kors. | + | N |

Every reference cited hereinbefore is hereby incorporated by reference in its entirety.

EXAMPLE 5

Characterization of Cp20 Protein

Materials & Methods

Animal tissue. Optic, lobes from fresh squid (*Loliog pealei*, Calamari, Inc.) were dissected and frozen on liquid nitrogen and stored at –80°. Hermissenda crassicornis were obtained live from Sea Life Supply, Sand City, Calif.

Purification of cp20. 150 squid optic lobes were added to 100 ml buffer 10 mM Tris-HCl pH 7.4 20 $\mu$g/ml leupeptin, 20 $\mu$g/ml pepstatin, 50 mM NaF, 1 mM EDTA and 1 mM EGTA). PMSF and dithiothreitol (DTT) were added to 0.1 mM and 200 mM, respectively, and the optic lobes were homogenized at 4° in a high-speed homogenizer followed by sonication. The homogenate was centrifuged (100,000 g×90 min) and the supernatant was filtered through an 0.22 $\mu$m filter and passed through an Amicon filter (30 kDa cutoff). The low MW fraction was then concentrated on a second filter (3 kDa cutoff) followed by concentration of 100 μl in Centricons (Amicon Corporation) pretreated with BSA. Use of untreated Centricons led to complete loss of protein.

The retained fractions were injected onto an AX-300 anion-exchange HPLC column (1×25 cm, Synchropak. The column was eluted at 2 ml/min and 10° C. with a gradient of 0–0.6M buffer (1M KAc, pH adjusted to 7.4 with HAc) for 20 min. followed by 0.6M buffer for 40 min. Each chromatogram was statistically analyzed by creating a correlation curve with the $t_R$ of each peak plotted against the $t_R$ of all the peaks in a reference chromatogram, a chromatogram of proteins from 5 eyes dissected from a group of Hermissenda conditioned in a previous experiment, as described previously (Nelson T., et al. (1990). *Science* 247, 1479–1483.). Briefly, Hermissenda conditioning consist of 75 pairings of a 3 sec light, which terminated with 2 sec rotation. These sessions of this training were concluded on successive days. The animals demonstrate associate learning when the conditional stimulus, light, elicits the response elicited before only by the unconditioned stimulus, rotation. A candidate cp20 peak was considered to match only if its $t_R$ fit within ±0.2% to the expected $t_R$ and if 10 or more other peaks could also be matched with the same precision. If the cp20 peak could not be unequivocally identified, or a unique correlation curve could not be constructed, the preparation was discarded. Fractions were collected in polypropylene tubes containing Triton X-100 at a final concentration of 0.2 mM.

A portion of each HPLC fraction surrounding the final cp20 peak was analyzed by SDS gel, blotted, stained with colloidal gold (CG) and enhanced with silver (IntenSE BL, Amersham). If densitometry of the blot indicated less than 85% purity, the preparation was re-purified or discarded.

Cation-exchange HPLC. In several experiments, the cp20 was further purified by cation-exchange HPLC (S-300, 4.6×250 nm, Synchropak). The column was eluted at 0.5 ml/min for 10 min with 0.2M LiCl pH 6.0, followed by a gradient of 0.02 to 0.7M LiCl over 60 min.

Each fraction was analyzed for GTPase and analyzed by SDS gel. Some samples were analyzed by CM300 HPCL (Synchropak) with a gradient of 0–1M KAc over 30 min.

Reversed-phase HPLC. The C18 column (Macrosphere 300, 5 g) was eluted at 0.35 ml/min with 20–100% ACN/ 0.1% TFA over 90 min followed by 100% ACN/0.1% TFA for 90 min.

GTPase was measured as described previously (Nelson T., et al. (1990). *Science* 447, 1479–1483.). Briefly, fractions were incubated for 120 min with $-^{32}P$-GTP in the presence of 100 mM Tris-HCl, pH 7.4 and 10 mM $MgCl_2$. The $^{32}P$—($P^{-32}$ inorganic phosphate) released was extracted into benzene after reaction with silicotungstic acid and the amount of radioactivity was measured in a scintillation counter. Peptides and proteins were quantitated using colloidal gold reagent (Aurodye, Amersham) (Hunter J., Hunter S. (1987). *Anal. Biochem.* 164, 430–433.) as modified in (Nelson T., et al. (1990). *Science* 247, 1479–1483.).

Photoaffinity labeling. Samples were incubated in closed 0.5-ml tube for 30' at 250 with $\alpha$-$^{32}P$-GTP, irradiated with UV light and analyzed by SDS gels as described previously (Nelson T. J., et al. (1991). *J. Neurochem.* 57, 2065–2069) followed by autoradiography.

Monoclonal antibodies. Cp20 from 20 squid optic lobes was injected into mouse spleen. A single injection of approximately 50 nanograms (ng) of protein bound to nitrocellulose was administered. The spleen lymphocytes were fused with mouse myeloma cells X63-Ag8-653 (American Type Tissue Culture Collection). Hybridoma cells were selected by ELISA using plates coated with optic lobe extract. Squid optic lobe extract was made by homogenation of squid optic lobes in water and centrifugation at 5–10,000 g for 10–20 min. Elisa plates were coated by filling each well with 0.1 ml of optic lobe extract and incubating at room temperature for >1 hour. The hybridoma was cloned by limiting dilution and cultivated in serum free media (Modified Eagle Medium).

The IgM fraction was purified by precipitation with $(NH_4)2SO_4$ and dialyzed against PBS.

Polyclonal Antibody A synthetic peptide corresponding to ARLWTEYFVIIDDDC (with 2 glutamates for solubility and cysteine for conjugation to KLH) was synthesized, conjugated with keyhole limpet hemo-cyanin (KLH) and suspended in Freunds adjuvant. Approximately 0.1 mg peptide was injected intraperitoneally into one rabbit biweekly, over 4 months. Test bleeds were obtained every two weeks and tested for efficacy at recognizing squid Cp20 in Western blots of crude optic lobe homogenate.

Western Blot Analysis Up to 40 ug (micrograms) protein per lane was applied to 4–20% gradient Tris-glycine polyacrylamide gels (Novex Corp., San Diego, Calif.) and blotted onto reinforced nitrocellulose. After blocking at 4 for 12 hr with BSA, the blots were incubated with polyclonal antiserum at a dilution of 1:600 or with monoclonal antibody (ammonium sulfate fraction) at a dilution of 1:2000 for 2 hr at room temp. Cp20 was visualized using alkaline phosphatase-conjugated rabbit anti mouse (Sigma) or goat anti rabbit second antibodies (Sigma) (1:2000) and developed with NBT (nitro blue tetrazolium chloride)-BCIP. Because a single Hermissenda CNS contains only 8 μg of total protein and subnanogram quantities of cp20, it was necessary to use a different source (squid optic lobe) in order to obtain adequate quantities of cp20 for characterization.

Figure 7D:
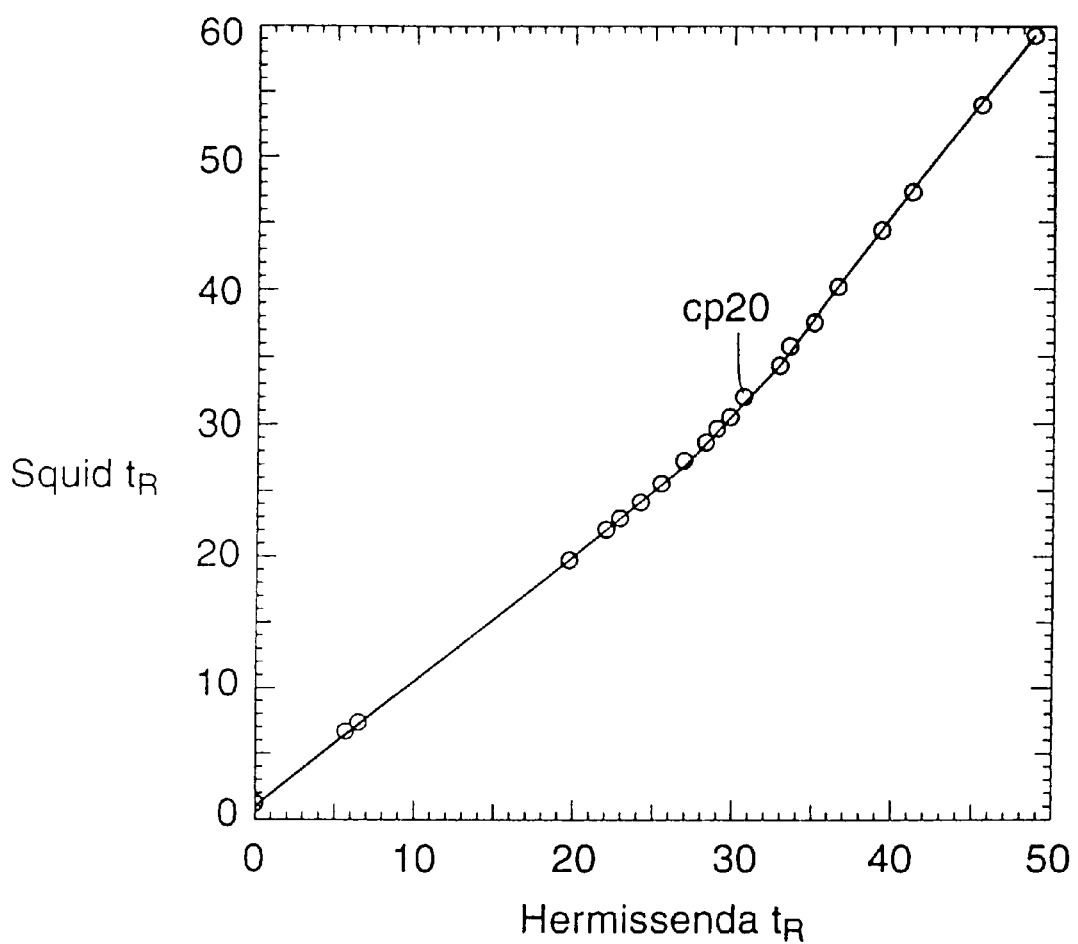

Computer-assisted pattern matching cf the HPLC profiles demonstrated that the HPLC profiles of cytosolic proteins from squid optic lobe and Hermissenda eye were quite similar (FIGS. 7B, 7C, 7D), with the exception of the cp27 peak (29.5 min), which was much smaller in squid than Hermissenda, and 2–3 other peaks which were larger in squid.

To determine whether the AX-300 HPLC column adequately separates G proteins, squid homogenate was chromatographed on AX-300 and the molecular weights of all GTPases were determined. 84% of the GTPase activity from squid eluted in large unresolved peaks at 12–18 and 19–21 min. Ras, rap and Sarlp, measured by Western blotting of HPLC fractions, eluted at 22.8, 20.5, and 19.4 min, respectively (not shown). Thus, the HPLC column was highly efficient at separating cp20 ($t_R$ 30 min) from other GTP-binding proteins. Interestingly no G proteins were detected in the large non-retained peak (6–10 min) (see FIG. 7A).

Figure 8A:
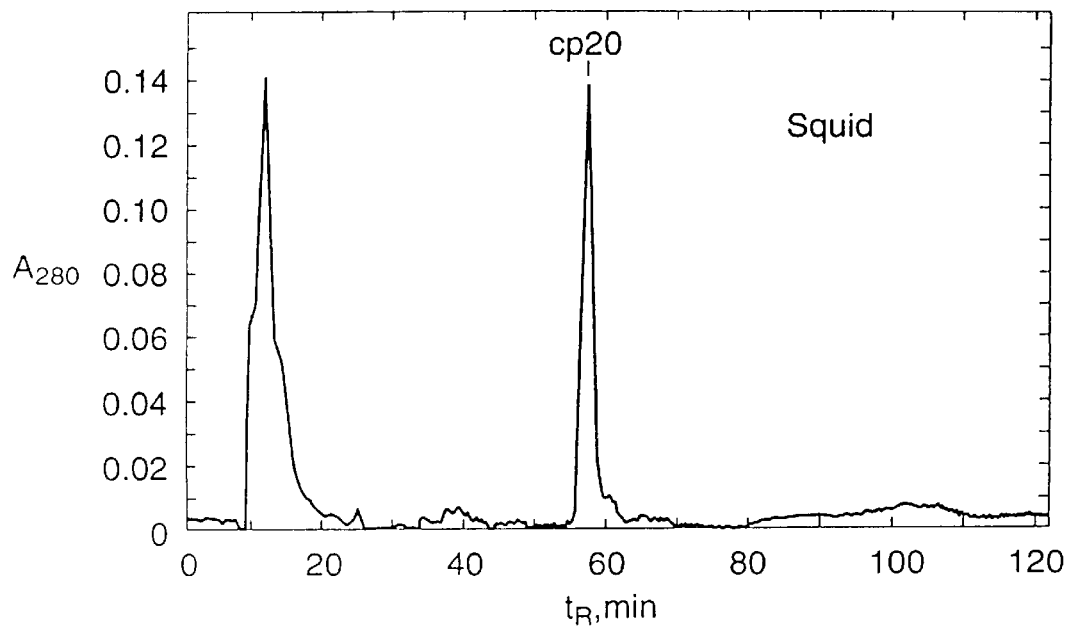
FIG. 8. RP-HPLC $A_{280}$ profile of purified squid cp20 (Upper). The peak at 15' is the non-retained fraction, containing DTT and buffer components. Lower:RP-HPLC rechromatography of a cp20 peak from one Hermissenda CNS from an earlier experiment (Nelson T., et al. (1990). Science 247, 1479–1483.). Peaks at 4, 12, 15, 42, 46, and 78 min are buffer components. Flow rate: 0.5 ml/min.
Figure 8B:
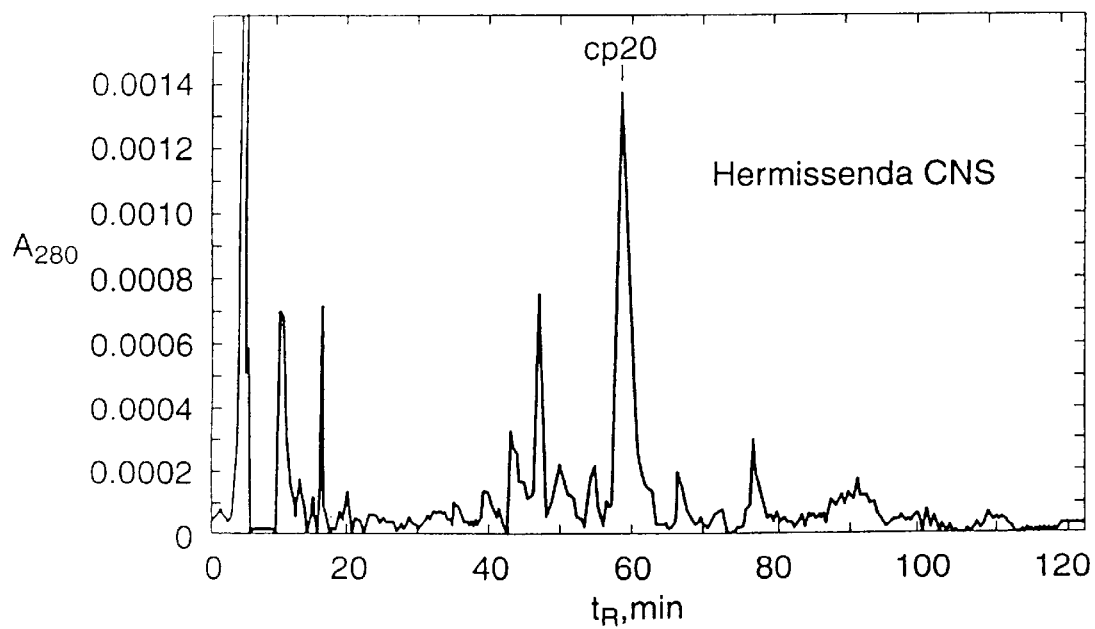

To test the purity of the cp20, squid cp20 was reanalyzed by RP-HPLC. After thee large non-retained peak caused by DTT and salts, a single peak was observed (FIG. 8). Its GTPase activity was difficult to measure, presumably due to the harsh conditions (100% ACN/0.1% TFA). No activity was seen at other positions. The tR is comparable to that seen previously with cp20 from Hermissenda eye and CNS (Nelson T., et al. (1990). Science 247, 1479–1483.).

Figure 9A:
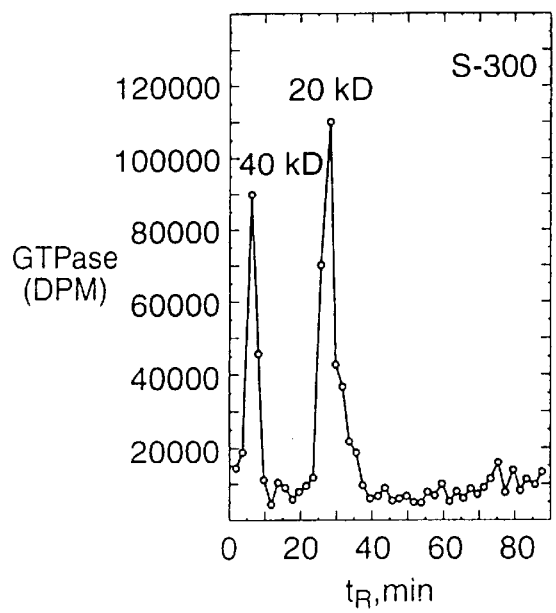
FIGS. 9A–9D. S-300 (9A) and CM-300(9B) cation exchange HPLC GTPase profile of purified squid cp20. Half of each fraction was analyzed for GTPase activity and half was analyzed on SDS gels. After 18 min in (9B), the GTPase baseline increased dramatically due to interference in the assay by the HPLC solvent. (9C) GPC-100 size-exclusion HPLC GTPase profile of squid cp20 purified in the absence of DTT (dithiothreitol). By this stage, most of the cp20 has dimerized. (9D) Specificity of anti cp20.
Figure 9B:
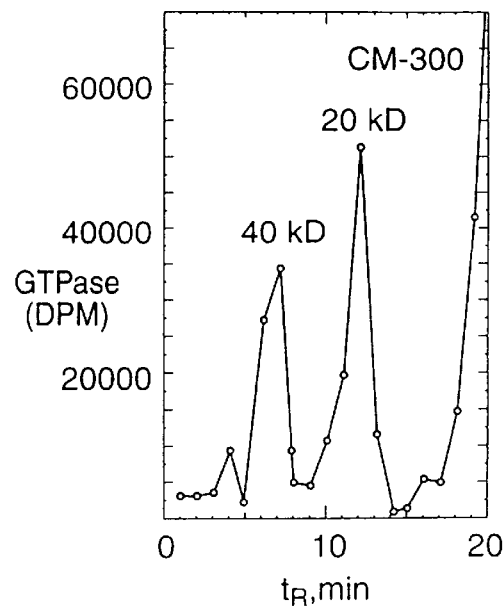
Figure 9C:
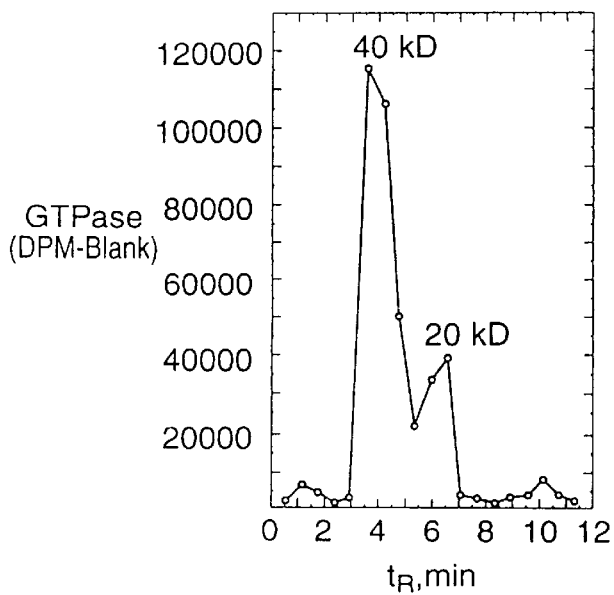

Cp20 form both squid optic lobes and Hermissenda CNS was also rechromatographed by S-300 and CM-300 cation exchange HPLC (FIGS. 9A, 9B). Each fraction was tested for GTPase activity and analyzed on SDS gels. In both cases, two peaks of GTPase activity were detected, with Mr's of 20 and 40 kDa, suggesting a homodimeric structure. In a similar experiment, cp20 purified in the absence of DTT was fractionated on a non-denaturing gel. When the 40 kDa section of the gel was eluted, reacted with DTT, and analyzed by SDS-PAGE, a 20 kDa band was observed. In contrast, in the absence of DTT, only a 40 kDa protein band was observed (FIGS. 10A, 10B). Thus, the 40 kDa protein is not an impurity, but dimerized cp20.

Further evidence of dimerization was obtained by photoaffinity-labeling the 20- and 40-kDa peaks with $^{32}$P-GTP and analyzing by SDS-PAGE. 32p-labeled bands with Mr's of 40 and 20 kD were found in the lanes corresponding to both the 40 and 20 kD HPLC peaks (not shown). Thus, the 40 kD band was not an artifact of photolabeling but is caused by natural dimerization. However, it is not yet known whether dimerization occurs under physiological conditions.

A monoclonal antibody prepared against purified squid cp20 also recognized 20 kD and 40 kD bands in squid supernatant, and a 20 kD band in Hermissenda (FIGS. 10D, 10E). The proportion of staining at 40 kD increased if the samples were allowed to stand at 4° before analysis. Despite the fact that the antibody was raised against squid protein, it reacted more strongly with Hermissenda cp20. Cp20 was also detected in rabbit hippocampus particulate fraction, but not in the supernatant (FIGS. 10F, 10G).

Figure 9D:
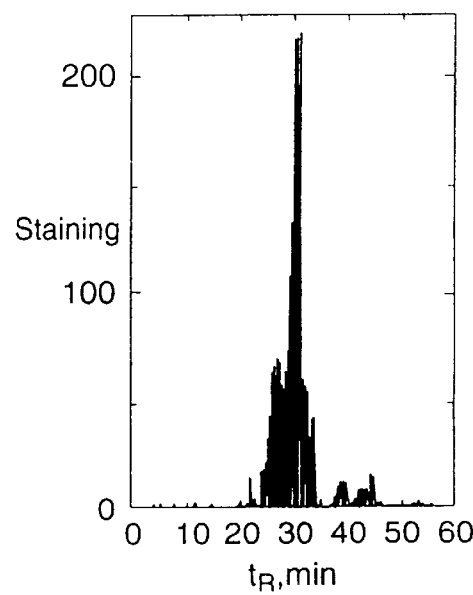

Western blots of HPLC fractions from Hermissenda supernatant revealed a larger peak at 31 min coinciding with cp20, and a smaller peak at 28 min, possibly the dephosphorylated form of cp20 (FIG. 9D).

Squid cp20 did not cross-react with pan-ras, anti-ARF or anti-rap monoclonals (not shown). Cp20 weakly cross-reacted with anti-Giα, an antibody against the GTPase active site (Goldsmith P. et al. (1988). *J. Biol. Chem.* 263, 6476–6479.) (FIG. 1H). This antibody did not cross react with a sample of cloned ras, suggesting that cp20 is more closely related to the trimeric G proteins than to ras.

A polyclonal antibody against the peptide ARLWTEY-FVIIDDDC which is derived from the largest tryptic peptide of Cp20 (tR 40 min in FIGS. 12A and 12B) cross-reacted with Cp20 and Sarlp, and weakly cross-reacted with cloned ARF (FIGS. 10I–10L), but not with ras, also consistent with the conclusion that cp20 is more closely related to ARF-family proteins than to ras.

Using the ability of DTT to convert cp20 into monomers, it was possible to purify cp20 to apparent homogeneity with two ultrafiltration steps followed by a single HPLC column step (FIGS. 10C, 11A). The stoichiometry of $^{32}$P-GTP binding to purified squid cp20 in several preparations ranged from 0.90–0.95, indicating that the protein was 90–95% pure. The protein when pure adsorbed to concentrators and polyproplyene test tubes unless Triton X-100 was added. The pI of squid cp20 was 5.2 by electrophoresis, and 5.86 by chromatofocusing. Hermissenda cp20 was identical to squid in both Mr and pI (FIG. 11B).

Sequencing of 5 tryptic peptides from squid cp20 revealed an overall 50% identity (23/46 amino acids) with Sarlp, a 21 kDa GTP-binding protein in the ARF family (Nakano A. Muramatsu J., (1989). *J. Cell Biol.* 109, 2677–2691.) (FIG. 12A). Several of the non-matching residues in Cp20 and Sarlp are conservative substitutions (e.g., D→E, N→D, A→L). Sarlp is involved in the transport of proteins from ER to the Golgi apparatus (Nakano A. Muramatsu J., (1989). *J. Cell Biol.* 109, 2677–2691; Barlow C., et al. R. (1993). *J. Biol. Chem.* 268, 873–879; Oka T., et al. (1991) *J. Cell Biol.* 114, 671–679.). This sequence is also similar to a lesser degree to ARF and the Giα trimeric G protein but shows little similarity to ras.

Injection of cp20 into Hermissenda photoreceptors causes a marked reduction of the K$^+$ currents $I_A$ and $I_{K+Ca2+}$, both of which are known to be reduced after associative learning (Alkon D. L., et al. (1982) *Science* 221, 1201–1203.). Injection of cp 20 also reproduces the structural changes in neuronal architecture previously observed after associative learning (Collin C., et al., *Biochem. Biophys. Res. Commun.,* in press.).

Several other GTP-binding proteins, including ras (Santos E., et al. (1988) *J. Biol. Chem.* 263, 9853–9858.), are known to form homodimers. In Hermissenda, rap also exists predominantly as a 46 kDa dimer (McPhie, D., personal communication). Because of the homology with Sarlp and ARF, cp20 probably is a member of the ARF family of low-MK GTP-binding proteins. In yeast, these proteins, including Sarlp, ARF, and YPT1, are involved in several steps of vesicle transport (Nakano A. Muramatsu J., (1989). *J. Cell Biol.* 109, 2677–2691. Alkon D. L., et al. (1990). *Proc. Natl. Aced. Sci.* (USA) 87, 1611–1614. Walker M., et al. (1992) *J. Biol. Chem.* 267, 3230–3235. Segev N., et al. (1988) *Cell* 52, 915–924.). A group of low-MW GTP-binding proteins has also been found to be associated with rapid axonal transport (Bielinski D. F., et al. (1989) *J. Biol. Chem.* .64, 18363–18367.). Thus, the similarity between cp20 and ARF-related proteins is consistent with the observed effects of cp20 on regulation of intraaxonal particle movement (Moshiach S., et al. (1993). *Brain Res.* 605, 298–304.). Association with vesicle membranes is also consistent with cp20's strong retention on C18 HPLC, which suggests that it has a lipophilic character. It has not yet been established which of the observed physiological effects of cp20 are directly attributable to cp20 and which are mediated by some other molecule, such as protein kinase C. Ras is also able to produce some of the effects of microinjected cp20, but is only effective at much higher concentrations (Collin C., et al. (1990) *Science* 250, 1743–1745.). Like cp20, ARF is more closely related to the α-subunit of trimeric G proteins than to ras (Sewell J., Kahn R. (1988) *Proc. Nat. Acad. Sci.* (USA) 85, 4620–4624.). The present data show cp20 is not ras but a new protein related to Sarlp and ARF.

The unambiguous classification of cp20 within a category of proteins involved in signalling and regulation of molecules between the ER and Golgi, together with its previously-established impact on neuronal function and structure and its causal implication in memory storage, provide the first evidence suggesting the possibility that memory storage could depend in part on regulation of particle trafficking among intraneuronal organelles.

EXAMPLE 6

Alterations In Cp20 Protein Levels In Alzheimer's Patients

Materials and Methods

Cell lines and procedures for cell culture. Human skin fibroblasts were grown to confluence in 75 cc growing surface culture flasks (Falcon) containing Dulbecco's modified Eagle's medium (DMEM, Gibco), supplemented with 10% fetal calf serum (Gibco). Cells from thirteen AD individuals [AG06843, AG06844*, AG06848*, AG08170, AG7637, AG08527* familiar alzheimer's disease (FAD) # 964, 4 males, 2 females); AG04401 (FAD, # 747, female); AG07376, AG07377, AG06262, AG05770*, AG06263, AG07375 (Non-FAD, 5 males, 1 female), 60.4±6.05 years (Mean±SD), "*"=autopsy confirmation], nine AC [GM04260, GM04560, GM03524, AG07303, AG08044, AG09878, AG07141, AG07310, AG06241 (all apparently normal, without known family history individuals, 3 males, 6 females), 62.89±5.16 years], and four "escapees" [AG06838†, AG06842†, AG07665‡ (members of family # 964); AG08265† (member of family # 2090), 67.25±6.85 years, "†"=immediate relative affected (parents and/or siblings), "‡"=uncle affected] were used for Cp20 and total protein assessments. These cells lines are available through National Institute of Aging, 1991 Catalog of Cell Lines (1991); National Institute of General Medical Sciences, 1990/1991 Catalog of Cell Lines (NIH Publication 91–201, 1990). The same AC cell lines were also grown in duplicate. One set of cells was treated with 10 nM β-amyloid (in DMSO) and the other with DMSO alone for 48 h. The total DMSO was less than 0.1% in both groups. β-amyloid 1–40 peptide (Bachem) was prepared in DMSO (230 μM) and later diluted in distilled water (Picopure®, Hydro) to reach the final incubation concentration of 10 nM. —his low β-amyloid concentration has been shown to have specific AD-like effects on a 113 pS K+ channel, without altering basal levels of intracellular $Ca^{2+}$ or causing other nonspecific cell damage (R. Etcheberrigaray, E. to, C. S. Kim, D. L. Alkon, *Science* 264, 276 (1994)).

Procedures for cell homogenization and protein extraction. Culture medium seas removed by aspiration and replaced with ≈20 ml of cold (4° C.) PBS. The cells were scraped from the flasks and centrifuged at 10,000 g for 10 min. at (4° C.). Supernatant was discarded, the pellet washed with 1 ml PBS and then inverted to remove any remaining PBS for about 2–3 min. Pellets were washed with 1 ml of "homlogenization buffer" (50 mM NaF, 1 mM EDTA, 1 mM EGTA, 20 μg/ml leupeptin, 50 μg/ml pepstatin, 10 mM TRIS-HCl, pH=7.4), transferred to Eppendorf tubes and centrifuged (4° C.) for 10 min at 10,000 g. Supernatant was discarded, tubes inverted for 2–3 min., and then 50 to 75 μl of homogenization buffer were added. The pellet was finally sonicated for 10–20 sec (ultrasonic homogenizer, Cole-Parmer Instruments). The crude protein extract was stored at –80° C. for later analysis.

Protein assay, immunoblotting, and total protein analyses procedures. Protein concentration was determined following an established dye-binding protein assay (R. D. Lane et al. *J. Immunol Methods* 92:261 (1986) for all homogenates. For immunoblots, a SDS-PAGE 4–20 t gradient, 1.5 mM thick gel was used (Novex, San Diego, Calif.). Sample volume was adjusted to give a protein concentration of 1 μg/μl. Novex sample buffer (16 μl) was added to 16 μl of sample, the solution was heated to 85° C. for 2 min, loaded into the gel and subjected to 115 mV for ≈1.5 h. The Rainbow™ molecular weight standard (Amersham) was also loaded. The resolved proteins were electrophoretically transferred (51.2 mA for 2 h) to a unmodified 8 by 8 cm nitrocellulose paper (Pierce). Transfer buffers were as follows: anode, 40 mM E-aminohexanoic acid, 25 mM TRIS, 20% methanol, pH=9.4; cathode, 25 mM TRIS, 20% methanol, pH=10.4, and 300 mM TRIS, 20% methanol, pH=10.4. The nitrocellulose paper was exposed overnight to SuperBlock™ (Pierce) and then incubated at room temperature for 1.5 h with a 10 ml solution containing the Cp20 monoclonal (as described in Materials and Methods, see Example 5) antibody (1:1000 dilution) and SuperBlock™. After rinsing 5 times with SuperBlock™, the nitrocellulose paper was incubated (lh, room temperature) with 40 ml of protein A alkaline phosphatase conjugated (1:500 dilution, Cappel Organon Teknika) in SuperBlock™. After washes with SuperBlock™ (2 times), PBS (2 times), and 2 times with APS (100 mM TRIS, 100 mM NaCl, 5 mM $MgCl_2$, pH=9.4), the nitrocellulose paper was stained for about 7 to 10 min with a staining solution containing: 40 ml of APS, 3 mg NitroBlue™ Tetrazolium (Pierce), and 5 mg of 5-bromo-4-chloro-3-idolyl phosphate toluidine salt (Pierce). The staining reaction was stopped by rinsing with distilled water. Immunoblots were then digitized on a flat bed scanner and analyzed with imaging software written in the laboratory (TNImage by T. J. Nelson) for quantitative analysis. To correct for any difference in overall staining between gels, the integrated values of the band(s) of interest were normalized to the average background intensity of the blots. To study overall protein composition, an aliquot of each sample was analyzed by SDS-gel electrophoresis and the gel was exposed to the staining solution (0.1% Coomassie Blue R-250, 40% methyl alcohol, 10% acetic acid) for 20 min, and slowly destined (7.5% acetic acid, 15% methyl alcohol) for about 24 h. MW was determined by comparison with Mark12™ standards (Novex). Quantitative analysis of the gel was conducted with similar methods to those used for analyzing the immunoblots. Measurements of the regions of interest were normalized to the total densitometric area per lane.).

Monoclonal antibodies. Cp20 was purified from 20 squid optic lobes as described in the Methods and Materials in Example 5. Briefly, the purified protein was injected into mouse spleen and the spleen lymphocytes were fused with mouse myeloma cells X63-AG8-653 as described in Example 5. Hybridoma cells were selected by ELISA using plates coated with optic lobe extract as described in Example 5. The hybridoma was cloned by limiting dilution and cultivated in serum free media. The IgM fraction was purified by precipitation with $(NH_4)_2SO_4$ and dialyzed against PBS.

Figure 13B:
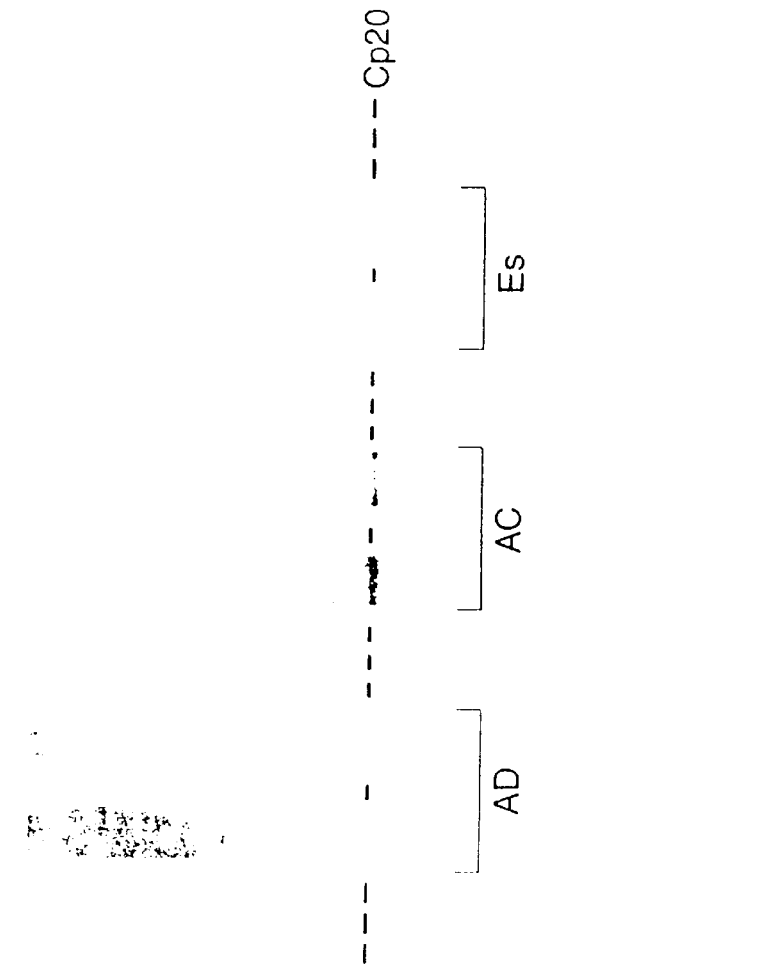
Figure 13A:
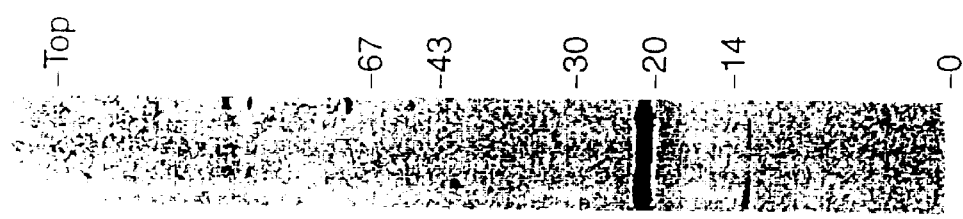
Figure 13C:
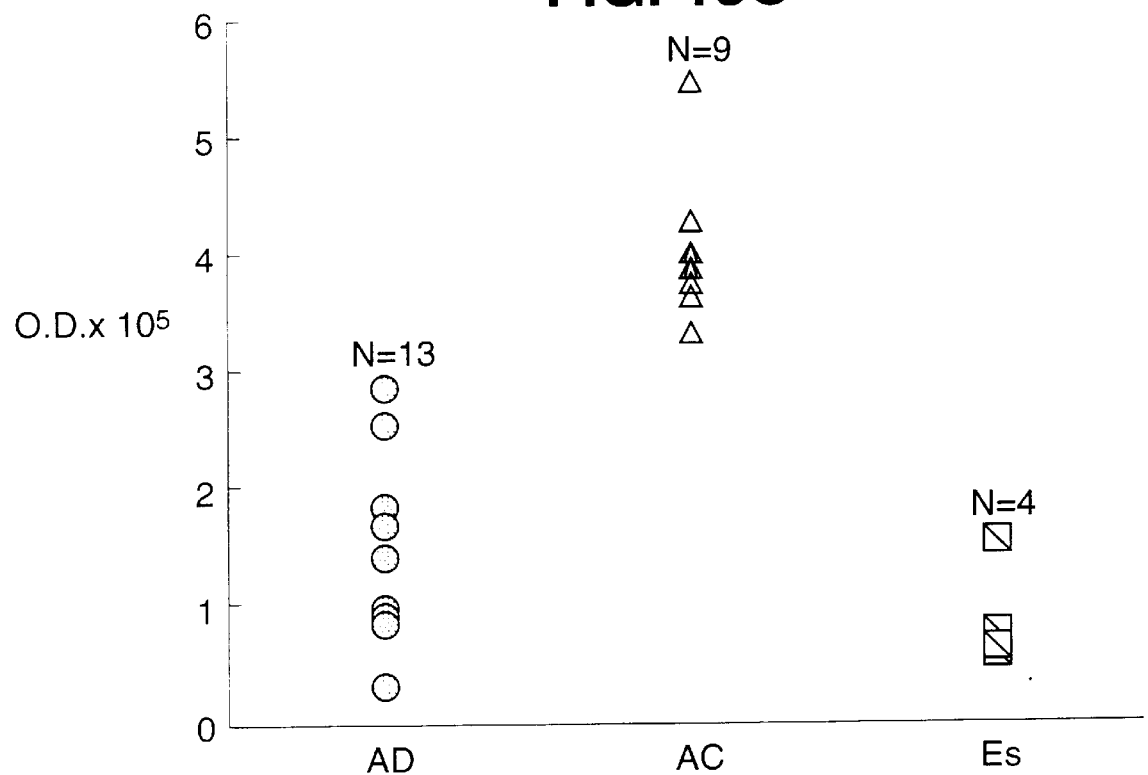
Figure 13D:
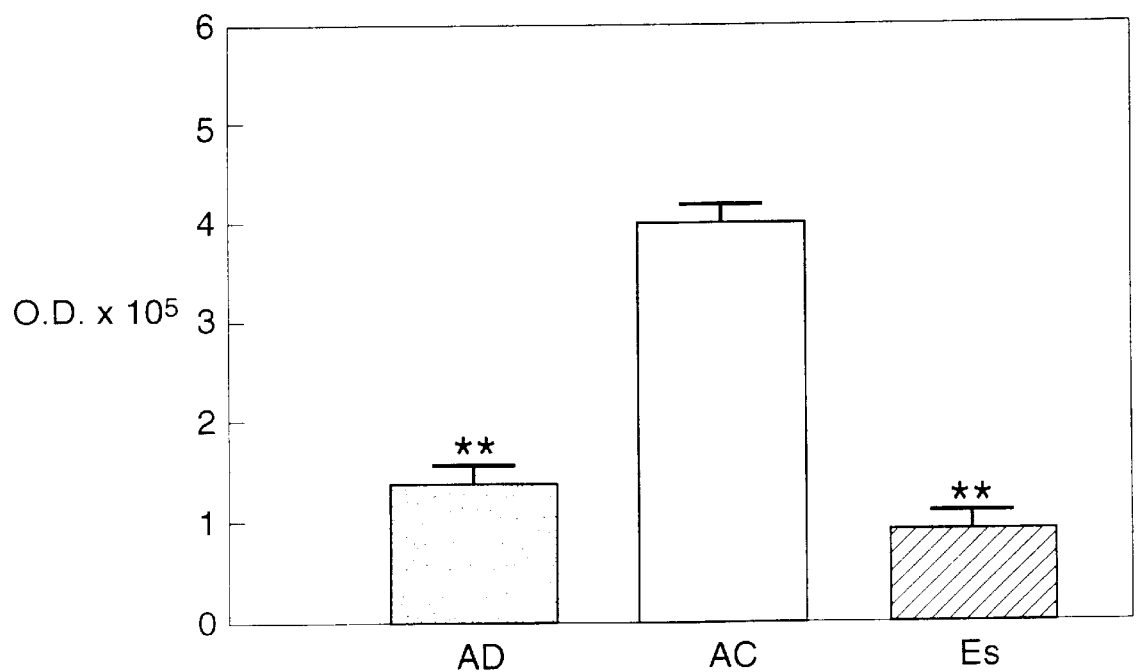

The antibody was previously shown to specifically recognize Cp20 in several species, including Hermissenda, rabbit, rat, sea urchin, and squid, as well as HPLC purified Squid Cp20 (see Example 5, and FIG. 13A) Fibroblasts from AD patients and age-matched (AC) controls were obtained from the Coriell Cell Repositories (Camden, NJ) and cultured as described in the Methods and Materials. Cp20 was assessed by using the Cp20 monoclonal antibody.(See Methods and Materials Examples 5 and 6) and standard immunoblotting (Western) techniques. A distinct dark band was observed in the 20 kD region of immunoblots of all 9 AC cell lines, while it was almost absent or greatly reduced in all 13 familial and non-familial AD cell lines (FIGS. 13B and 13C). The 20 kD band was also reduced or absent in immunoblots from four clinically normal ("escapees", Es) individuals, who were close relatives of patients with familial Alzheimer's disease (T. D. Bird, Alzheimer Disease (Raven, New York, 1994; R. D. Terry, R. Katzman, K. L. Bick eds.) pp). 65–74.). Quantitative analysis of the immunoblots (FIGS. 13C–13D) confirmed that Cp20 levels were significantly higher in the controls as compared to AD and Es cell lines, p<0.001 (ANOVA, Bonferroni post test). No significant differences were found between AD and escapee's cell lines. In order to rule out a generalized effect on all proteins of ≈20 kD, a total protein analysis was conducted on SDS-PAGE Coomassie blue stained gels. Visual inspection (FIG. 14A) of the 20 kD molecular weight (MW) region, confirmed by quantitative analysis (FIG. 14B), showed no between-group differences, p>0.05, n.s. (ANOVA, Bonferroni post-test; instal version 1.15, Graphpad software, San Diego, Calif.). Analysis of the 66 to 33 kD MW region also revealed no between-groups differences, p>0.05, n.s. (ANOVA, Bonferroni post-test). Two additional protein bands in the high MW region (a 200 kD) also showed no significant differences between experimental groups, p>0.05, n.s. (ANOVA, Bonferroni post-test).

Figure 15C:
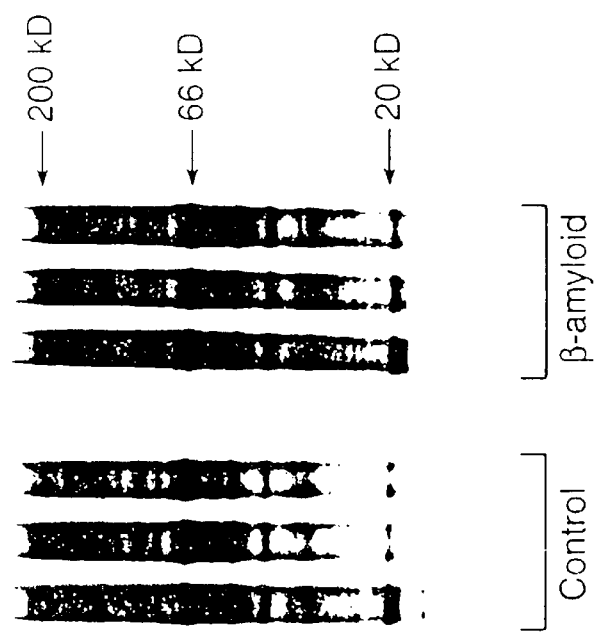
Figure 15A:
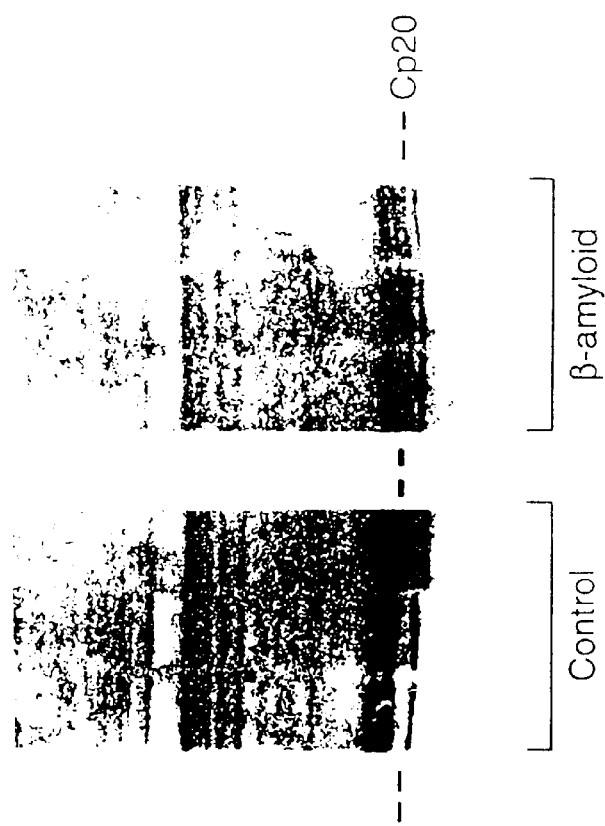
Figure 15B:
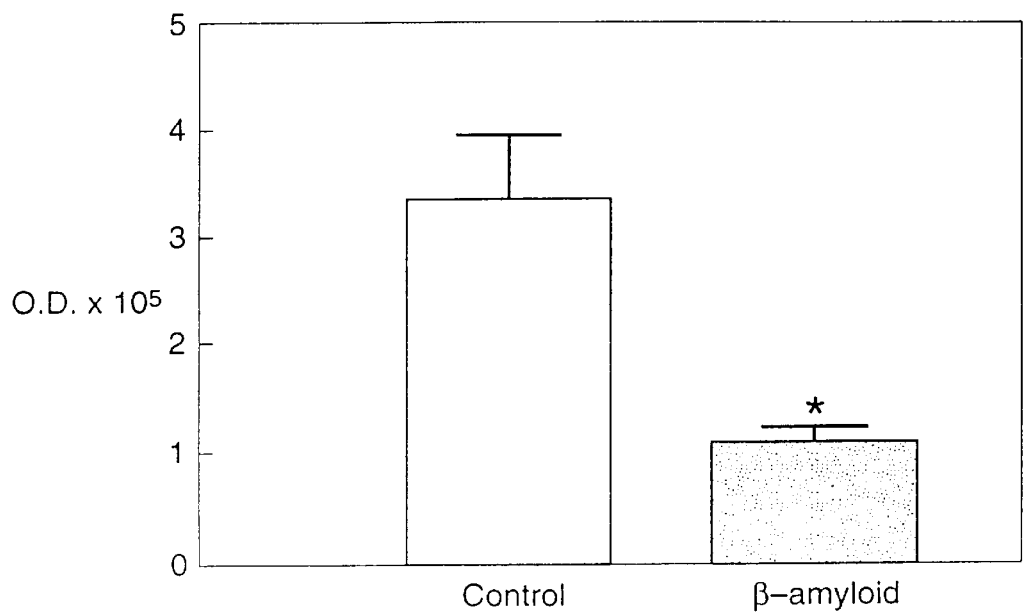
Figure 15D:
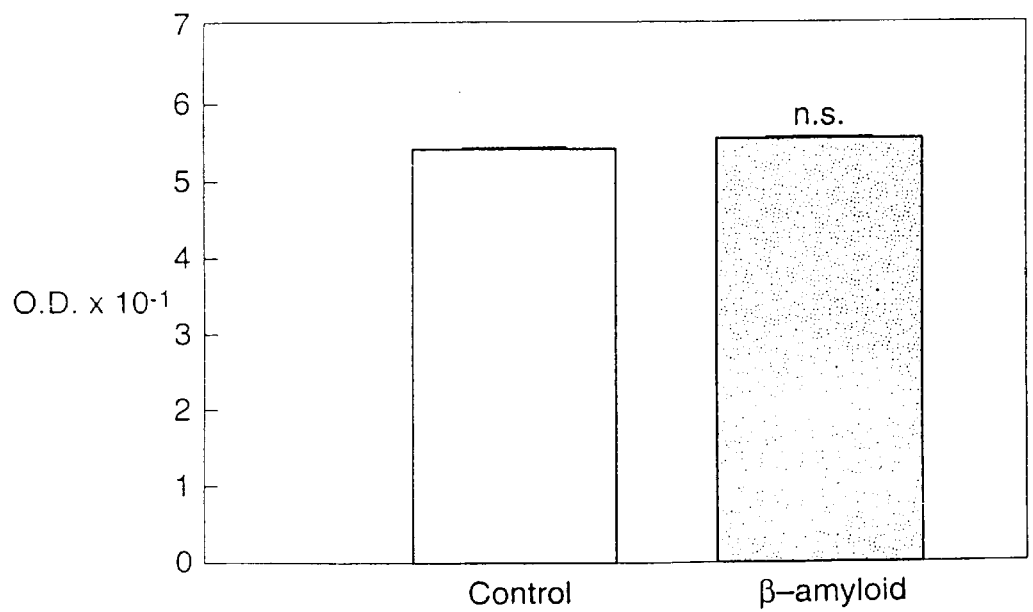

Since previous observations indicated that treatment with low concentrations of β-amyloid induces an AD-like K$^+$ dysfunction in control cells (R. Etcheberrigaray, E. Ito, C. S. Kim, D. L. Alkon, *Science* 264, 276 (1994).), we treated 9 AC call lines with 10 nM β-amyloid for 48 h. Following the same immunoblotting procedure and analysis we found that Cp20 was significantly reduced in β-amyloid treated cells as compared to their non-treated counterparts, p<0.003 (Wilcoxon) (FIGS. 15A–15B). Total protein analysis revealed that the β-amyloid treatment was not a generalized effect on all proteins in the 20 kD region (15C–15D), p>0.1 (Wilcoxon). In addition, no between-group differences were observed in the 66–33 and 200 kD regions.

These results clearly demonstrate that Cp20, a memory-associated protein that induces a number of molecular and cellular changes that have been observed during memory acquisition and storable (T. J. Nelson, C. Collin, D. L. Alkon, *Science* 247, 1479 (1990); T. J. Nelson and D. L. Alkon, *Proc. Natl. Acad. Sci.* USA 85, 7800 (1988); ibid 87, 269 (1990); D. L. Alkon et al. *Proc. Natl. Acad. Sci. USA* 87, 1611 (1990); S. Moshiach, T. J. Nelson; J. V. Sanchez-Andres, M. Sakakibara, D. L. Alkon, *Brain Research* 605, 298 (1993); Example 5), is markedly reduced in fibroblasts from Alzheimer's patients. This is a new, specific extension of our previous findings (see Examples 1–4; R. Etcheberrigaray et al., *Proc. Natl. Acad. Sci.* (USA) 90, 8209 (1993); E. Ito et al, *Proc. Natl. Acad. Sci.* (USA) 91, 534 (1994) that have shown that other cellular steps (K$^+$ channel regulation, Ca$^{2+}$ release) in memory storage are altered in Alzheimer's disease. Since Cp20 is an extremely potent regulator of K$^+$ channels (T. J. Nelson, C. Collin, D. L. Alkon, *Science* 247, 1479 (1990).), its absence or reduction in AD could have some relationship to the previously observed differences of K$^+$ channels for AD fibroblasts (R. Etcheberrigaray et al., *Proc. Natl. Acad. Sci.* (USA) 90, 8209 (1993); R. Etcheberrigaray, E. Ito, C. S. Kim, D. L. Alkon, *Science* 264, 276 (1994).) and olfactory neuroblasts (data not shown)). The previously demonstrated regulation by Cp20 of retrograde axonal transport, as well as its sequential homology with the ARF protein Sar1p (involved in vesicle trafficking; see Example 5) suggest that its absence could also influence the predisposition to and/or development of the proteinaceous plaques and neurofibrillary tangles that characterize Alzheimer's Disease pathology in the human brain. These pathological processes, like Cp20, directly or indirectly involve vesicle trafficking (S. Estus et al. *Science* 255, 726 (1992); T. E. Golde, S. Estus, L. H. Younkin, D. L. Selkoe, S. G. Younkin, ibid., 728 (1992); C. Haass, E. H. Koo, A. Mellon, A. Y. Hung, D. J. Selkoe, *Nature* 357, 500 (1992); J. Busciglio, D. H. Gabuzda, P. Matsudaira, B. A. Yankner *Proc. Natl. Acad. Sci.* (USA) 90, 2092 (1993); N. K. Robakis, *Alzheimer Disease* (Raven, N.Y., 1994; R. D. Terry, R. Katzman, K. L. Bick eds.) pp. 317–326.) and, possibly, alterations of microtubule-associated proteins (K. A. Crutcher, B. H. Anderton, S. W. Barger, T. G. Ohm, A. D. Snow., *Hippocampus* 3, 271 (1993). K. S. Kosik and S. M. Greenberg, *Alzheimer Disease* (Raven, N.Y., 1994; R. D. Terry, R. Katzrmua, K. L. Bick eds.) pp. 335–344). Phosphorylation of tau (a potentially pathological event) by mitogen-activated protein (MAP) kinase, can be promoted by APP (amyloid precursor protein, the protein from which β-amyloid originates) and prevented by inhibition of ras proteins (K. S. Kcosik and S. M. Greenberg, *Alzheimer Disease* [Raven, N.Y., 1994; R. D. Terry, R. Katzman, K. L. Bick eds.] pp. 335–344; S. M. Greenberg, E. H. Koo, W. Q. Qiu, A. W. Sandrock, K. S. Kosik, *Soc. Neurosci. Abs.,* 19, 1276(1994); K. S. Kosik, *JAMA* 271, 89 (1994) [in Medical News & Perspectives by P. Cotton]). The ras involvement in this process is intriguing, since ras and Cp20 share functional properties (C. Collin, A. G. Papagorge, D. L. Lowy, D. L Alkon, *Science* 250, 1743(1990)] and also some degree of homology (see Example 5). Moreover, one of the suggested normal functions for tau is to participate in microtubule elongation and shaping axonal morphology (K. S. Kosik, *Brain Pathology* 3, 39 (1993)), which may be related to dendritic changes induced by Cp20 during memory acquisition (S. Moshiach, T. J. Nelson, J. V. Sanchez-Andres, M. Sakakibara, D. L. Alkon, *Brain Research* 605, 298 (1993).). It is also interesting that G$_o$, a heterotrimeric GTP-binding protein involved in membrane trafficking and axonal transport (M. Bomsel, K. Mostov, *Molec. Biol. Cell* 3, 1317 (1092)), associates with the cytoplasmic domain of APP (Nishimoto, I. et al, *Nature* 362 (1993).). Thus, Cp20 alterations, perhaps linked to β-amyloid metabolism and tau phosphorylation, could affect normal axonal transport and intracellular vesicle trafficking, contributing to Alzheimer's Disease pathology. Since Cp20 was also reduced in Es (i.e. close relatives of individuals with familial Alzheimer's Disease), the observed loss of Cp20 could diagnostically mark Alzheimer's Disease as well as genetic predisposition to Alzheimer's Disease even in the absence of clear clinical symptoms of Alzheimer's disease.

EXAMPLE 7

Diagnostic Index For Alzheimer's Disease

Materials and Methods

Cell Culture Procedures Cultured fibroblasts were obtained from the Coriell Cell Repositories (Camden, N.J.) and from the Laboratory of Molecular and Cellular Neurobiology, Sacred Heart Hospital of Brescia (Brescia, Italy). Cell lines include AD, age-matched controls, controls suffering from other non-AD neurological and psychiatric conditions, and three cell lines from clinically unaffected members (Es, escapees) of the Canadian AD family 964 (Nee, L. E.; *Arch. Neurol.* 40:203–208; 1983). The Italian cell lines (designated by I in Table 7) are from living patients, the fibroblast preparation as well as diagnostic procedures are previously described (Govoni, S. et al; *Neurology* 43:2581–2586 (1993)). Additional information about the Coriell cell lines can be obtained elsewhere (National Institute of Aging, 1991 Catalog of Cell Lines. 1991; National Institute of General Medical Sciences, 1990/1991 Catalog of Cell Lines (NIH Publication 91–2011, 1990)). Cells were seeded as previously described) (Examples 1–4; Etcheberrigaray, R.; et al., *Proc. Natl. Acad. Sci. USA* 90:8209–8213; 1993) in 35 mm Nunc petri dishes, and used three to four days after seeding, at comparable levels of confluence (≈60 to 80 cells per mm$^2$).

Calcium Imaging. Culture medium was removed and cells were washed at least three times with BSS (in mM: NaCl 140, KCl 5, CaCl$_2$ 2.5, MgCl$_2$ 1.5, HEPES 10, Glucose 5, pH=7.4). The fluorescent probe was loaded by incubating the cells in 2 μM (in BSS) fura 2-AM (Molecular Probes) for 60 min at room temperature. After loading, cells were washed thoroughly with BSS or BSS-0 Ca$^{2+}$ (in mM: NaCl 140, KCl 5, CaCl$_2$ 0.1, MgCl$_2$ 1.5, EGTA 1, HEPES 10, Glucose 5, pH=7.4). After washes, 1 ml of fresh solution was added for intracellular $Ca^{2+}$ baseline measurements. TEA (Sigma) challenge was performed by adding to the dish 3 ml of TEA-modified BSS (TEA-MBSS) solution (in mM: TEA 133.3, NaCl 6.7, KCl 5, $CaCl_2$ 2.5, $MgCl_2$ 1.5, HEPES 10, Glucose 5, pH=7.4). This solution was adjusted in order to introduce no osmolality changes. Bombesin stimulation was accomplished by adding 1 ml of BSS plus bombesin to achieve final bombesin (Calbiochem) concentrations of 1 $\mu M$ and 100 nM, with and without external $Ca^{2+}$. Bradykinin (Calbiochem) in BSS and BSS-0 $Ca^{2+}$ (1 ml) was also used at concentrations of 100 pM, 1 nM and 10 nM. Fluorescent images at 340 and 380 nm were acquired at a rate of 2.6/sec. for 200 sec, with a Hamamatsu Argus 50 system (Hamamatsu Photonics). The objective lens was a 10× Nikon fluor. Only the ¼ evenly illuminated area of the whole image was acquired. Individual ratio values were obtained off-line for all cells within the area of interest. Three to five dishes of a given cell line were used for each experimental condition. The number of cells measured per cell line was at least 50. In most cases, experiments for each cell line were repeated on at least one separate occasion (minimum one week interval).

Bradykinin Induced Responses.—Bradykinin-induced release was tested in the present study as measure of $IP_3$-mediated functions. Bath application of 100 pM bradykinin elicited virtually no responses from control cells (N=11 cell lines). Only one cell line (AG07141) exhibited some noticeable responses, that did not reach "criterion" levels (CR, see below). In contrast, 13 out of 14 AD cell lines had clear responses and only one (I4) failed to meet criterion levels. Statistical analysis of percentages of responding cells revealed highly significant differences between AD and controls, p<0.0003 (Mann-Whitney). The difference between the two groups analyzed by contingency table (response/non-response, based on CR) was also highly significant, p<0.0005 (Fisher's exact test). Cell lines from Es showed responses similar to those of control cell lines, p=0.3 (Mann-Whitney, not significant). FIG. 16A illustrates the distribution of bradykinin responses, expressed as % of responding cells. Control and Es cell lines clearly cluster at or near "0% responding cells", while AD cell lines show a wider and higher distribution. FIG. 16B shows the group data differences and 16C illustrates the time course of a typical bradykinin induced response. A comparison between the Coriell and Italian (designated "III") samples showed no differences in terms of responsiveness/unresponsiveness, p=0.23, N.S. (Fisher's exact test). Higher bradykinin concentration ($\geq 1$ nM), elicited responses of similar magnitude, and in comparable number of responding cells in AD and controls, thus obscuring the differences in bradykinin sensitivity between groups.

Bombesin Induced Responses.—As previously reported (Examples 1–4; Ito, E. et al., Proc. Natl. Acad. Sci. USA 91:534–538; 1994) addition of 1 $\mu M$ bombesin elicited responses in all cell lines, even in the absence of external $Ca^{2+}$. The % of cells responding had a tendency to be greater in AD cell lines but did not reach statistical significance (p=0.08, Mann-Whitney). Following the CR for bombesin listed below, the magnitude of the responses, however, (measured as the integrated area from under the curve for all cells, from the onset to the end of the response) was significantly higher in AD cell lines (26956±4494.7, Mean±SEM) cell lines as compared to controls (5402.3±3606.4), p<0.004 (Mann-Whitney). Using the same CR, a contingency table analysis also shows significant differences between the two groups; all but 3 AD cell lines (N=14 total) had responses, while only 2 out of 10 control cell lines had responses, p<0.007 (Fisher's exact test). Moreover, taking into account all responses, without considering the Ce., the magnitude of the responses was still significantly higher in AD cell lines as compared to controls, p<0.005 (Mann-Whitney). As for bradykinin, the magnitude of the bombesin responses was similar for the Italian and Coriell cell lines, p 0.79, N.S. (Mann-Whitney).

TEA Induced Responses.—TEA stimulation (100 mM) resulted in $Ca^{2+}$ elevations in control cell lines as expected (See Examples 1–4). All 11 control cell lines exhibited significant $Ca^{2+}$ elevations, meeting "CR" (see below). As expected, the majority of the AD cell lines (10 out of 14) did not meet CR. The remaining 4 cell lines with responses on average still had a lower % of cells responding. Overall, there was a highly significant difference between % of cells responding in AD as compared to all control cell lines, p<0.0005 (Mann-Whitney). Contingency table analysis (response/no-response) also revealed a clear and significant difference, p<0.0004 (Fisher's exact test). The 3 Es cell lines had lower % of responding cells (one did not meet CR), and on average they had values closer to AD than control cell lines. The bar graph in FIG. 17A illustrates these results. A representative trace of the TEA induced response is depicted in FIG. 17B. Latency to the onset and magnitude of the responses were comparable within control lines as well as with the 4 AD cell lines with responses. The control cell lines used in AG06241, AG04260 and AG07141 showed virtually identical responses in the present study. Lack of responsiveness was found in AD cell lines AG06844, AG06848, AG07:375, AG07377, and AGO8170 used in both the past and present study. A comparison of the TEA responses from the originally tested control cell lines (Examples 1–4; Etcheberrigaray, R. et al., Proc. Natl. Acad. Sci. USA 90:8209–8213; 1993) and those obtained from the present control group, revealed no significant differences between the two control groups, p=0.38 (Fisher's exact test). Similarly, the lack of responsiveness of the previously tested AD group did not significantly differ from the AD cell lines used in this study. Moreover, an overall comparison of TEA responses/lack of responses between the present and original sample showed no differences, p=0.55 (Fisher's exact test). In addition, no differences (response/no-response) where observed between the Coriell and Italian samples, p=0.24, N.S. (Fisher's exact test).

Integrated Index for Alzheimer's Disease.—Each individual molecular alteration described in AD cells has a high degree of specificity and sensitivity, and correctly identifies and separates AD cases from controls. For diagnostic purposes, it is desirable to maximize specificity and sensitivity. Therefore, a combined scoring system taking into account all observable altered and normal responses in fibroblasts from AD and control cells respectively was devised. The combined score generates a numerical index whose negative values indicate the pathological response for each challenge. Positive values indicate the opposite. A combined index value <0 indicates AD, values $\geq 0.5$ would identify normal or non-AD conditions. Criterion responses defined based on the responses of all cell lines examined and scoring criteria for each challenge is as follows:

| Treatment | Response | Score |
|---|---|---|
| Bradykinin (0.1 nm) | <1.5% responding cells | 0 (no response) |
| (Latency of the | $\geq 1.5\%$ responding cells | −0.5 |

-continued

| Treatment | Response | Score |
|---|---|---|
| onset ≤ 135 sec) | ≥4.0% responding cells | −1.0 |
| TEA (100 mM) | <5% responding cells | 0 (no response) |
| (Latency of the onset ≤ 60 sec) | ≥5% responding cells | 0.5 |
| | ≥16% responding cells | 1.0 |
| Bombesin* (1 μm) | <50% responding cells or area < 23000 nM-sec | 0 (no response) |
| (Latency of the onset ≤ 40 sec) | ≥50% responding cells and area ≥ 23000 nM-sec | −0.5 |
| | ≥50% responding cells and area ≥ 30000 nM-sec | −1.0 |

*Calcium free media

The results clearly indicated that taking into account the overall profile of responses increase the diagnostic value of these cellular alterations. The index allows the detection of all control and AD cases without a single overlap. Even though some AD cell lines do not express all AD "molecular phenotypes", in combination they express sufficient alterations to be correctly identified by the index system. Thus, this method of considering three or more diagnostic parameters adds specificity and sensitivity.

Bombesin induced responses were higher in AD fibroblasts as expected. (See Examples 1–4) The bombesin and bradykinin results are consistent since both agents induce $IP_3$ generation. Responses induced by 100 pM bradykinin turned out to have an even higher degree of specificity for identifying AD cells than TEA or bombesin-induced responses.

TABLE 7

| Line # | Bradykinin | TEA | Bombesin | Index |
|---|---|---|---|---|
| Alzheimer's | | | | |
| AG06848 | −1 | 0 | −1 | −2 |
| AG08170 | −1 | 0 | −0.5 | −1.5 |
| AG06844 | −1 | 0 | −1 | −2 |
| AG08527 | −1 | 0 | −0.5 | −1.5 |
| AG07375 | −1 | 0 | −0.5 | −1.5 |
| AG07377 | −1 | 0 | −1.0 | −2.0 |
| AG06262 | −1 | 0.5 | −0.5 | −1 |
| I4 | 0 | 0.5 | −1 | −0.5 |
| I6 | −1 | 0 | 0 | −1 |
| I8 | −0.5 | 0 | −0.5 | −1 |
| I24 | −0.5 | 1 | −1 | −0.5 |
| I41 | −1 | 0 | 0 | −1 |
| I43 | −1 | 0 | −1 | −2 |
| I46 | −1 | 0.5 | 0 | −0.5 |
| Controls | | | | |
| AG06241 | 0 | 1 | N.T. | 1 |
| GM04260 | 0 | 1 | −0.5 | 0.5 |
| AG07141 | −0.5 | 1 | 0 | 0.5 |
| AG05266 | 0 | 0.5 | 0 | 0.5 |
| I26 | 0 | 1 | 0 | 1 |
| I29 | 0 | 1 | 0 | 1 |
| I39 | 0 | 1 | 0 | 1 |
| I2 | 0 | 0.5 | 0 | 0.5 |
| I9 | 0 | 1 | 0 | 1 |
| I13 | 0 | 0.5 | −0.5 | 0 |
| I37 | 0 | 0.5 | 0 | 0.5 |

Table 7 shows the scores and final index for each cell line analyzed with this method. It is clear that control cell lines have positive scores, while AD cell have negative scores. Only one of the control lines had a score of 0, which is still greater than all AD cell lines. Statistical analyses of the index revealed a highly significant difference between AD and controls, p<0.0001 (Mann-Whitney). FIG. 18 depicts the distribution of the scores of controls and AD cell lines. In the AD scoring system, a numeric value is assigned (see text) according to the response for each cell line. The sum of the scores generates a final index value. This index value distinguishes AD from all controls. Both the sensitivity and specificity of the index for this sample are 100%.

The invention has been described in detail with particular reference to the preferred embodiments thereof, but it will be understood that the invention is capable of other and different embodiments. As is readily apparent to those skilled in the art, variations and modifications can be affected within the spirit and scope of the invention. Accordingly, the foregoing disclosure and description are for illustrative purposes only, and do not in any way limit the invention, which is defined only by the claims.

EXAMPLE 8

Differential effects of β-amyloid on PKC isoenzymes in Alzheimer's and non-Alzheimer's cells Materials and Methods Cell lines and procedure for cell culture. Human skin fibroblasts were grown to confluence in 75 cc growing surface culture flasks (Falcon) containing Dulbecco's modified Eagle's medium (DMEM, Gibco), supplemented with 10% fetal bovine serum (Gibco). Cells from six familial AD individuals [AG07872, AG06840B, AG8170B, AG08527A*, AG06848B*, AG08563A; four males and two females; 57.7±2.1 years of age (mean±SD); *, autopsy confirmation], four non-familial AD individuals (AG05770D*, AG07377, AG06263, AG06838; two males and two females; 53.8±1.1 years of age; *, autopsy confirmation), ten age matched AC individuals (AG07665A, AG06842B, AG07867, AG07603A, AG04560B, AG06241B, AG3652C, AG07141, AG08044A, AG07310; six males and four females; 55.2±2.9 year of age) were used. These cell lines are available through Coriel Cell Repositories. There were no differences in growth rates or time to senescence between AD and control fibroblasts (Tesco, G., et al. (1993) *Experimental Gerontology* 28:51–58).

Rat cerebellar granule cells were prepared from rat cerebella. Cerebella from 8-day old rat were dissociated after trypsinization (0.025% trypsin solution) and trituration in the presence of DNAse (0.01%) and trypsin inhibitor (0.05%). Cells were then dispersed and cultured into basal medium Eagle's (BME) supplemented with 25 mM KCL, 2 mM glutamine, 10% fetal bovine serum (Gibco). The growth of non-neuronal cells was inhibited by the addition of 20 μM cytosine β-D-arabinofuranoside.

Cortical neuron cultures were obtained from rat cortical tissues. Cortical tissue was extracted from fetuses of a 17-day pregnant rat by C-section. Fetal brains were dissected, dissociated in a solution containing 26 U/mg papain and 1 mM cysteine, and dispersed in DMEM supplemented with 10% fetal bovine serum, 100 IU/ml penicillin and 100 μg/ml streptomycin. Cells were then seeded for 72 h before addition of 1 μM cytosine β-D-arabinofuranoside.

Procedures for β-amyloid treatment. β-amyloid protein (1–40) (Bachem) was initially dissolved in dimethyl sulfoxide (100 μM DMSO) and further diluted in saline solution to desired final concentrations (1 nM to 5 μM). β-amyloid protein was added 24 hours after seeding and experiments were conducted starting from 24 to 120 h after addition of β-amyloid protein. None of these concentrations of β-amyloid tested has been shown to alter basal levels of intracellular calcium or cause other nonspecific cell damage (Etcheberrigaray, R et al. (1995) Science 264:276–279).

Procedures for protein extraction. Culture medium was removed by aspiration and replaced with ≈20 ml of cold (4° C.) PBS. The cells were scraped from the flasks and centrifuged at 10,000× g for 10 min. at 4° C. Supernatant was discarded, the pellet washed with 1 ml PBS and then inverted to remove any remaining PBS for about 2–3 min. Pellets were washed with 1 ml of homogenization buffer" containing 0.1 M HEPES, 0.04 M EDTA, 0.8 M sucrose, 0.01 M phenylmethylsulphonyl fluoride, 2.4 U/ml aprotinin and 0.1 SDS, transferred to Eppendorf tubes and centrifuged for 10 min at 10,000× g at 4° C. The pellet was sonicated for 10–20 sec in a ultrasonic homogenizer (Cole-Parmer Instruments). The crude protein extract was stored at –80° C. for later analysis.

Procedures for protein assay and immunoblotting. Protein concentration was determined following an established dye-binding protein assay (R. D. Lane et al. (1986) *J. Immunol Methods* 92:261) for all homogenates. For immunoblots, SDS-PAGE was carried out in a 4–20% acrylamide gradient gel of 1.5 mm thickness (Novex). The crude homogenate was balanced with sample buffer containing 0.5 M Tris HCL, pH 6.8, 10% glycerol, 2% SDS, 0.5% 2-mercaptoethanol, to a final volume of 20 µl with a final protein concentration of 10 µg/µl. The samples were electrophoresed and transferred overnight into a nitrocellulose paper (Schleicher & Schuell). The nitrocellulose was blocked in 1% BSA/95% TBS for 1 hour and then incubated with different PKC isoenzyme antibodies (PKCα, PKCβ, PKCγ, PKCδ, PKCε) monoclonal antibodies; Transduction Laboratories) for 1 hour. Blots were then incubated with an anti-mouse alkaline phosphatase-conjugated antibody (Sigma) for 1 hour. Finally, the nitrocellulose was stained with a solution containing 0.1 M Tris HCL, pH 9,6, 0.001 M $MgCl_2$, 1% nitroblue tetrazolium (Pierce) and it 5-bromo-4-chloro-3-indolyl phosphate toluidine salt (Pierce). All reactions were carried out at room temperature. Immunoblots were digitized on a flatbed scanner and analyzed by quantitative analysis with an imaging software written in the laboratory (TNIMAGE by T. J. Nelscn). Measurements of the regions of interest were normalized to the total densitomeric area per lane.

Confocal microscopy. Fibroblasts from AD and control patients were seeded onto a 75 mm×25 mm×0.5 mm glass microscope slides and processed to determine the immunofluorescent content of the different PKC isoenzyme. Cells were fixed with 4% formaldehyde, permeabilized in 0.1% Triton X100 and incubated with monoclonal antibodies against different PKC isoenzyme for 10 min. Fibroblasts were then washed and incubated for 20 min in the presence of an anti-mouse antibody conjugated with fluorescein. The slides were mounted on coverslip, and visualized on an inverted laser confocal microscope system (Zeiss) using a 63× (Neofluar) objective. Four-second-activation scans of the fluorescent antibody complex from the upper plasma membrane level to the nuclear and lower plasma membrane level were accomplished via an external 488 nm ArKr laser with a BS568 line filter to create confocal images and collected in a 10 sec/image set sequence. Simultaneous scanning using the internal HeNe red 647-nm laser line was used to produce bright-field images of the cells to assess cell viability. No significant bleaching of the fluorescent probe was observed during the course of observation.

RESULTS

Fibroblasts from AD patients and age-matched controls (AC) were cultured as described in the Materials and Methods. PKC isoenzymes were assessed by using monoclonal antibodies which recognize different PKC isoenzymes. Immunoblot analyses revealed significant differences in immunoreactivity for the PKCα and PKCγ isoenzymes after a 48 hour treatment of AC or AD fibroblasts with 10 nM β-amyloid, while no changes were observed for the other PKC isoenzymes tested (PKCβ, PKCδ and PKCε). In particular, distinct dark bands of about 82 kD for PKCα and 80 kD for PKCγ were detected with monoclonal antibodies in all the age-matched controls and in the 6 familial AD and 4 sporadic AD cell lines. PKCα immunoreactivity was significantly reduced in all AD fibroblasts as compared to the controls before β-amyloid treatment was administered (Table 8).

TABLE 8

| | AC | | | AD | |
|---|---|---|---|---|---|
| Patient # | Control | βAP | Patient # | Control | βAP |
| PKCα | | | | | |
| AG03652C | 1238.8 + 35* | 121.1 + 23* | AG07872 | 507.3 + 102* | 532.9 + 78* |
| AG07310 | 1031.1 + 208* | 145.3 + 41* | AG06263A | 468.2 | 399.7 |
| AG06241B | 880.5 + 103* | 267.5 + 94* | AG06848B | 584.5 | 451.5 |
| AG08044A | 1340.3 + 211* | 214.1 + 71* | AG08563A | 656.5 + 38* | 534.1 + 103* |
| AG07141 | 1141.3 + 301* | 466.7 + 107* | AG05770D | 880.8 | 799 |
| AG07603A | 1472.3 + 251 | 330.6 + 122* | AG06838A | 664.2 | 603.2 |
| AG06842B | 813.7 + 219* | 243 + 100* | AG07377A | 575.1 | 337.8 |
| AG07665A | 1143.9 + 291* | 312.2 + 101* | AG08527A | 682 | 538.2 |
| AG04560B | 1871.2 + 437 | 420.1 + 122* | AG06840B | 153.9 | 117 |
| AG07867 | 778 + 283 | 194.7 + 18* | AG08170B | 660.8 | 573.9 |
| PKCγ | | | | | |
| AG03652C | 486.3 | 497.9 | AG07872 | 642.1 | 129.6 |
| AG07310 | 841.5 | 774.4 | AG06263A | 1087.5 + 227* | 233.4 + 71* |
| AG06241B | 784.1 + 302* | 1006.5 + 201* | AG06848B | 894.5 + 318* | 249.2 + 102* |
| AG08044A | 2189.3 | 2056.2 | AG08563A | 1029.6 + 211* | 234.7 + 99* |
| AG07141 | 714.8 | 616.1 | AG05770D | 1312.8 | 202.1 |
| AG07603A | 124.6 | 121 | AG06838A | 1751.5 + 171* | 323.5 + 38* |
| AG06842B | 1479.1 | 1454.7 | AG07377A | 448.8 + 118* | 184.7 + 41 |
| AG07665A | 2095.1 | 2023.8 | AG08527A | 776.3 | 132.1 |
| AG04560B | 1781.5 | 1849.1 | AG06840B | 2115.7 | 449.7 |
| AG07867 | 1211 + 251* | 1174 + 76 | AG08170B | 2178 | 1002.2 |

No significant changes in PKCγ immunoreactivity were detected between the non-treated AC and AD groups. Western blot analysis of fibroblasts treated with β-amyloid showed a dramatic reduction cf PKCα immunoreactivity in all ten AC cell lines (FIG. 19A), while no changes were observed in any of the ten AD cell lines after β-amyloid treatment (FIG. 19B). Interestingly, the treatment of the AD fibroblasts with 10 nM β-amyloid for 48 h did lead to a significant decrease in PKCγ immunoreactivity in all ten AD cell lines as compared to the treated controls (FIG. 19C). None of those effects were observed in either the AC or AD groups when other β-amyloid fractions [βAP(1–28) or βAP (25–35) or βAP(1–42)] were used (data not shown). Quantitative analysis of the bands confirmed the visual observations (Table 8). Scatter plots of each cell line showed little or no overlap between treated and non-treated fibroblasts (FIG. 20) for the AC or AD groups statistical analyses showed that the treatment of AC fibroblasts (n=10) with β-amyloid led to a 75%±11.3 (P<0.001) decrease in PKCα immunoreactivity as compared to the non-treated controls (FIG. 21A), but β-amyloid treatment of AD fibroblasts (n=10) did not further affect PKCα immunoreactivity as compared to the non-treated AD cells. On the other hand, fibroblasts from the AD group (n=10) treated with β-amyloid showed a 70%±24.8 (P<0.001) decrease in PKCγ immunoreactivity as compared to their controls (n=10), but no changes in PKCγ immunoreactivity were observed between treated and non-treated AC fibroblasts (n=10) (FIG. 21B). Double blind tests conducted on 2 AC and 2 AD cell lines confirmed all of the above results (data not shown).

To test whether the changes in PKCα and PKCγ immunoreactivity were mediated by proteasome-mediated degradation, immunoblot analyses were performed after preincubation of AC or AD fibroblasts with 50 µM of lactacystine (Lacta), a selective proteasome inhibitor, for 1 h before treatment with 10 nM β-amyloid for 48 h. Pretreatment with Lacta prevented degradation of PKCα in AC fibroblasts after exposure to βamyloid (FIG. 22A). Similarly, PKCγ degradation was blocked by Lacta in AD fibroblasts treated with β-amyloid FIG. 22B).

β-amyloid effects on PKC were also observed in rat cerebellar and cortical neurons. Western blot analysis showed that the treatment of rat cerebellar granule cells with 10 nM β-amyloid for 48 h significantly decreased PKCα (but not PKCγ) immunoreactivity after 4 and 6 days of maturation in vitro (DIV). No modifications in either PKCα or PKCγ immunoreactivity were observed at 0 or 2 DIV (FIG. 23A). Similarly, PKCα (but not PKCγ) immunoreactivity was reduced in rat cortical neurons at 10 DIV after treatment with 10 nM β-amyloid for 48 h (FIG. 23B).

Since recent evidence reported that phorbol esters downregulate PKCα via the ubiquitin/proteasome pathway (Olds, J., et al. (1995) *Developmental Biology* 172:675–682), AC and AD fibroblasts were exposed to 100 nYM phorbol 12-myristate 13-acetate (PMA) for 3 hours. This treatment, which causes membrane translocation but not downregulation of PKC, selectively reversed the effects of β-amyloid on PKC (immunoreactivity in AC fibroblasts (FIG. 24). Surprisingly, PMA was not effective in restoring the PKCγ signal after β-amyloid treatment in AD fibroblasts (FIG. 25A). To test whether the phorbol ester restoring effects on PKCα were mediated by protein synthesis, AC fibroblast treated with β-amyloid were incubated with 100 µM cycloheximide (CHX), a protein synthesis inhibitor, for 30 min be-ore exposure to PMA (FIG. 24). Pretreatment with CHX prevented phorbol esters from restoring PKCα immunoreactivity in AC fibroblasts (FIG. 25A). Interestingly, preincubation with 100 µM CHX for 30 min before the addition of α-amyloid induced a significant inhibition of the β-amyloid effects on PKCα in AC fibroblasts (FIG. 25A), suggesting that β-amyloid requires de novo protein synthesis to mediate PKCα degradation in non-affected fibroblasts. However, CHX was not effective in preventing ±-amyloid-mediated PKCγ changes in AD cells (FIG. 25B).

Confocal microscopic imaging confirmed the Western blot results showing that the a PKCγ immunofluorescent label localized in the perinuclear area was restored by PKC activation in β-amyloid treated AC fibroblasts (FIG. 26). The effects of PMA were also observed in rat cortical neurons, where exposure of β-amyloid-treated neurons at 10 days of maturation in vitro (DIV) to 100 nM PMA for 3 h restored PKCα, but not PKCγ, immunoreactivity (FIG. 23B).

These results clearly demonstrated that the soluble form of the β-amyloid protein differentially affects PKCα and PKCγ in normal and Alzheimer fibroblasts. Moreover, the β-amyloid concentrations used for this study, although affecting signal transduction by degradation of PKCα in AC cells and PKCγ in the AD cells, did not affect cell viability or induce any neurotoxic effect.

In addition to providing the first evidence of a selective effect of β-amyloid on PKC regulation in human cells, the findings presented herein also suggest novel research directions for early diagnosis of Alzheimer's disease and protection of neuronal cells against β-amyloid toxicity, perhaps in an early stage of the disease. For example, the findings that β-amyloid did not induce any modification in PKCγ content in non-affected fibroblasts or in cerebellar or cortical neurons, suggests that the effects of β-amyloid on PKCγ may be selective for those cells which are already physiologically compromised by the Alzheimer's disease. Indeed, the β-amyloid effects in cultured neurons from the cerebellum and the cortex of newborn rats demonstrated that changes in PKCα immunoreactivity occurred only after a critical stage of development had been achieved and other studies conducted on rat hippocampal neurons or mouse cortical neurons suggested that aging and cell differentiation help determine β-amyloid effects on PKC.

In addition, the demonstration that β-amyloid-mediated PKCα and PKCγ degradation was blocked by the selective proteasome inhibitor, lactacystine (Lacta), suggests that in human fibroblasts β-amyloid effects on protein degradation may be mediated by an ubiquitination process. The finding also suggests that anti-proteolytic compounds such as Lacta may have therapeutic effects on Alzheimer's disease by preventing β-amyloid-mediated PKCγ degradation in Alzheimer's disease cells.

The observation that treatment with phorbol 12-myristate 13-acetate (PMA) selectively reversed the effects of β-amyloid on PKCα immunoreactivity in AC fibroblasts (an effect that was blocked by the presence of CHX) while it did not reverse the effects of β-amyloid on PKCγ immunoreactivity in AD fibroblasts, suggests that β-amyloid differentially affects PKC regulation in AC and AD cells via proteolytic degradation and that PKC activation exerts a protective role via de novo protein synthesis in normal but not Alzheimer's cells. It is believed that the this inability of phorbol esters to reverse the effect of β-amyloid protein on PKCγ in AD fibroblasts may be due to constitutive damage provoked by increased circulating levels of β-amyloid protein in Alzheimer's disease.

EXAMPLE 9

Alterations in Eu-TTA fluorescence intensity in Alzheimer's cells

The Eu-TTA fluorescence method is a newly developed thermal imaging technique for monitoring intracellular heat production and the method has been successfully used to detect intracellular heat signals generated by activation of m1-muscarinic receptors by acetylcholine (Zohar, O., et al. (1998) *Biophysical Journal* 74:82–89). Here, this method was utilized to detect differences in fluorescence intensity between AD and normal cells following treatment with bradykinin. The methods disclosed below for cell culture and measurement of Eu-TTA fluorescence are taken from the Materials and Methods section on page 83 of the Zohar paper, hereby incorporated by reference.

Procedure for cell culture

Human skin fibroblasts were grown on 35 mm glass-bottomed petri dishes containing Dulbecco's modified Eagle's medium (DMEM, Gibco), supplemented with 10% fetal bovine serum (Gibco) at 37° C. Before imaging, culture medium was replaced with BSS. Staining with Eu-TTA was done by adding 50 μM Eu-TTA to 3 ml of BSS and allowing the cells to incubate for 30 min at room temperature. The cells were then washed three times with BSS.

Procedure for measuring Eu-TTA fluorescence.

Eu-TTA-stained cells were excited by applying 100-ms UV light flashes (mercury 100 W) every second (excitation: 365±30 nm bandpass; dichroic: 480 am; emission:510 nm long pass; Omega Optical, Battleboro, Vt.). Heat evoked in the cells was recorded with a cooled CCD camera (256×256 pixel array; Hamamatsu 4880, Hamamatsu, Japan) connected to an inverted microscope (Axiovert 405M; Zeiss). Images were collected at 1.1-s-intervals. Data were collected on line by using a 40×1.2 NA Zeiss objective and were analyzed later cn a Pentium computer (Dell 133 MHz) using the Argus 50 system (Hamamatsu). During the experiments cells were continuously perfused with BSS (2 ml/min). Bradykinin was pressure applied (100 ms) at a distance of around 200 μm upstream of the recording area.

Dependence of the phosphorescence intensity of Eu-TTA-stained Chinese hamster ovary (CHO) cells on external temperature was imaged under temperature-controlled perfusion. The temperature of the perfused BSS was reduced to 15° C. for 70 s (as monitored by a thermocouple in the recording dish), after which the BSS temperature was allowed to reach 25° C. (by turning off the temperature-controlled water bath). Finally, the BSS temperature was cooled back to 15° C.

As the optical recordings of Eu-TTA luminescence were affected by both thermobleaching and photobleaching, and each pixel had a different initial intensity, each frame was divided by the first frame in the series on a pixel-to-pixel basis in order to normalize the images for intensity. Optical recordings of luminescence intensity change in Eu-TTA-stained cells as a result of changing bath perfusion temperature were taken. The calculated intensity ratio of the recordings at the two different temperatures was then determined.

RESULTS

Based on the demonstration in Example 7 that $IP_3$ production is elevated in response to bradykinin in Alzheimer's cells and the fact that bradykinin is known to activate the phosphoinositide cascade and induce $IP_3$-mediated calcium release, heat production generated in Alzheimer's disease cells and in healthy control cells following bradykinin treatment was measured using the Eu-TTA fluorescence imaging method.

Eu-TTA fluorescence in response to bradykinin was found to be more intense in Alzheimer's disease cells compared to that of the control cells (data not shown) thereby demonstrating that signal transduction abnormalities of Alzheimer's disease cells could be measured at the membrane level using the Eu-TTA fluorescence method. Furthermore, these results suggest that Eu-TTA fluorescence could be used to monitor functional and/or structural differences that may have been manifested through activation of receptor-mediated metabolic pathways and therefore could be used as an alternative method, or in conjunction with the other methods described herein, in the diagnosis of Alzheimer's disease.

We claim:

1. A method of diagnosing Alzheimer's disease in a patient, said method comprising the steps of:
   a) stimulating cells from said patient with β-amyloid (1–40), and
   b) comparing the protein level of PKCγ in stimulated cells to the protein level of PKCγ in unstimulated cells of the same type from said patient, wherein a reduction in the protein level of PKCγ in stimulated cells as compared to unstimulated cells indicates the presence of Alzheimer's disease.

2. The method of claim 1, wherein said cells are selected from the group consisting of fibroblasts, buccal mucosal cell, neurons, and blood cells.

3. The method of claim 2, wherein said cells are fibroblasts.

4. The method of claim 1 wherein said comparison step includes the following steps:
   a) contacting a protein sample from said stimulated or unstimulated cells with an antibody which recognizes PKCγ protein; and
   b) detecting the complex between said antibody and said PKCγ protein.

5. The method of claim 4, wherein said comparison step further includes the step of obtaining a protein sample from the stimulated and unstimulated cells.

6. The method of claim 4 wherein said antibody is a monoclonal antibody.

7. The method of claim 4 wherein said antibody is a polyclonal antibody.

8. The method of claim 4 wherein said protein is contacted with said antibody in an immunoassay selected from the group consisting of radioimmunoassay, Western blot assay, immunofluorescent assay, enzyme immunoassay, immunoprecipitation, chemiluminescent assay, immunohistochemical assay, dot blot assay and slot blot assay.

9. The method of claim 8 wherein said immunoassay is a Western blot assay.

10. A method of diagnosing Alzheimer's disease in a patient, said method comprising the steps of:
    a) stimulating cells from said patient with β-amyloid (1–40); and
    b) comparing the protein level of PKCα in stimulated cells to the protein level of PKCα in unstimulated cells of the same type from said patient, wherein an insignificant change in the protein level of PKCα in stimulated cells as compared to unstimulated cells indicates the presence of Alzheimer's disease.

11. A method of diagnosing Alzheimer's disease in a patient, said method comprising the steps of:
   a) stimulating cells from said patient with β-amyloid (1–40); and
   b) comparing the protein levels of PKCγ and PKCα in stimulated cells to the protein levels of PKCγ and PKCα in unstimulated cells of the same type from said patient, wherein a reduction in the protein level of PKCγ and an insignificant change in the protein level of PKCα in stimulated cells as compared to unstimulated cells indicates the presence of Alzheimer's disease.

* * * * *